(12) United States Patent
Laursen et al.

(10) Patent No.: US 9,625,418 B2
(45) Date of Patent: Apr. 18, 2017

(54) CONDUIT SENSOR DEVICE WITH MAGNETIC SHUNT AND PROCESS FOR MODIFYING A MAGNETIC FIELD

(75) Inventors: Paul Laursen, Toronto (CA); Corry Comello, Scarborough (CA)

(73) Assignee: INVODANE ENGINEERING LTD, Toronto (CA)

( * ) Notice: Subject to any disclaimer, the term of this patent is extended or adjusted under 35 U.S.C. 154(b) by 1160 days.

(21) Appl. No.: 13/549,453

(22) Filed: Jul. 14, 2012

(65) Prior Publication Data

US 2014/0015521 A1    Jan. 16, 2014

(51) Int. Cl.
    *G01R 33/09*    (2006.01)
    *G01N 27/82*    (2006.01)
    *F16H 1/22*     (2006.01)

(52) U.S. Cl.
    CPC .............. *G01N 27/82* (2013.01); *F16H 1/225* (2013.01); *G01N 2291/2636* (2013.01)

(58) Field of Classification Search
    CPC ...... G01R 33/09; G01R 31/40; G01R 31/025; G01R 33/07; G01R 21/00; G01R 31/2601; G01R 35/00; G01B 7/30
    USPC ...... 324/66, 67, 139, 143, 177, 772, 207.25, 324/415–425, 750.01–765.01, 200–263, 324/173–174
    See application file for complete search history.

(56) References Cited

U.S. PATENT DOCUMENTS

| 1,842,125 A | * | 1/1932 | Schwarz ................. B63H 7/02 244/51 |
| 2,698,920 A | | 1/1955 | Gieske |
| 4,447,777 A | | 5/1984 | Sharp et al. |
| 4,506,219 A | * | 3/1985 | Lee ..................... E21B 17/1021 175/325.2 |
| 5,115,196 A | | 5/1992 | Low et al. |

(Continued)

FOREIGN PATENT DOCUMENTS

EP    2407778 A2    1/2012

OTHER PUBLICATIONS

European Patent Office, Extended European Search Report, January 27, 2014, Application No. 13156720.8-1559/2685252, Applicant: Invodane Engineering Ltd., pp. 1-8.

(Continued)

*Primary Examiner* — Patrick Assouad
*Assistant Examiner* — Taqi Nasir
(74) *Attorney, Agent, or Firm* — Woodling, Krost and Rust

(57) ABSTRACT

A conduit sensor device comprises a first end portion, a second end portion, a first magnet rotor assembly residing proximate the first end portion of the device and rotatable between first and second positions, a second magnet rotor assembly residing proximate the second end portion of the device and rotatable between first and second positions. The first magnet rotor assembly includes a first plurality of magnets axially arranged about a first axis. The first magnet rotor assembly includes a first top portion and a first bottom portion securing the first plurality of magnets within the first magnet rotor assembly. The second magnet rotor assembly includes a second plurality of magnets axially arranged about a second axis. The second magnet rotor assembly includes a second top portion and a second bottom portion securing the second plurality of magnets within the second magnet rotor assembly.

25 Claims, 36 Drawing Sheets

(56) References Cited

U.S. PATENT DOCUMENTS

| | | | | |
|---|---|---|---|---|
| 5,426,367 | A | * | 6/1995 | Martin .................... G01V 3/28 |
| | | | | 324/221 |
| 5,565,633 | A | * | 10/1996 | Wernicke ............... G01N 27/82 |
| | | | | 324/220 |
| 5,636,071 | A | | 6/1997 | Mochizuki et al. |
| 5,747,998 | A | | 5/1998 | Fowler et al. |
| 6,009,756 | A | * | 1/2000 | Willems ............... G01N 27/902 |
| | | | | 73/592 |
| 6,100,684 | A | | 8/2000 | Ramaut |
| 6,762,602 | B1 | | 7/2004 | Laursen et al. |
| 2001/0017541 | A1 | | 8/2001 | Kwun et al. |
| 2009/0315544 | A1 | * | 12/2009 | Takahashi ............. F16C 41/007 |
| | | | | 324/207.25 |
| 2011/0234212 | A1 | | 9/2011 | Lepage et al. |
| 2012/0013330 | A1 | * | 1/2012 | Laursen ................ G01N 27/82 |
| | | | | 324/220 |

OTHER PUBLICATIONS

"Tigre: A Robotic Platform and MFL Sensor for the Inspection of Unpiggable Pipelines", Technology Brief, 2008, Northeast Gas Association, http://www.nysearch.org/publications/2008/20-Tigre-052908.pdf.

U.S. Appl. No. 12/836,230, filed Jul. 14, 2010, entitled Conduit Sensor Device With Magnetic Shunt and Process for Modifying a Magnetic Field, Inventors Paul Laursen and Corry Comello, allowed and issue fee paid but patent No. not yet provided.

* cited by examiner

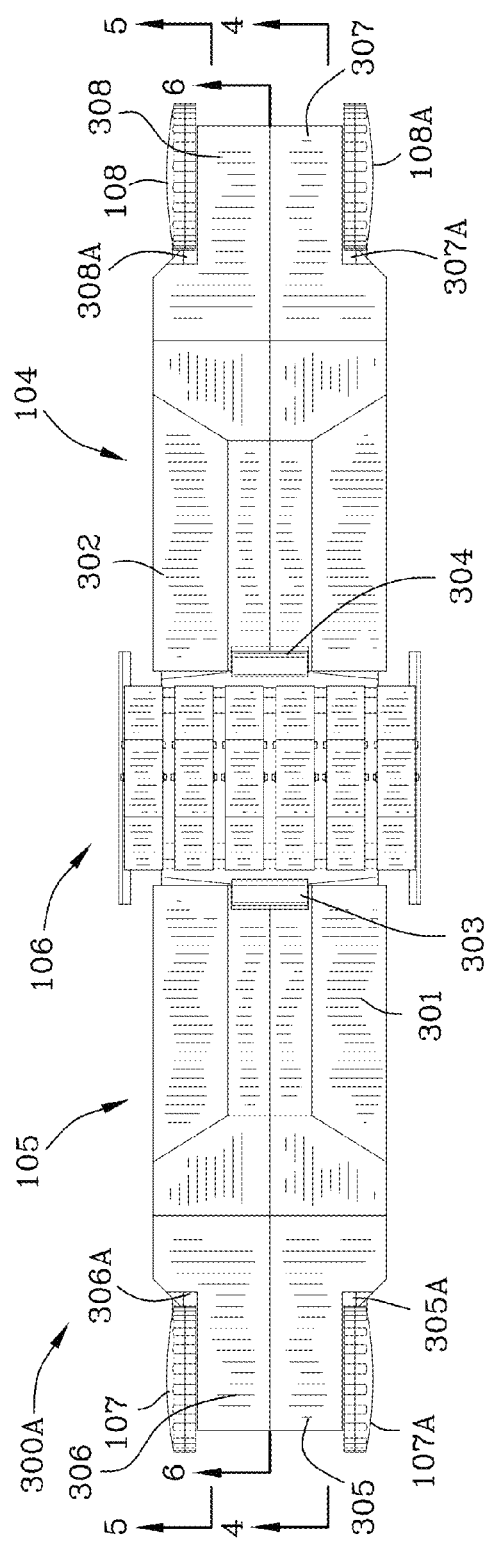
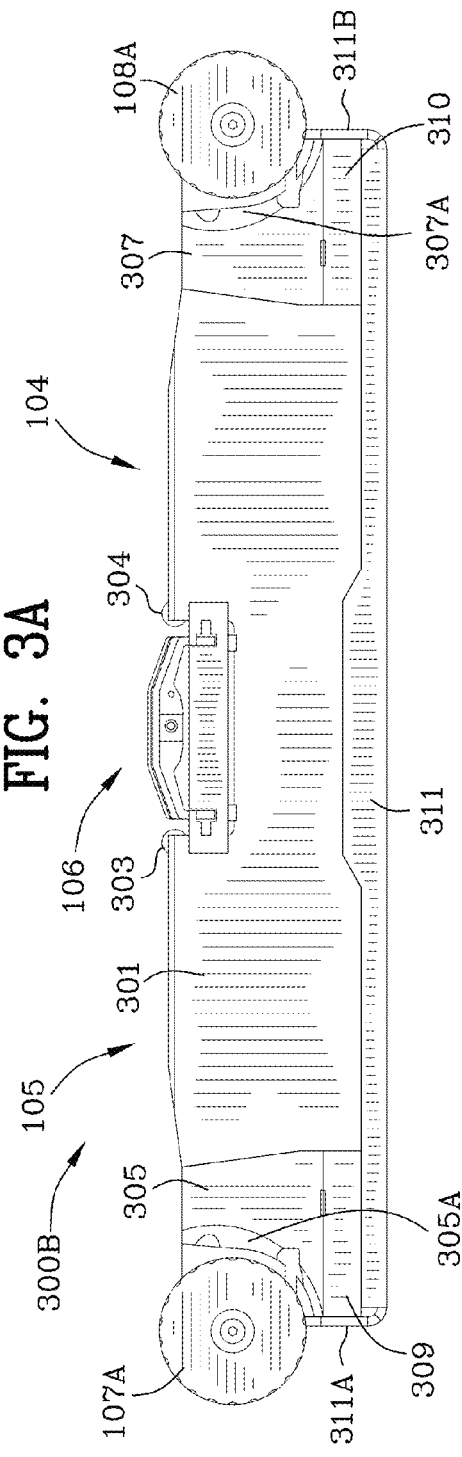

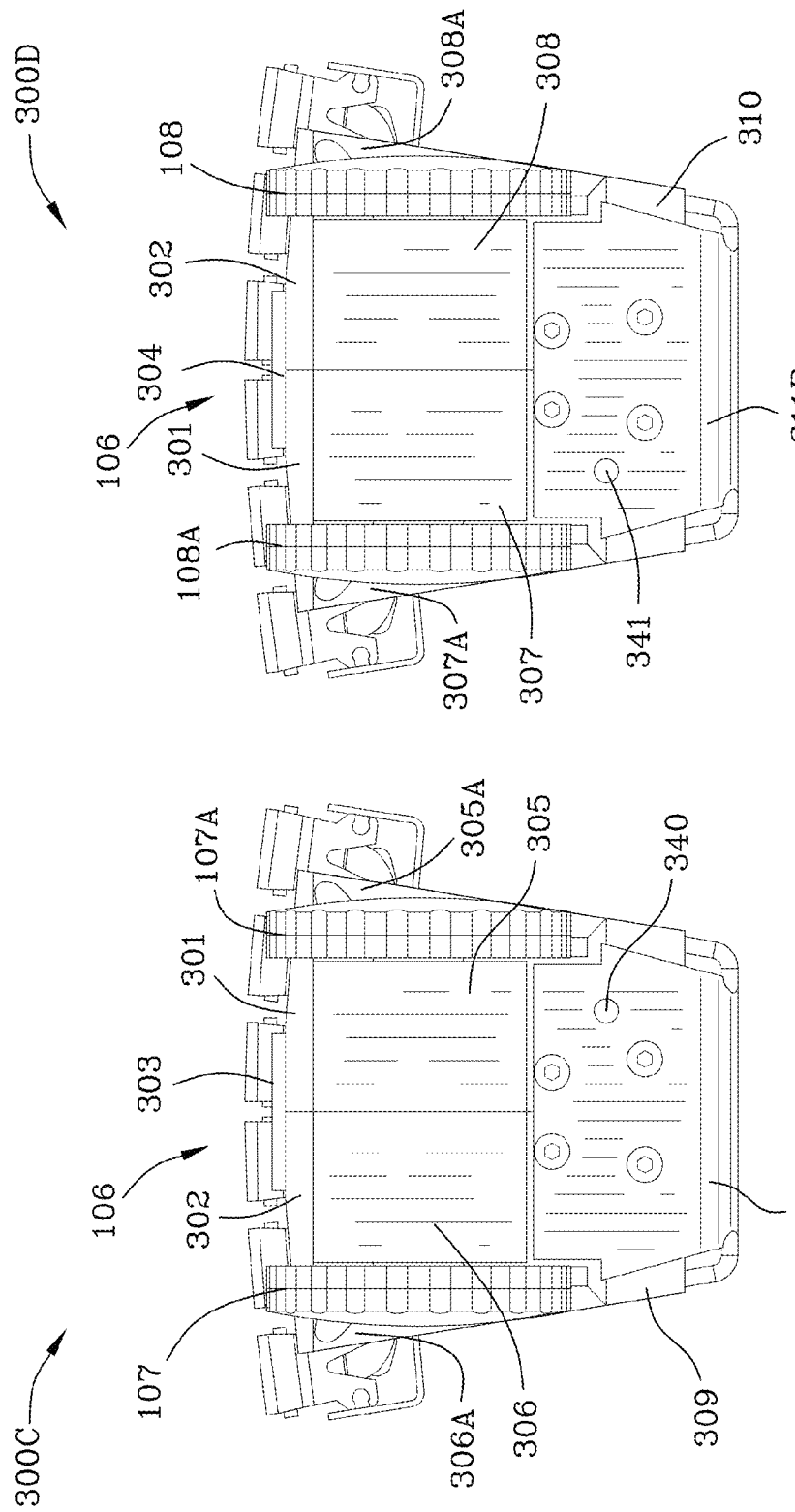

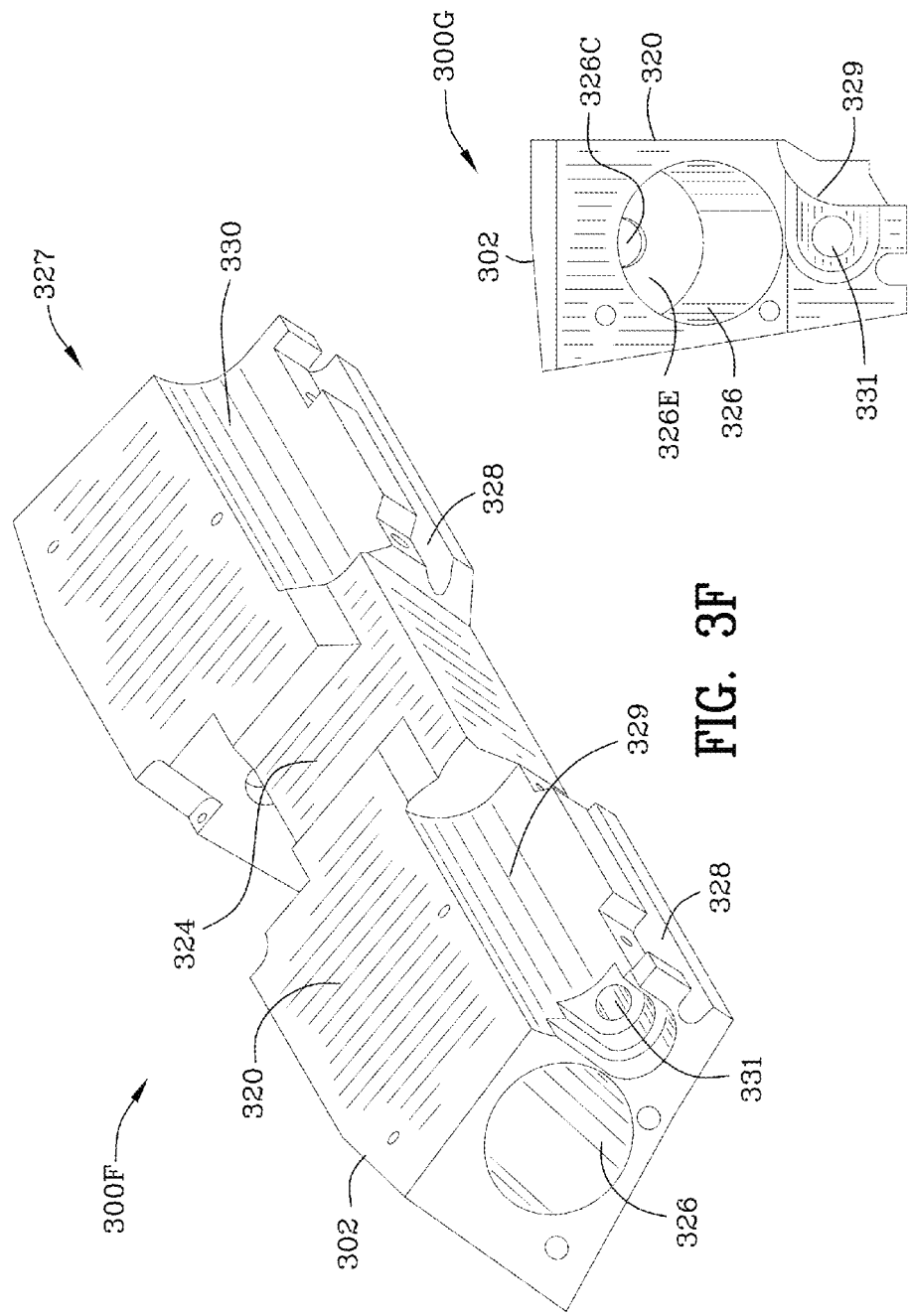

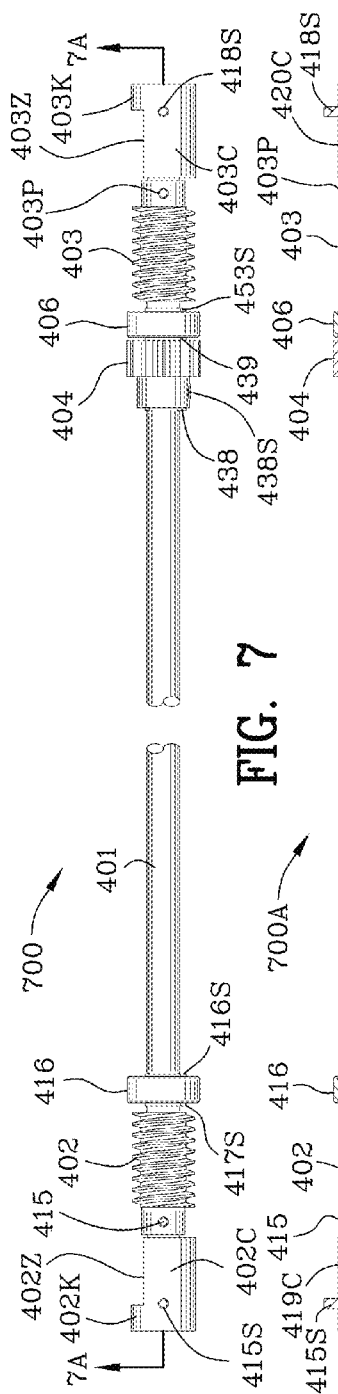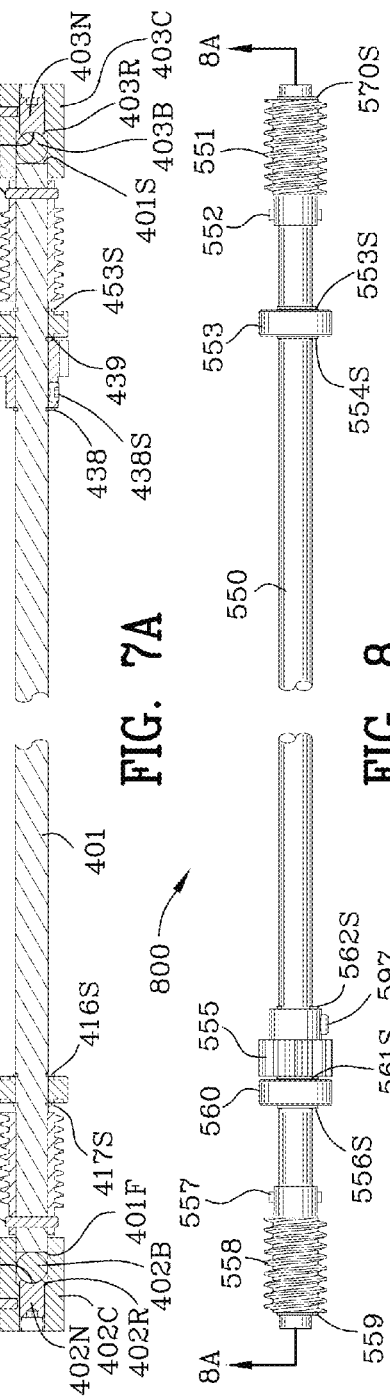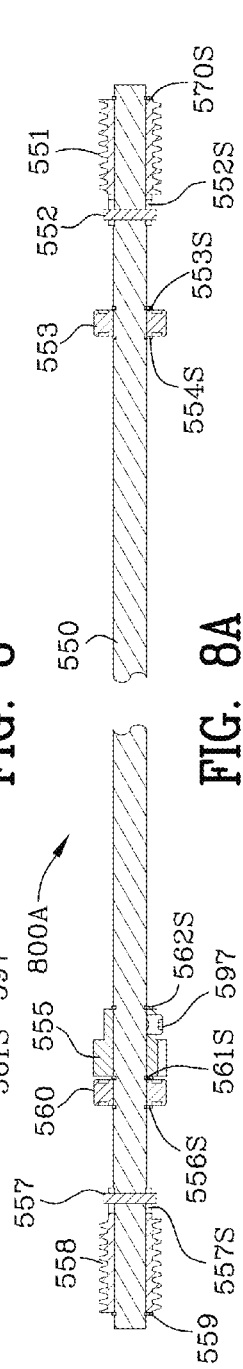

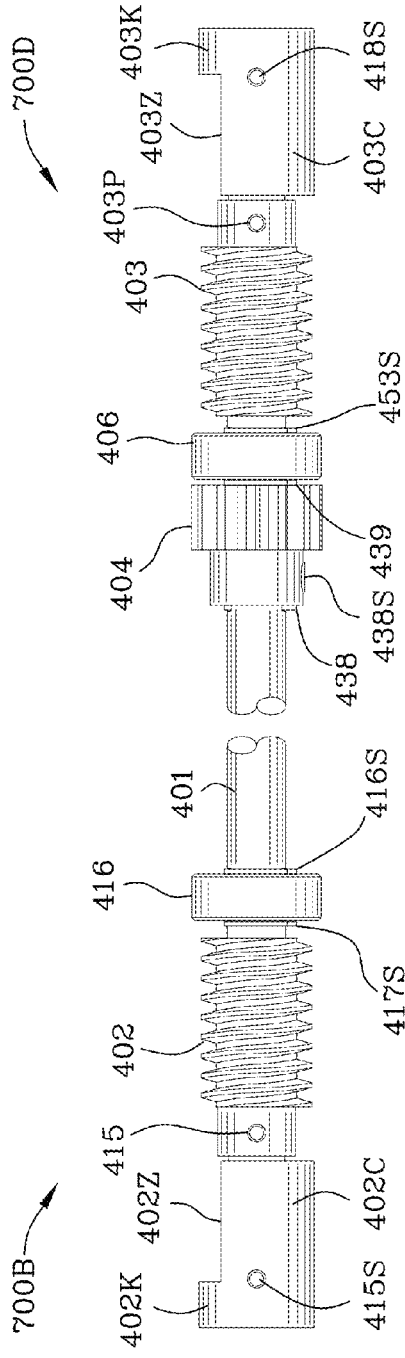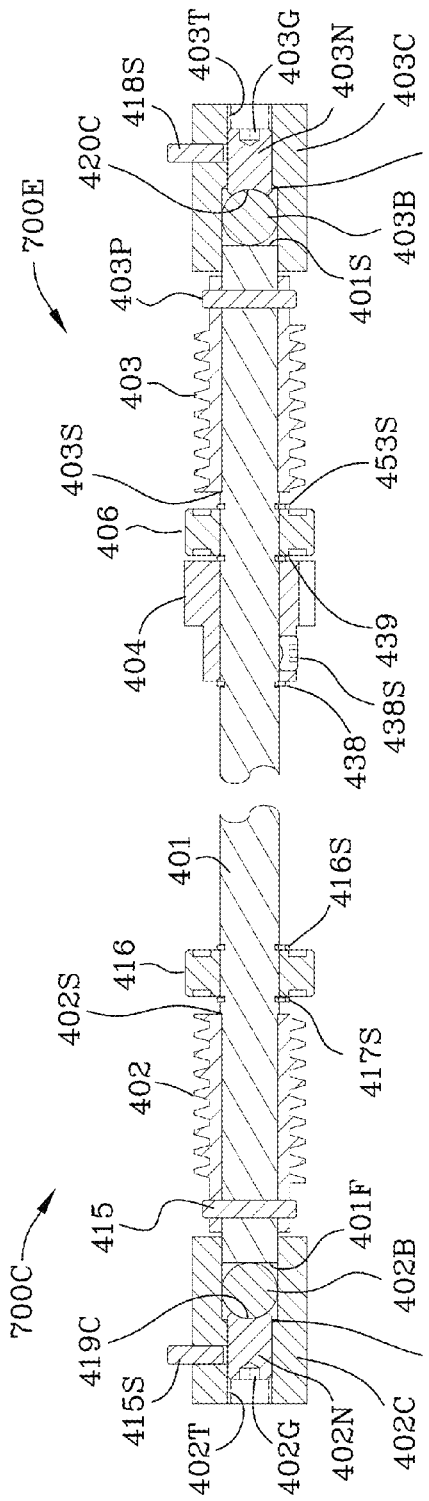
FIG. 7B  FIG. 7D
FIG. 7C  FIG. 7E

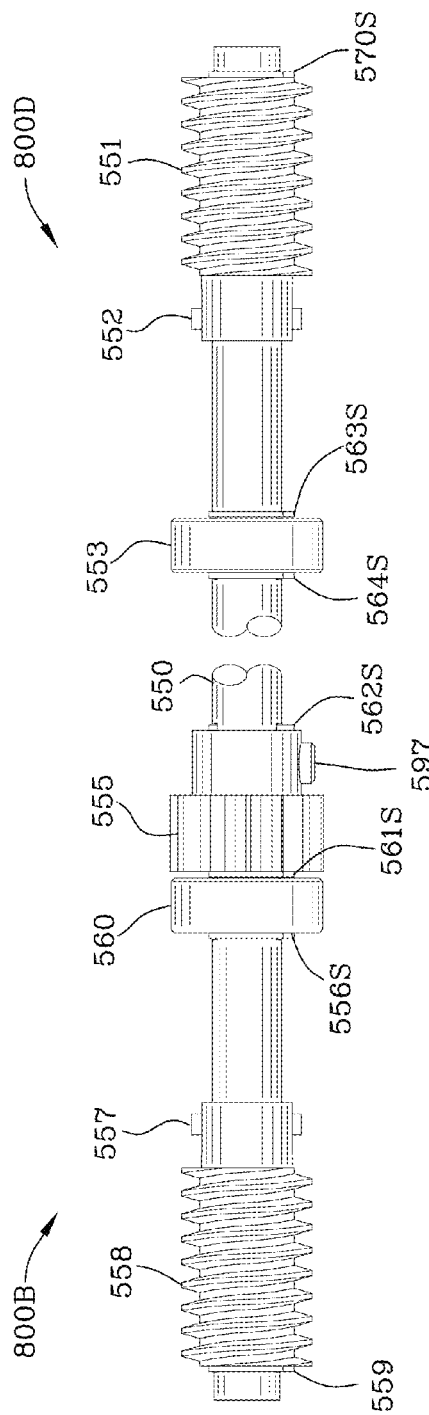
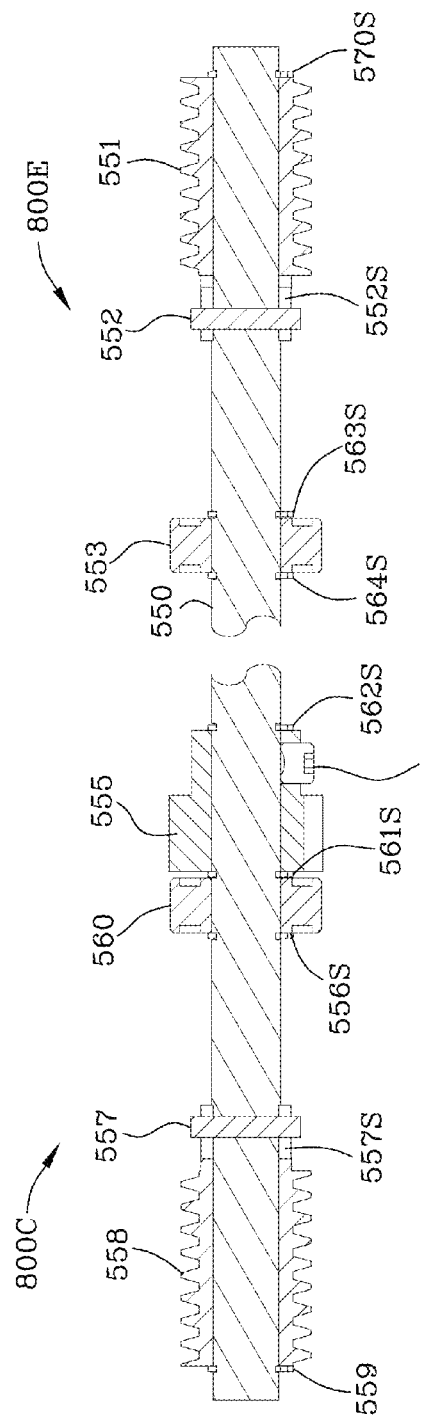
FIG. 8B
FIG. 8C
FIG. 8D
FIG. 8E

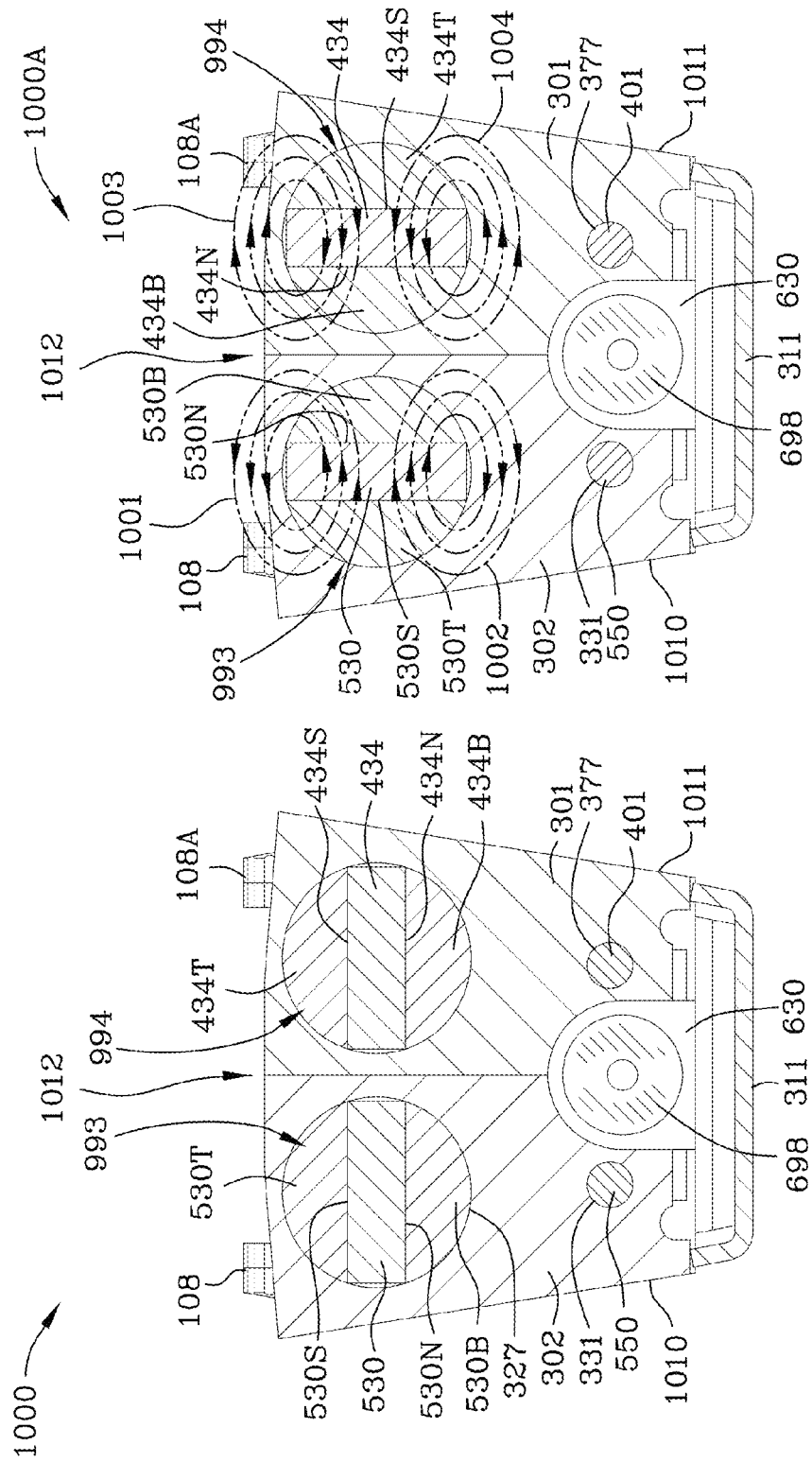

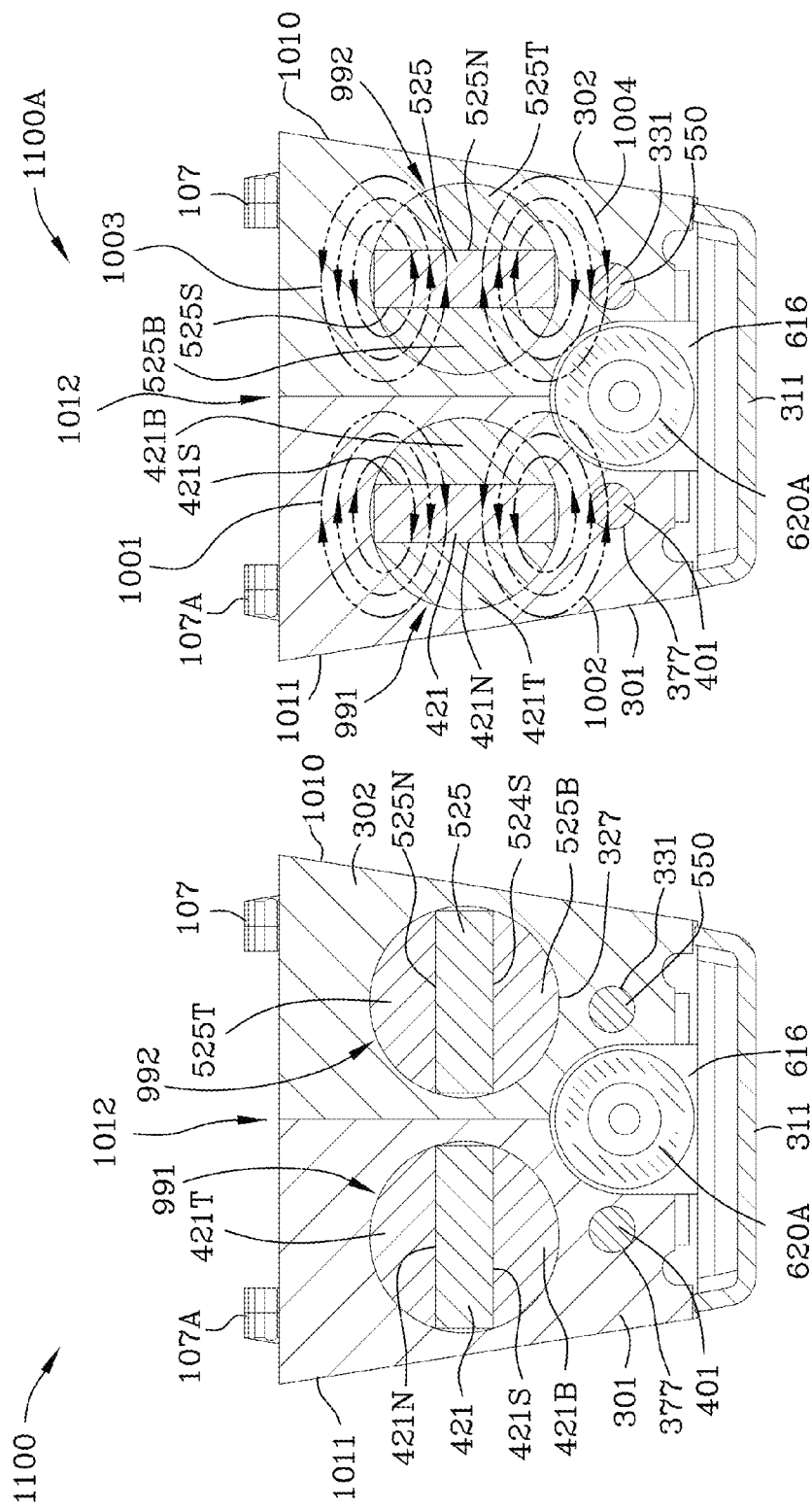

CONDUIT SENSOR DEVICE WITH MAGNETIC SHUNT AND PROCESS FOR MODIFYING A MAGNETIC FIELD

U.S. patent application Ser. No. 12/836,230 filed Jul. 14, 2010 is hereby incorporated by reference herein in its entirety by reference hereto the same as if written herein verbatim.

FIELD OF THE INVENTION

The invention is in the field of pipeline inspection devices/sensors.

BACKGROUND OF THE INVENTION

U.S. Pat. No. 6,762,602 to Laursen et al. proposed a "device, e.g. an inspection pig, for inspecting conduits made from ferromagnetic materials, such as pipelines, for faults, cracks, corrosion or the like, comprising at least one pulling element, a supporting structure of variable circumference, disposed on the pulling element and comprising substantially radially disposed supporting arms each of which is pivotable about axes disposed perpendicular to the longitudinal central axis of the pulling element, and several permanent magnets disposed at the circumference of the supporting structure for generating a magnetic filed, and with sensors." Further, Laursen, states, pertinent part: "[f]or strengthening or weakening the magnetic field generated by the permanent magnet in dependence on the circumference of the supporting structure or in dependence on the lateral separation between the permanent magnets. The permanent magnets are associated with further magnets having a magnetic field which can be varied in direction or strength. In an embodiment, the further magnets associated with the permanent magnets are permanent magnets, wherein the direction of their magnetic field can be changed by turning using an electric or mechanical actuator. In another embodiment coils are used as magnets, which can be supplied with a variable current." See, the Abstract of U.S. Pat. No. 6,762,602 to Laursen et al.

The diametrical size of the conduit, the thickness of the conduit, and the lateral separation of the poles of the magnet are factors in the performance of the sensor. Sensors such as piezo-electric, electro-acoustic, and electromagnetic sensors such as Hall, stray field and eddy current sensors may be used.

U.S. Pat. No. 6,762,602 to Laursen et al. does not effectively shunt the magnetic field produced by the poles through use of respective rotatable magnets. Additionally, the drive system of the rotatable magnets disclosed in U.S. Pat. No. 6,762,602 to Laursen et al. involves a mechanical system using springs and a toothed wheel with a selected diameter and selected number of teeth. The diameter and the number of teeth may be changed to control the rotatable magnet. Further, a spring is necessary for each of the rotatable magnets and adjustment of those magnets in a coordinated manner is difficult, and, therefore, control of the magnetic field is difficult. One of the poles in the Laursen '602 patent may be adjusted differently than the other pole because the springs and toothed gears cannot be matched or properly controlled. Spring constants and biasing of the rotatable magnets in Laursen et al. may not be equal and, hence, contribution of each of the poles to the magnetic field may be different.

Alternatively, U.S. Pat. No. 6,762,602 to Laursen et al., further discloses an electrically driven toothed wheel which is controlled by appropriate electric, electronic or mechanical sensor element for determining the lateral separation between the parallelogram supports. However, there is no disclosure in Laursen as to the coordinated operation and control of the rotatable magnets.

A more effective magnetic shunt which substantially completely reduces the magnetic field associated with a plurality of inner peripheral sensors is needed for unpiggable pipe lines. So-called unpiggable pipe lines require substantial cancellation of the magnetic field caused by permanent magnets used in conduit sensors placed in proximity to the conduit/pipe line. When the field created by the permanent magnets is substantially cancelled, the sensor may be drawn more easily through the pipeline as the sensor and its supporting structure are no longer magnetically attracted to the walls of the conduit/pipeline.

Use of a conduit sensor device requires application of north and south poles in proximity to the conduit/pipe line wall which creates a magnetic field extending into the wall of the conduit/pipe line. Control of the magnetic field which enters the conduit/pipe line is necessary for the correct interpretation of data obtained from the sensors. Sensors, such as a Hall effect sensors, measure anomalies such as cracks and deterioration of the structure of the conduit/pipeline when a magnetic field is imparted in the conduit/pipeline. Control of the magnetic field imparted in the conduit/pipeline is important as it allows correct interpretation of the data generated from the sensors. As such, a conduit sensor device which accurately controls the magnetic field in the conduit/pipeline wall is needed.

SUMMARY OF THE INVENTION

The conduit sensor disclosed herein controls the magnetic field as required to obtain accurate data and to allow movement through a pipeline or conduit. Additionally, the conduit sensor disclosed herein is self-propelled in two directions, forwardly and rearwardly.

There is a plurality of conduit sensor devices arranged on the inner periphery of the pipeline/conduit which form an inspection pig. Each conduit sensor device includes several sensors associated therewith and each device covers a sector of the pipeline/conduit. Any number of conduit sensors may be used to form an inspection pig.

Each conduit sensor device includes a magnetic shunt device. The magnetic shunt device is used to effectively turn off the magnetic field. The inspection pig is propelled through the pipeline/conduit by drive means which are disclosed herein. Each of the conduit sensor devices propels the conduit sensor device through the pipeline to be inspected. Further, and importantly, the magnetic shunt device enables the curtailment of the magnetic field in the pipeline/conduit making movement of the inspection pig within the interior of the pipeline/conduit and through valves and other obstructions inside the pipeline easier.

Further, the magnetic shunt device imparts an appropriately adjustable magnetic field into the pipeline/conduit as dictated by the operation of the inspection pig and/or as required for other reasons such as comparison of the data presently being taken against previously taken data for a given conduit/pipeline.

A conduit sensor device comprising a first end portion and a second end portion is disclosed. A first magnet rotor assembly resides proximate the first end portion of the device and is rotatable between first and second positions. A second magnet rotor assembly resides proximate the second end portion of the device and is rotatable between first and second positions. The first position of the first magnet rotor assembly in combination with the first position of the second magnet rotor assembly creates the maximum strength magnetic field. The second position of the second magnet rotor assembly in combination with the second position of the second magnet rotor assembly effectively completely shunts the magnetic field rendering no magnetic field. The first magnetic rotor assembly and the second magnetic rotor assembly move in unison under the control of a shunt motor. In other words if the orientation of the first magnet rotor assembly is rotated 45° then the orientation of the second magnet rotor assembly is rotated 45° in the same direction when viewed from the first end of the device. Preferably, a first and third rotor assembly reside proximate the first end of the conduit sensor device and a second and fourth rotor assembly reside proximate the second end of the conduit sensor device. The first and third rotor assemblies proximate the first end are rotated 90° such that the top portions thereof face each other at the conclusion of the 90° rotation canceling the magnetic field when the shunt shaft is rotated counter clockwise with respect to the first end. Similarly, the second and fourth rotor assemblies proximate the second end are rotated 90° such that the top portions thereof face away from each other at the conclusion of the 90° rotation canceling the magnetic field when the shunt shaft is rotated counter clockwise with respect to the first end.

The first magnet rotor assembly includes a first plurality of magnets axially arranged about a first axis, the first magnet rotor assembly includes a first top portion and a first bottom portion, and, the first top and bottom portions secure the first plurality of magnets within the first magnet rotor assembly. The second magnet rotor assembly includes a second plurality of magnets axially arranged about a second axis, the second magnet rotor assembly includes a second top portion and a second bottom portion, and, the second top and bottom portions secure the second plurality of magnets within the second magnet rotor assembly.

The first position of the first magnet rotor assembly orients the north pole of each of the first plurality of magnets radially outwardly. The first position of the second magnet rotor assembly orients the south pole of each of the second plurality of magnets radially outwardly. The second position of the first magnet rotor assembly orients the north pole of each of the first plurality of magnets at an angle of 90° with respect to the first position; and, the second position of the second magnet rotor assembly orients the north pole of each of the second plurality of magnets at an angle of 90° with respect to said first position. The direction of rotation depends on the direction of rotation of the shunt shaft with respect to the first end.

A worm drive is a gear arrangement in which a worm meshes with a worm wheel sometimes referred to as a worm gear. The terms "worm wheel" and "worm gear" are synonymous. The worm drives the worm wheel. The worm wheel is similar in appearance to a spur gear. A worm is essentially a gear in the form of a screw.

The conduit sensor device includes a first drive mechanism for rotating the first magnet rotor assembly from the first position to the second position and a second drive mechanism for rotating the second magnet rotor assembly from the first position to the second position. The first drive mechanism includes a first vertical shunt worm for rotating the first magnet rotor assembly. The second drive mechanism includes a second vertical shunt worm for rotating the second magnet rotor assembly. A shunt shaft extends between the first end portion of the device to the second end portion of the device. A first shunt shaft worm and a second shunt shaft worm are affixed to the shunt shaft. A first shunt worm wheel engages the first shunt shaft worm and a second shunt worm wheel engages the second shunt shaft worm. The first shunt worm wheel is engaged with the first vertical shunt worm wheel and is rotatable therewith. The second shunt worm wheel is engaged with the second vertical shunt worm wheel and is rotatable therewith.

A first helical gear is affixed to the first magnet rotor assembly. A second helical gear is affixed to the second magnet rotor assembly. The first helical gear is engaged with the first vertical shunt worm wheel and the second helical gear is engaged with the second vertical shunt worm wheel. The first magnet rotor assembly is rotatable with the first helical gear; and, the second magnet rotor assembly is rotatable with the second helical gear.

A third magnet rotor assembly residing proximate the first end portion of the device and rotatable between first and second positions is preferably used. A fourth magnet rotor assembly resides proximate the second end portion of the device and is rotatable between first and second positions is preferably used. The third magnet rotor assembly includes a third plurality of magnets axially arranged about a third axis. The third magnet rotor assembly includes a third top portion and a third bottom portion. The third top and bottom portions secure the third plurality of magnets within the third magnet rotor assembly. The fourth magnet rotor assembly includes a fourth plurality of magnets axially arranged about a fourth axis. The fourth magnet rotor assembly includes a fourth top portion and a fourth bottom portion. The fourth top and bottom portions secure the fourth plurality of magnets within the fourth magnet rotor assembly.

The first position of the third magnet rotor assembly orients the north pole of each of the third plurality of magnets radially outwardly. The first position of the fourth magnet rotor assembly orients the south pole of each of the fourth plurality of magnets radially outwardly. The second position of the third magnet rotor assembly orients the north pole of each of the third plurality of magnets at an angle of 90° with respect to the first position. The second position of the fourth magnet rotor assembly orients the north pole of each of the fourth plurality of magnets at an angle of 90° with respect to said first position. The direction of rotation of the first and third magnet rotor assemblies depends on the direction of rotation of the shunt shaft.

A third drive mechanism rotates the third magnet rotor assembly from the first position to the second position and a fourth drive mechanism rotates the fourth magnet rotor assembly from the first position to the second position. The third drive mechanism includes the first vertical shunt worm for rotating the third magnet rotor assembly; and, the fourth drive mechanism includes the second vertical shunt worm for rotating the fourth magnet rotor assembly.

A third helical gear is affixed to the third magnet rotor assembly. The fourth helical gear is affixed to the fourth magnet rotor assembly. The third helical gear is engaged with the first vertical shunt worm. The fourth helical gear is engaged with the second vertical shunt worm. The third magnet rotor assembly is rotatable with the third helical gear; and, the fourth magnet rotor assembly is rotatable with the fourth helical gear.

Another example of the conduit sensor device is disclosed which includes a first end of the device and a second end of the device. A first magnet rotor assembly, a third magnet rotor assembly, a third magnet rotor assembly, and a fourth magnet rotor assembly are disclosed. The first magnet rotor assembly and the second magnet rotor assembly reside at the first end of the device. The second magnet rotor assembly and the fourth magnet rotor assembly reside at the second end of the device. The first and third magnet rotor assemblies are rotationally movable in a range of positions between a first position and a second position at the first end of the device. The third and fourth magnet rotor assemblies are rotationally movable in a range of positions between a first position and a second position at the second end of the device. A magnetic shunt shaft includes first and second ends, the first end of the magnetic shunt shaft resides at the first end of the device and the second end of the magnetic shunt shaft resides at the second end of the device. A first gearbox resides at the first end of the device and a second gearbox resides at the second end of the device. A first worm is affixed to the first end of the magnetic shunt shaft and a second worm is affixed to the second end of the magnetic shunt shaft. The first gearbox includes: a first wheel worm; a first vertical worm affixed to the first wheel worm; a first helical gear, the first helical gear engages the first vertical worm; and, a third helical gear, the third helical gear engages the first vertical worm gear. The first magnet rotor assembly is affixed to the first helical gear and is rotatable therewith. The third magnet rotor assembly is affixed to the third helical gear and is rotatable therewith. The first worm is affixed to the first end of the magnetic shunt shaft and engages the first wheel worm and drives the first vertical worm affixed to the first wheel worm. The first vertical worm drives the first helical gear and the first magnet rotor assembly in a first rotational direction between first and second positions and the first vertical worm drives the third helical gear and the third magnet rotor assembly in a second rotational direction opposite to the first rotational direction of the first helical gear between first and second positions. The second gearbox includes: a second wheel worm; a second vertical worm affixed to the second wheel worm; a second helical gear, the second helical gear engages the second vertical worm; and, a fourth helical gear, the fourth helical gear engages the second vertical worm. The second magnet rotor assembly is affixed to the second helical gear and is rotatable therewith. The fourth magnet rotor assembly is affixed to the third helical gear and is rotatable therewith. The second worm affixed to the second end of the magnetic shunt shaft engages the second wheel worm and drives the second vertical worm affixed to the second wheel worm. The second vertical worm drives the second helical gear and the second magnet rotor assembly in a first rotational direction between the first and second positions and the second vertical worm drives the fourth helical gear and the fourth magnet rotor assembly in a second rotational direction opposite to the first rotational direction of the second helical gear between the first and second positions. When the first and third magnet rotor assemblies are in the first position and when the second and fourth magnet rotor assemblies are in the first position, a magnetic field of maximum strength is generated between the first and the second magnet rotor assemblies and the third and fourth magnetic rotor assemblies, and, the magnetic field of maximum strength extends into a conduit. When the first and third magnet rotor assemblies are in the second position and when the second and fourth magnet rotor assemblies are in the second position, no magnetic field exists between the first and second magnet rotor assemblies and no magnetic field exists between the third and fourth magnet rotor assemblies. When the first and second magnet rotor assemblies are in a rotational position intermediate the first and second positions, and when the third and fourth magnet rotor assemblies are in a rotational position intermediate the first and second positions, then the strength of the magnetic field between the first and second magnet rotor assemblies is modified according to the rotational positions of said first and second magnet rotor assemblies, and then the strength of the magnetic field between the third and fourth magnet rotor assemblies is modified according to the rotational positions of the second and fourth magnet rotor assemblies.

The first magnet rotor assembly includes a plurality of magnets and each one of the plurality of magnets includes a north pole and a south pole. The second magnet rotor assembly includes a plurality of magnets and each one of the plurality of magnets includes a north pole and a south pole. The third magnet rotor assembly includes a plurality of magnets and each one of the plurality of magnets includes a north pole and a south pole. The fourth magnet rotor assembly includes a plurality of magnets and each one of the plurality of magnets includes a north pole and a south pole. When the first and third magnet rotor assemblies are in the first position: the south poles of each of the plurality of magnets of the first magnet rotor assembly face downwardly away from the conduit and the north poles of each of the plurality of magnets of the first magnet rotor assembly face upwardly toward the conduit; and, the south poles of each of the plurality of magnets of the third magnet rotor assembly face downwardly away from the conduit and the north poles of each of the plurality of magnets of the third magnet rotor assembly face upwardly toward the conduit. When the second and fourth magnet rotor assemblies are in the first position: the south poles of each of the plurality of magnets of the second magnet rotor assembly face upwardly toward the conduit and the north poles of each of the plurality of magnets of the second magnet rotor assembly face downwardly away from the conduit; and, the south poles of each of the plurality of magnets of the fourth magnet rotor assembly face upwardly toward the conduit and the north poles of each of the plurality of magnets of the fourth magnet rotor assembly face downwardly away from the conduit.

BRIEF DESCRIPTION OF THE DRAWINGS

FIG. 3A is a schematic top view of the conduit sensor device with magnetic shunt.

FIG. 3B is a schematic side view of the conduit sensor device with magnetic shunt.

FIG. 3C is a schematic first end view of conduit sensor device with magnetic shunt.

FIG. 3D is a schematic second end view of conduit sensor device with magnetic shunt.

FIG. 3F is another schematic perspective view of the second backing bar weldment of the conduit sensor device with magnetic shunt.

FIG. 3G is a schematic end view of the second backing bar weldment of the conduit sensor device with magnetic shunt.

FIG. 7 is a schematic plan view of the magnet drive shaft, first end worm, spur gear affixed to shaft and second end worm.

FIG. 7A is a cross-sectional view taken along the lines 7A-7A of FIG. 7.

FIG. 7B is an enlargement of the first end portion of FIG. 7.

FIG. 7C is a cross-sectional enlargement of the first end portion of FIG. 7.

FIG. 7D is an enlargement of the second end portion of FIG. 7.

FIG. 7E is a cross-sectional enlargement of the second end portion of FIG. 7.

FIG. 8 is a schematic plan view of magnet drive shaft, first end worm, spur gear affixed to shaft and second end worm.

FIG. 8A is a cross-sectional view taken along the lines 8A-8A of FIG. 8.

FIG. 8B is an enlargement of the first end portion of FIG. 8.

FIG. 8C is a cross-sectional enlargement of the first end portion of FIG. 8.

FIG. 8D is an enlargement of the second end portion of FIG. 8.

FIG. 8E is a cross-sectional enlargement of the second end portion of FIG. 8.

FIG. 10 is a schematic cross-sectional view taken along the lines 10-10 of FIG. 3.

FIG. 10A is a schematic cross-sectional view taken along the lines 10-10 of FIG. 3 with the rotor assemblies of the second end rotated 90°.

FIG. 11 is a schematic cross-sectional view taken along the lines 11-11 of FIG. 3.

FIG. 11A is a schematic cross-sectional view taken along the lines 11-11 of FIG. 3 with the rotor assemblies of the first end rotated 90°.

DESCRIPTION OF THE INVENTION

Figure 1:
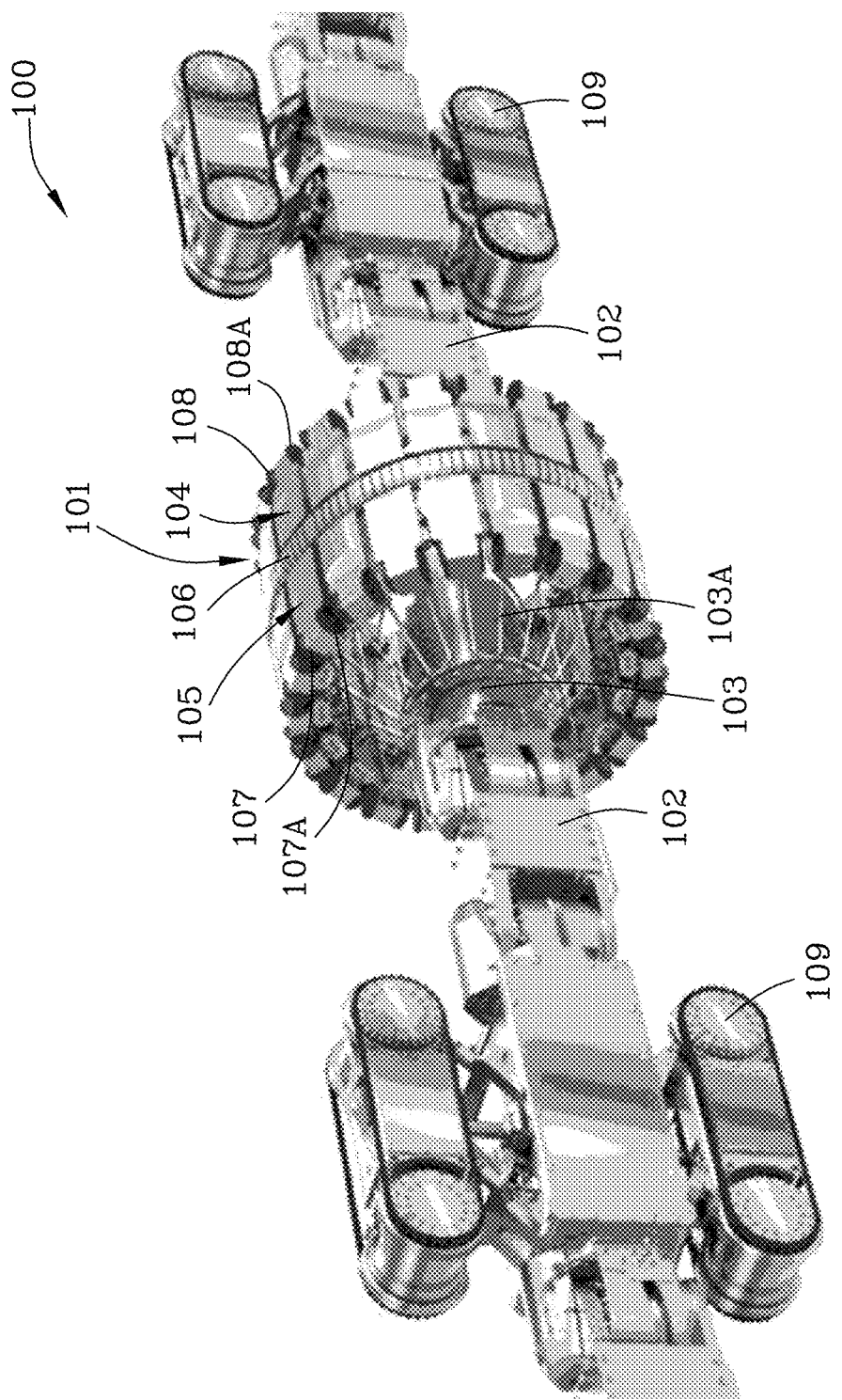
FIG. 1 is a schematic perspective view of a plurality of conduit sensor devices, and, each of the conduit sensor devices includes a plurality of sensors and magnetic shunts.

FIG. 1 is a schematic perspective view 100 of a plurality of conduit sensor devices 101, and, each of the conduit sensor devices 101 includes a plurality of sensors 106 and magnetic shunts. Arrow 101 is illustrated pointing to one conduit sensor with a magnetic shunt therein. Reference numeral 102 is used to denote couplings between the plurality of conduit sensors and battery powered drive units 109. A tubular radial control mechanism 103 controls wires/rods for extending the conduit sensors 101 radially outwardly and for contracting the conduit sensors radially inwardly. Arrow 104 indicates the second end of one conduit sensor with a magnetic shunt and arrow 105 indicates the first end of one conduit sensor with magnetic shunt. Arrow 106 indicates electronic sensors used to detect anomalies and defects in pipes and conduits. Reference numerals 107, 107A, 108, 108A denote rubber/synthetic propulsion wheels.

Figure 2:
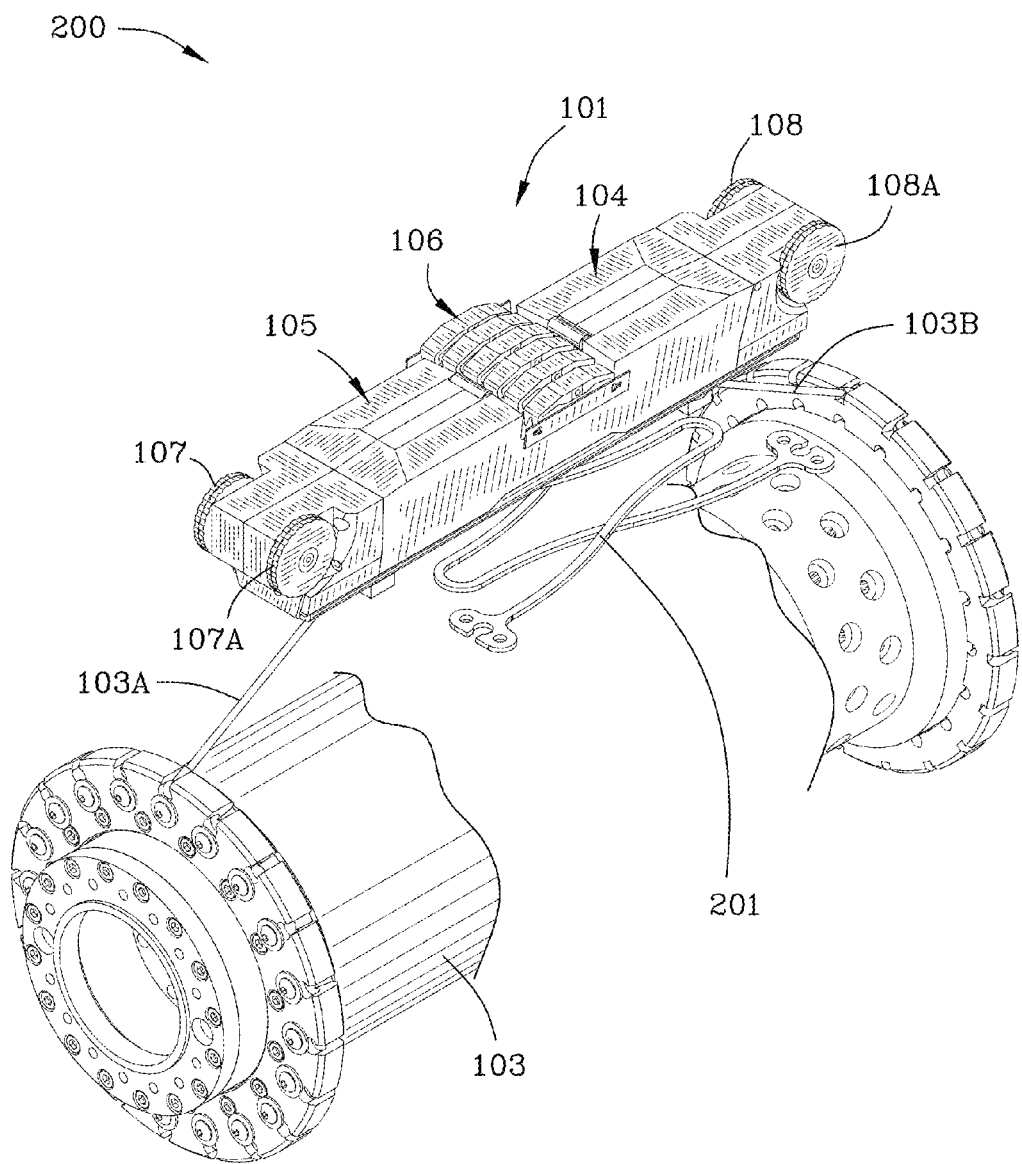
FIG. 2 is an enlargement of a portion of FIG. 1 illustrating the tubular radial control mechanism and a conduit sensor with magnetic shunt.

FIG. 2 is an enlargement 200 of a portion of FIG. 1 illustrating the tubular radial control mechanism 103 and a conduit sensor 101 with magnetic shunt. Also indicated is a spring 201 which is attached to the bottom of one of the conduit sensor devices 101. Each of the conduit sensor devices 101 has two springs 201 affixed thereto. These springs provide the force to open the assembly as shown in FIG. 2 when the radial control mechanism 103 commands the radial movement of the conduit sensor devices 101. Wires/rods 103A, 103B support one conduit sensor device 101 from the tubular radial control mechanism 103.

Figure 3:
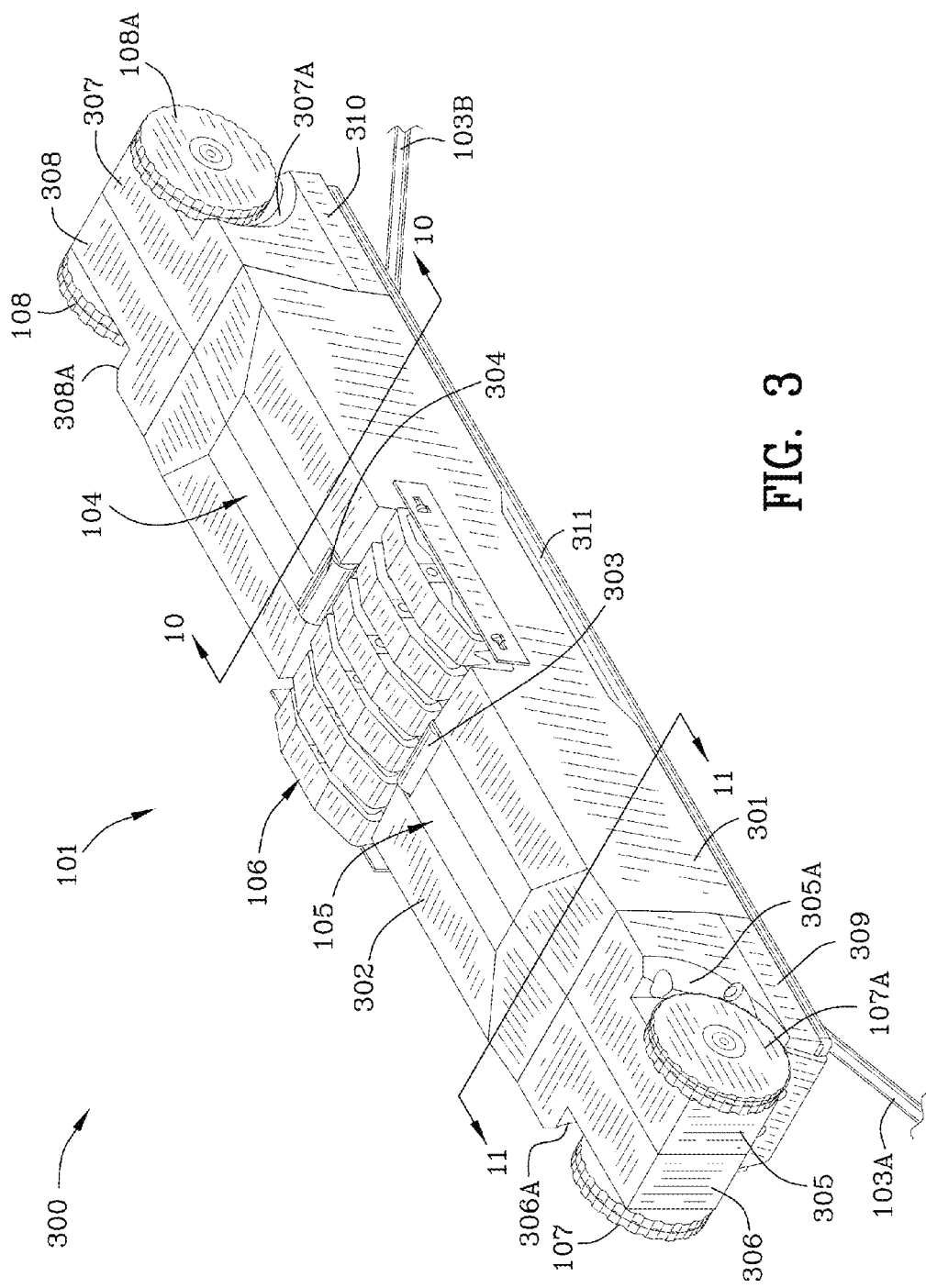
FIG. 3 is a schematic perspective view of one conduit sensor device with magnetic shunt.

FIG. 3 is a schematic perspective view 300 of the conduit sensor device 101 with magnetic shunt. Omitted from the drawings are numerous bolt holes some of which are threaded and some of which are simply passageways for the bolts. Also omitted from the drawings are numerous bolts which reside in the passageways and which interconnect the parts of the invention. In the central portion of the device, the first backing-bar weldment 301 and the second backing-bar weldment 302 are shown. First center roller, 303, and second center roller, 304, are illustrated in FIG. 3. Center rollers 303, 304 protect the conduit sensor device, and, more particularly, the sensors 106 from being damaged in the event that the device 101 is moved radially outwardly with too much force. Center rollers 303, 304 include pins (unnumbered) which are affixed in apertures such as aperture 321 illustrated in FIG. 3E. A recess 322 in the second backing bar weldment accommodates center roller 303. Flat surface 323 of second backing bar weldment 302 is the area in which the sensors 106 reside.

Figure 3E:
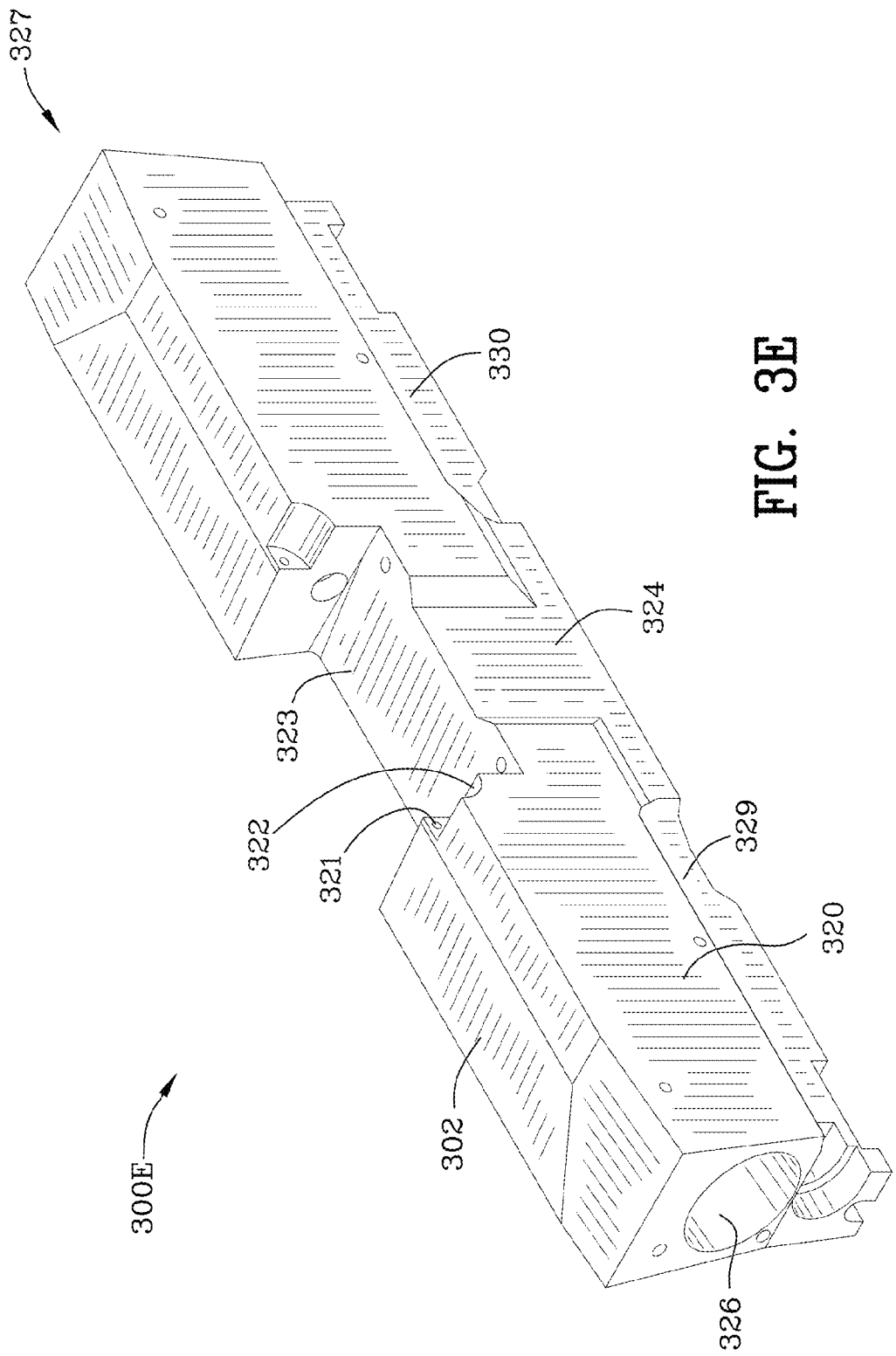
FIG. 3E is a schematic perspective view of the second backing bar weldment of the conduit sensor device with magnetic shunt.
Figure 6:
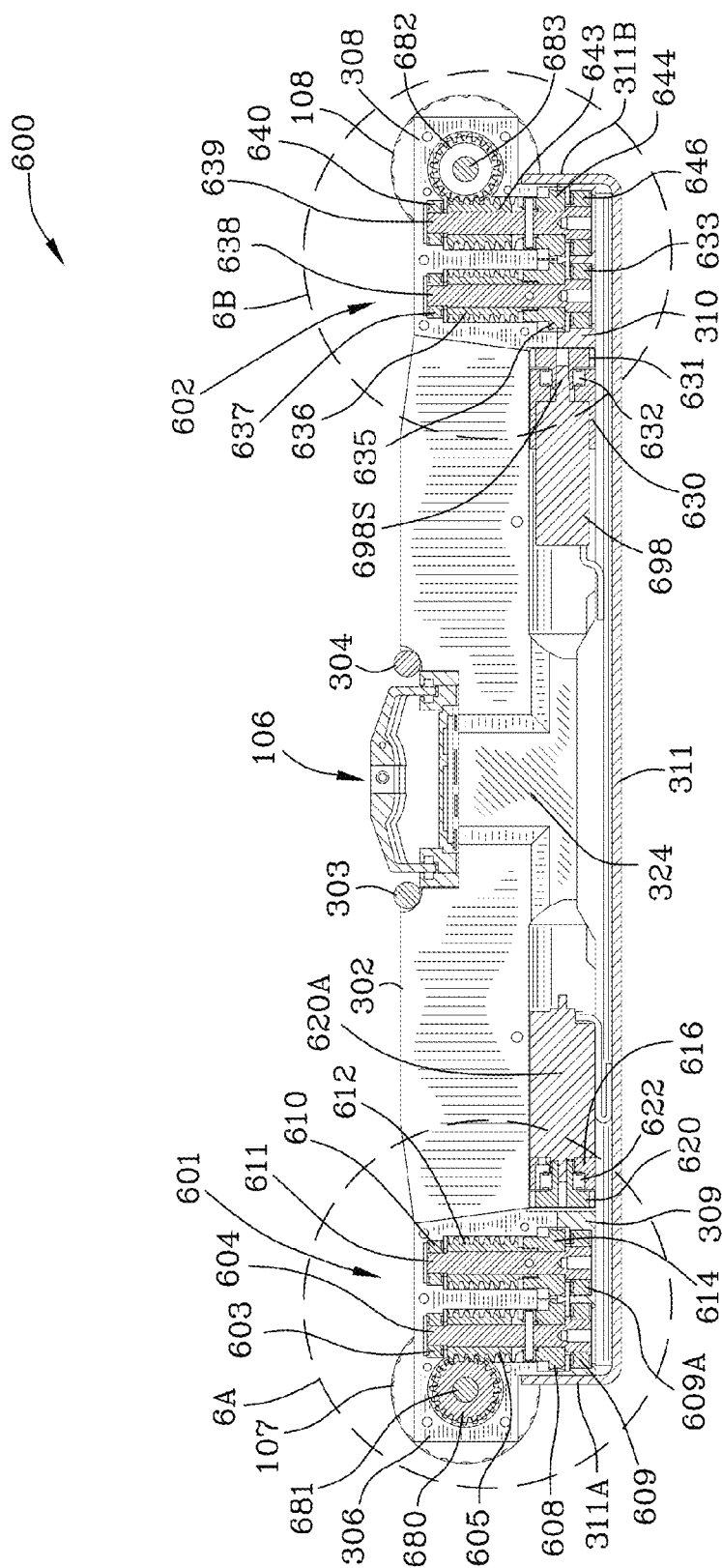
FIG. 6 is a cross-sectional schematic view taken along the line 6-6 of FIG. 3A.

FIG. 3E is a schematic perspective view 300E of the second backing bar weldment 302 of the conduit sensor with magnetic shunt. The magnetic shunt is not illustrated in FIG. 3E. Referring to FIG. 3E, flat interior face 320 of the second backing bar weldment 302 is illustrated. The first magnet rotor assembly 991 resides in housing 326 in the second backing-bar weldment. Slot 324 resides in face 320 and provides room for sensor wiring. First magnet rotor assembly 991 resides substantially at the first end of the device. Housing 326 is shown as a cylindrical aperture in the second backing bar weldment 302 in FIG. 3E. Arrow 327 is illustrated in FIG. 3E as pointing to another housing for second magnet rotor assembly 993. Second magnet rotor assembly 993 resides substantially at the second end of the device. Still referring to FIG. 3E, recess 329 provides space for the propulsion motor 620A as illustrated in FIG. 6. Recess 330 provides space for the shunt motor 698 as illustrated in FIG. 6. FIG. 6 is a schematic cross-sectional view 600 taken along the line 6-6 of FIG. 3A.

Referring to FIG. 3F, passageway 331 extends from the first end of the second backing bar weldment to the second end thereof and houses propulsion shaft 550 therein. First backing bar weldment 301 is reciprocally shaped with respect to second backing bar weldment 302. In other words, the first backing bar weldment 301 includes reciprocally shaped passageways and reciprocally shaped features described in connection with the second backing bar weldment 302. For instance, backing bar weldment 301 includes a flat interior face which abuts the flat interior face 320 of the second backing bar weldment 302. Similarly, the first backing bar weldment 301 includes a recess which is the reciprocal of recess 324 which allows room for wiring when mounted flushly with respect to the second backing bar weldment 302 and affixed to the second backing bar weldment 302. First backing bar weldment 301 includes a passageway for housing magnet drive shaft 401 and the passageway is reciprocal to passageway 331 (which houses propulsion shaft 550) and dimensionally the same as passageway 331. Further, the first backing bar weldment 301 includes reciprocally shaped recesses corresponding to recesses 329, 330 to permit space for the propulsion motor 620A and the shunt motor 698. Shunt motor 698 is supported by a motor support 630 viewed in FIGS. 6, 6B and 9. Motor support 630 is affixed to base plate 311. Also illustrated in FIG. 3E is a recessed surface 324 which allows space for wiring from the sensors 106 through the conduit sensor with magnetic shunt 101.

Figure 5:
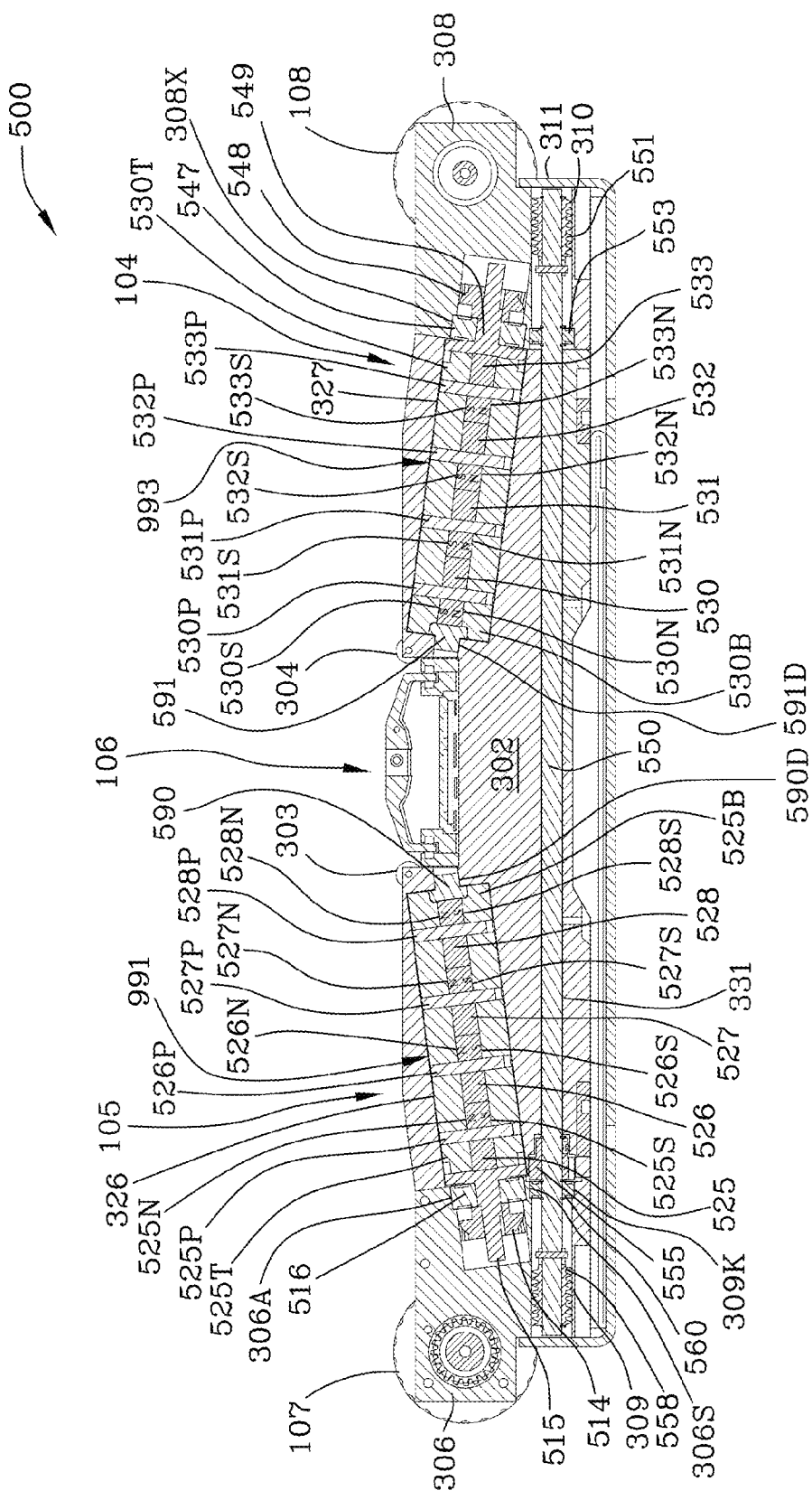
FIG. 5 is a cross-sectional schematic view taken along the lines 5-5 of FIG. 3A.
Figure 5A:
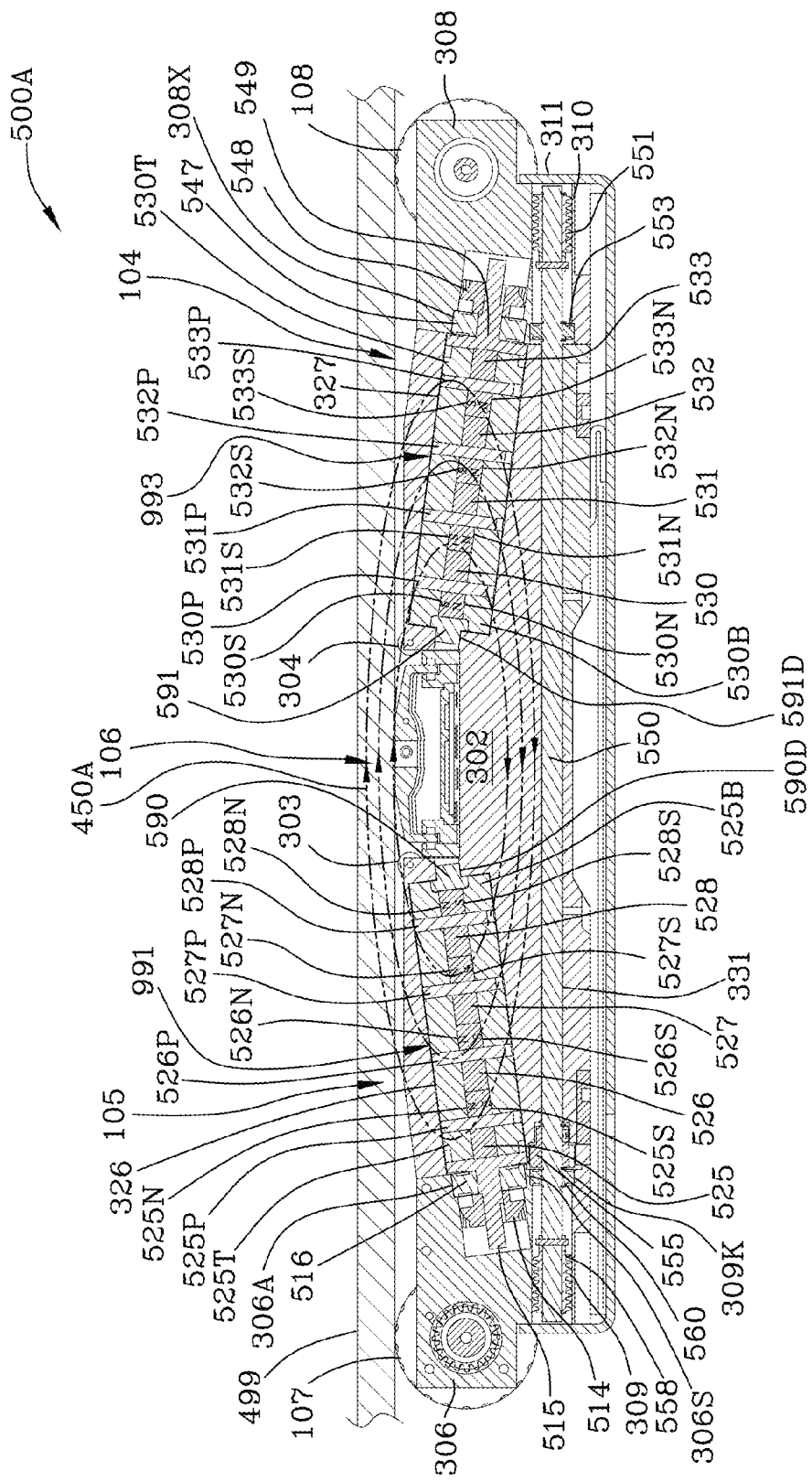
FIG. 5A is a cross-sectional schematic view taken along the lines 5-5 of FIG. 3A with a pipe in the view.
Figure 5B:
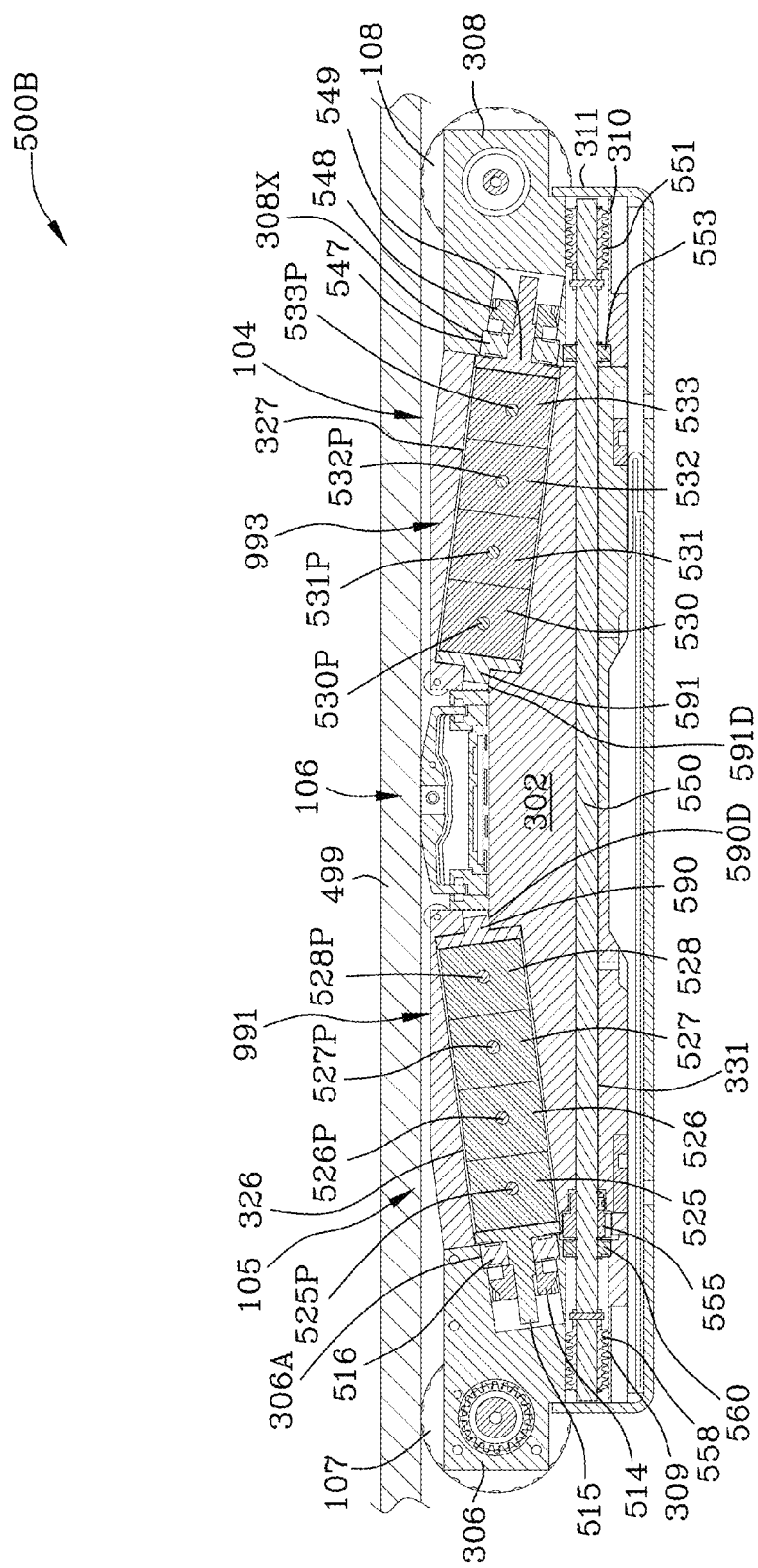
FIG. 5B is a cross-sectional schematic view taken along the lines 5-5 of FIG. 3A with rotor assemblies rotated 90°.

FIG. 3F is another schematic perspective view 300F of the second backing bar weldment 302 of the conduit sensor with magnetic shunt illustrating some of the features of the second backing bar weldment 302 in more detail. Recesses 329, 330 are illustrated well in FIG. 3F. Slot 328 is illustrated but performs no function, the same being a remnant of the process of manufacturing the second backing bar weldment. FIG. 3G is an end view 300G of the second backing bar weldment 302 of the conduit sensor 101 with magnetic shunt illustrating cylindrical housing 326 in the second backing bar weldment 302 and passageway 331. Cylindrically shaped housing 326 terminates in an end surface 326E. A circular opening 326C resides in end surface 326E and supports the rotor end 590 as illustrated in FIGS. 5, 5A and 5B. Cylindrically shaped housing 326 is typical of cylindrically shaped housing 327 illustrated in FIGS. 5, 5A and 5B and is typical of cylindrically shaped housings 426, 427 in the first backing bar weldment 301. Passageway 331 extends through the second backing bar weldment 302 and houses the propulsion shaft 550 as illustrated in FIGS. 5, 5A, 5B, 10 and 10A.

Referring back to FIG. 3, first end gear box half 305 and first end gear box half 306 are illustrated in FIG. 3 and combine to form the first end gear box which is fixed to the first and second backing bar weldments 301, 302. Gear box half 306 is fixed to gear box half 305, second backing-bar weldment 302 and end plate 309. In the same way, gear box 305 is fixed to gear box half 306, first backing-bar weldment 301 and end plate 309.

Referring still to FIG. 3, second end gear box half 307 and second end gear box half 308 combine to form the second end gear box which is fixed to the second end. Gear box half 308 is fixed to gear box half 307, second backing-bar weldment 302 and end plate 310. In the same way, gear box 308 is fixed to gear box 307, first backing-bar weldment 301 and end plate 310. Still additionally, first backing-bar weldment 301 and second backing-bar weldment 302 are fixed together.

Wheel wells 305A, 306A, 307A, 308A are illustrated in FIG. 3 and provide room for wheels 107, 107A, 108, 108A to rotate. First end bottom plate 309, second end bottom plate 310, and base plate 311 are illustrated in FIG. 3. Base plate 311 extends from the first end 105 to the second end 104 and wraps around the end plates 309, 310. First end gear box, 305, 306, and, second end gear box 307, 308 are affixed to base plate 311.

FIG. 3A is a schematic top view 300A of the conduit sensor device with magnetic shunt 101. FIG. 3B is a schematic side view 300B of the conduit sensor with magnetic shunt. Base plate 311 includes a first end portion 311A which wraps around the first end bottom plate 309. Base plate 311A also includes a second end portion 311B which wraps around the second end bottom plate 310.

Figure 3H:
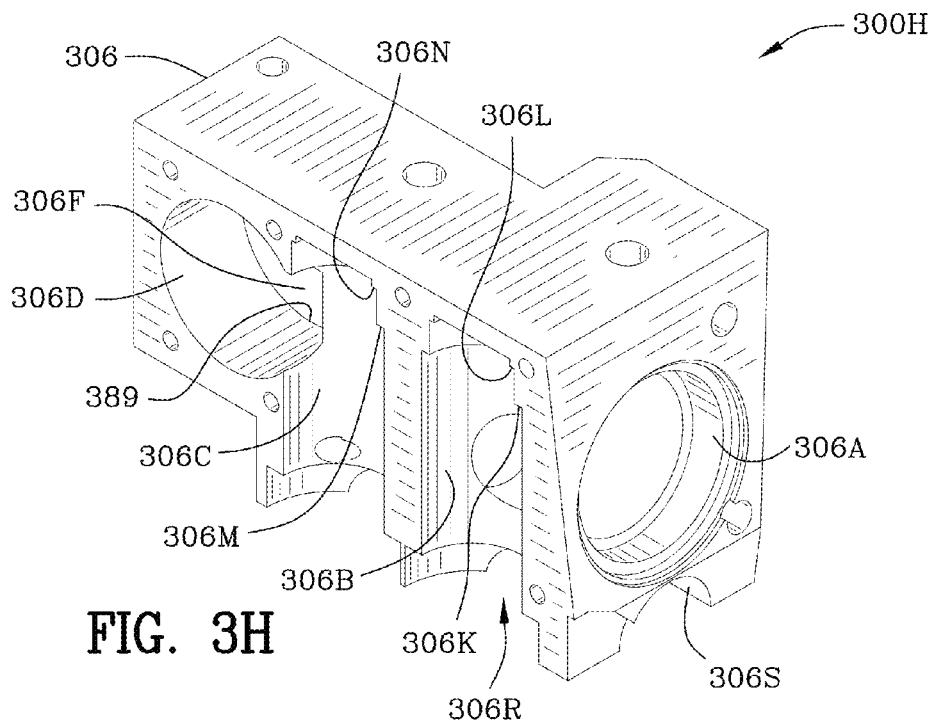
FIG. 3H is a schematic perspective view of the second half of the gear box of the first end of the conduit sensor device with magnetic shunt.
Figure 3I:
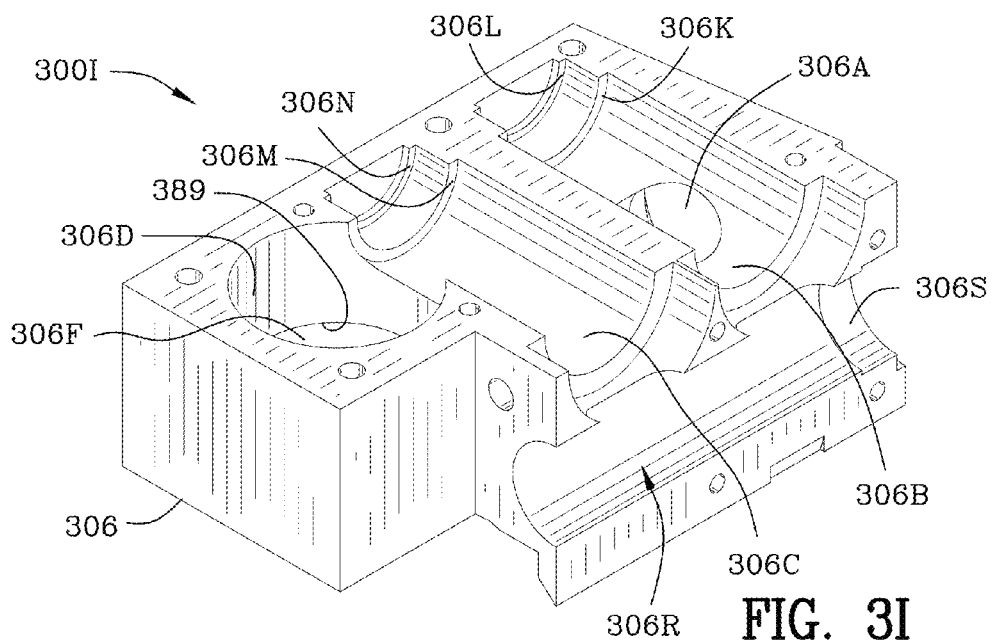
FIG. 3I is another schematic perspective view of the second half of the gear box of the first end of the conduit sensor device with magnetic shunt.

FIG. 3C is a schematic first end view 300C of the conduit sensor with magnetic shunt. First end access port 340 in end 311A of base plate 311 allows adjustment of a thrust bearing for the magnet drive shaft. FIG. 3D is a schematic second end view 300D of conduit sensor with magnetic shunt. Second end access port 341 in end 311B of base plate 311 allows adjustment of a thrust bearing for the magnet drive shaft (shunt shaft) 401. FIG. 3H is a schematic perspective view 300H of the first end gear box half 306 of the conduit sensor with magnetic shunt illustrating bearing well 306A, semi-circular shunt gear housing 306B, semi-circular drive gear housing 306C, and bearing well 306D. Bearing well 306A houses bearing 516. See FIGS. 5 and 5A.

Figure 3J:
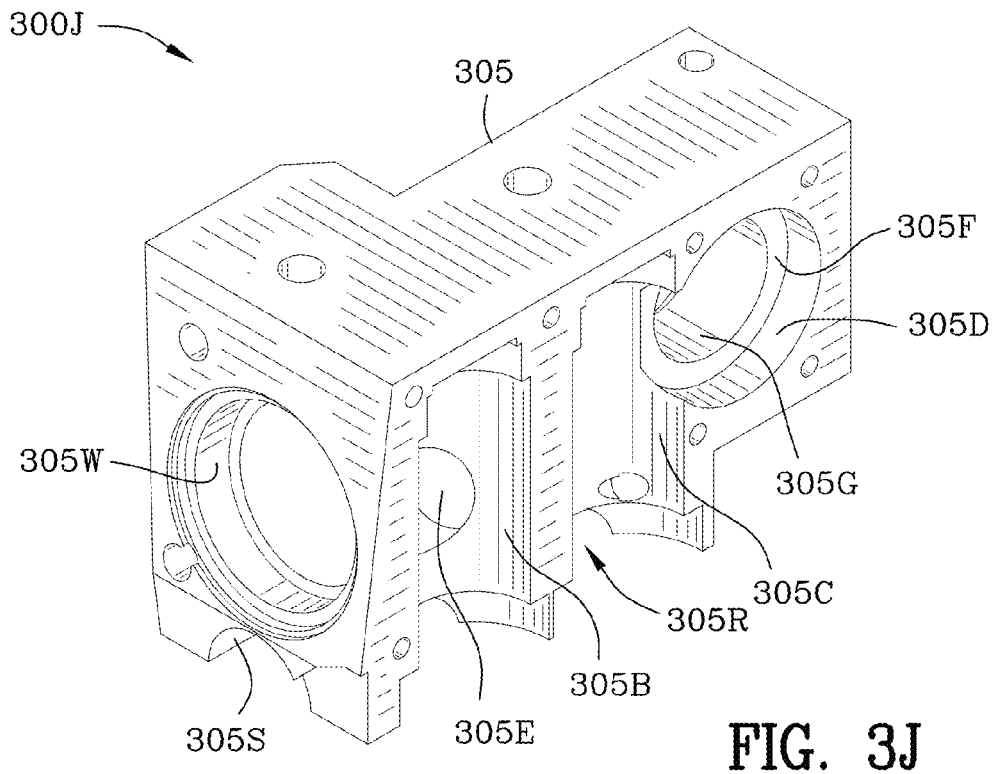
FIG. 3J is a schematic perspective view of the first half of the gear box of the first end of the conduit sensor device with magnetic shunt.
Figure 3K:
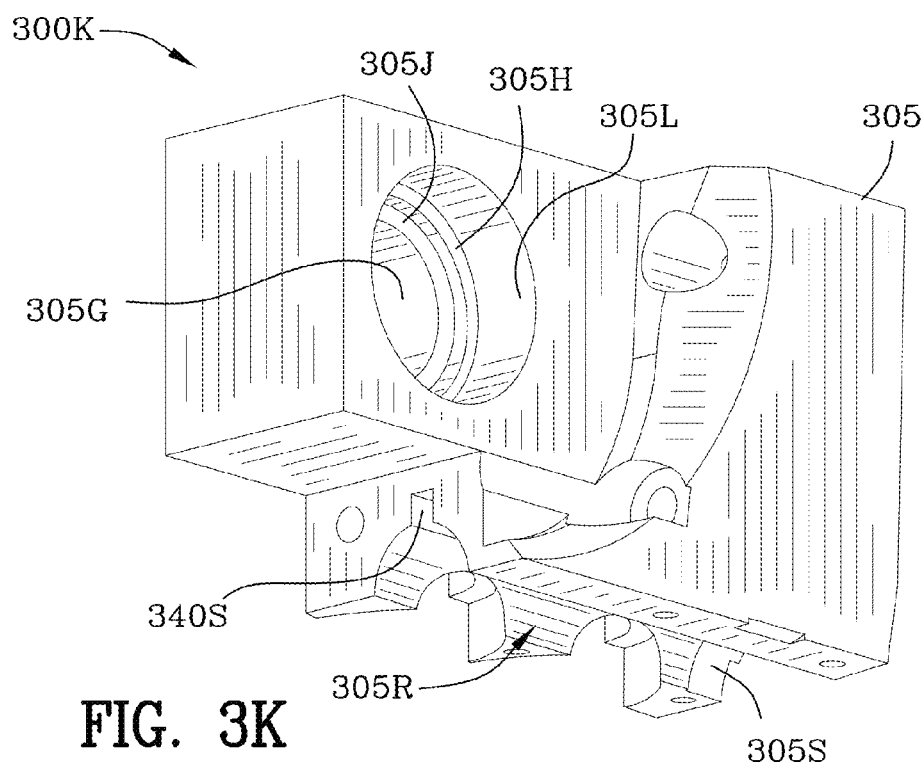
FIG. 3K is a schematic perspective view of the first half of the gear box of the first end of the conduit sensor device with magnetic shunt.

Referring to FIG. 3H, reference numeral 389 indicates a shoulder against which bearing 901 resides. See FIG. 9 wherein shaft bearings 901 and 902 are illustrated. Upper shoulder 306K in the semi-circular shunt gear housing 306, limits upper movement of vertical shunt worm 612. The shoulders 306K, 306L, 306M, 306N in gear box half 306 meet adjacent corresponding unnumbered shoulders in gear box half 305 illustrated in FIG. 3J. FIG. 3J is a schematic perspective view 300J of the first end gear box half 305 of the first end of the conduit sensor device with magnetic shunt. FIG. 3J illustrates the semi-cylindrical shunt gear housing 305B and semi-cylindrical drive gear housing 305C. Housings 306B, 305B reside adjacent each other and define the shunt worm 612 housing. Housings 306C, 305C reside adjacent each other and define propulsion worm 605 housings. Slot 305S supports bearing 416 which supports worm 402 mounted on shaft 401. Shoulder 305F defines the opening 305D in which drive gear 680 resides. FIG. 3K is a schematic perspective view 300K of the first half 305 of the gear box of the first end of the conduit sensor device with magnetic shunt. Shoulder 305H defines seat 305L in which drive shaft bearing 902 resides. See FIGS. 9 and 9C. Shoulder 305J defines another diameter in the first half of gear box 305 and reference numeral 305W is the bearing well for bearing 412. See FIGS. 4 and 4A. Reference numeral 305E indicates the end of the opening which begins with bearing well 305A. Reference numeral 305 indicates the passageway for the wheel drive shaft. Reference numeral 305R indicates the opening for shunt shaft 401 and worm 402 in gear box half 305.

Referring to FIGS. 3K, 4, 4A, 7, 7A, 7B, 7C, 7F and 7G, vertical slot 340S receives pin 415S of partial cylinder 402C and prevents rotation of the partial cylinder 402C with respect to the first half 305 of the gear box. It is necessary to restrain rotation of the partial cylinder 402C so as to enable adjustment of thrust bearing 402B.

FIGS. 7A and 7C illustrate the partial cylinder 402C in cross-section. Magnet drive shaft 401 includes an end portion 401F which engages thrust bearing 402B. Bearing 402B is threadably adjusted as threaded stud 402N is turned by a suitable tool such as a screw drive or hex headed wrench which mates with grip 402G of the threaded stud 402N. Threaded stud 402N includes a curved surface 419C which engages bearing 402B. Partial cylinder 402C includes a stepped bore 402R therethrough. Bore 402R has a relatively larger diametrical section which houses thrust bearing 402B. Bore 402R also includes a relatively smaller diametrical threaded section 402T which interengages threaded stud 402N.

FIGS. 7A and 7E illustrate the partial cylinder 403C in cross-section. Magnet drive shaft 401 includes an end portion 401S which engages thrust bearing 402B. Bearing 402B is threadably adjusted as threaded stud 403N is turned by a suitable tool such as a screw drive or hex headed wrench which mates with grip 403G of the threaded stud 403N. Threaded stud 403N includes a curved surface 420C which engages bearing 403B. Partial cylinder 403C includes a stepped bore 403R therethrough. Bore 403R has a relatively larger diametrical section which houses thrust bearing 403B. Bore 403R also includes a relatively smaller diametrical threaded section 403T which interengages threaded stud 403N.

Figure 7G:
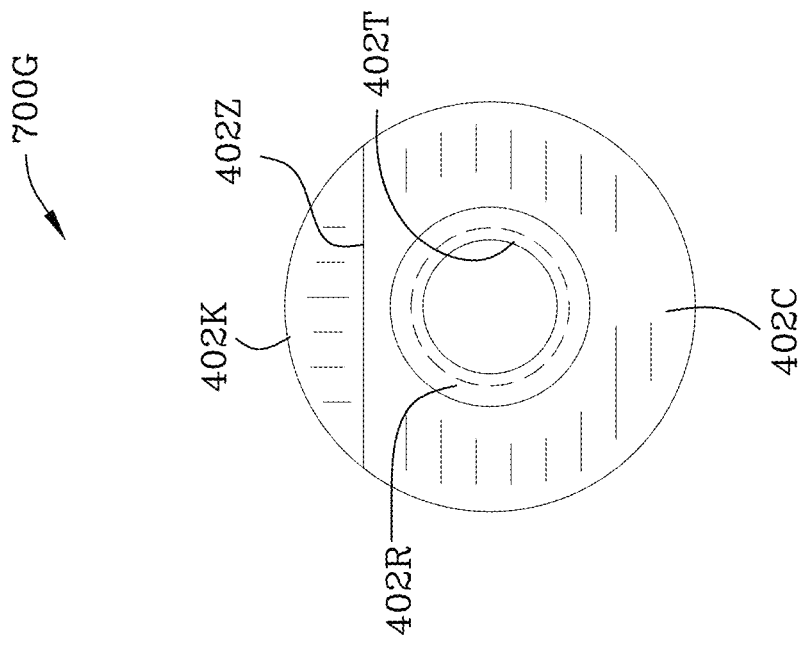
FIG. 7G is an end view of the partial cylinder which provides thrust bearing support for the magnet drive shaft.
Figure 7F:
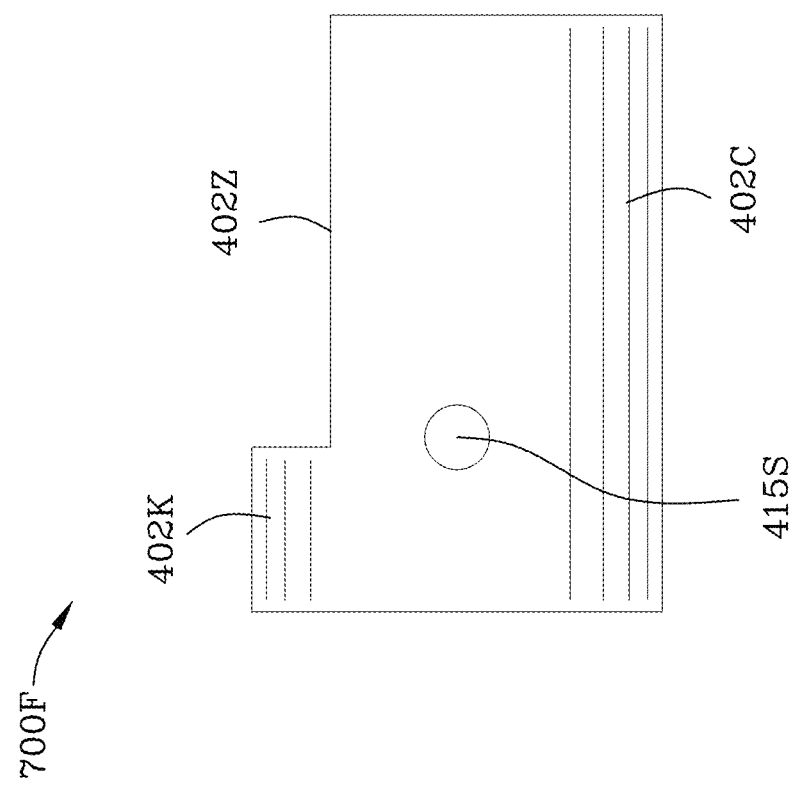
FIG. 7F is a top view of partial cylinder which provides thrust bearing support for the magnet drive shaft.
Figure 9:
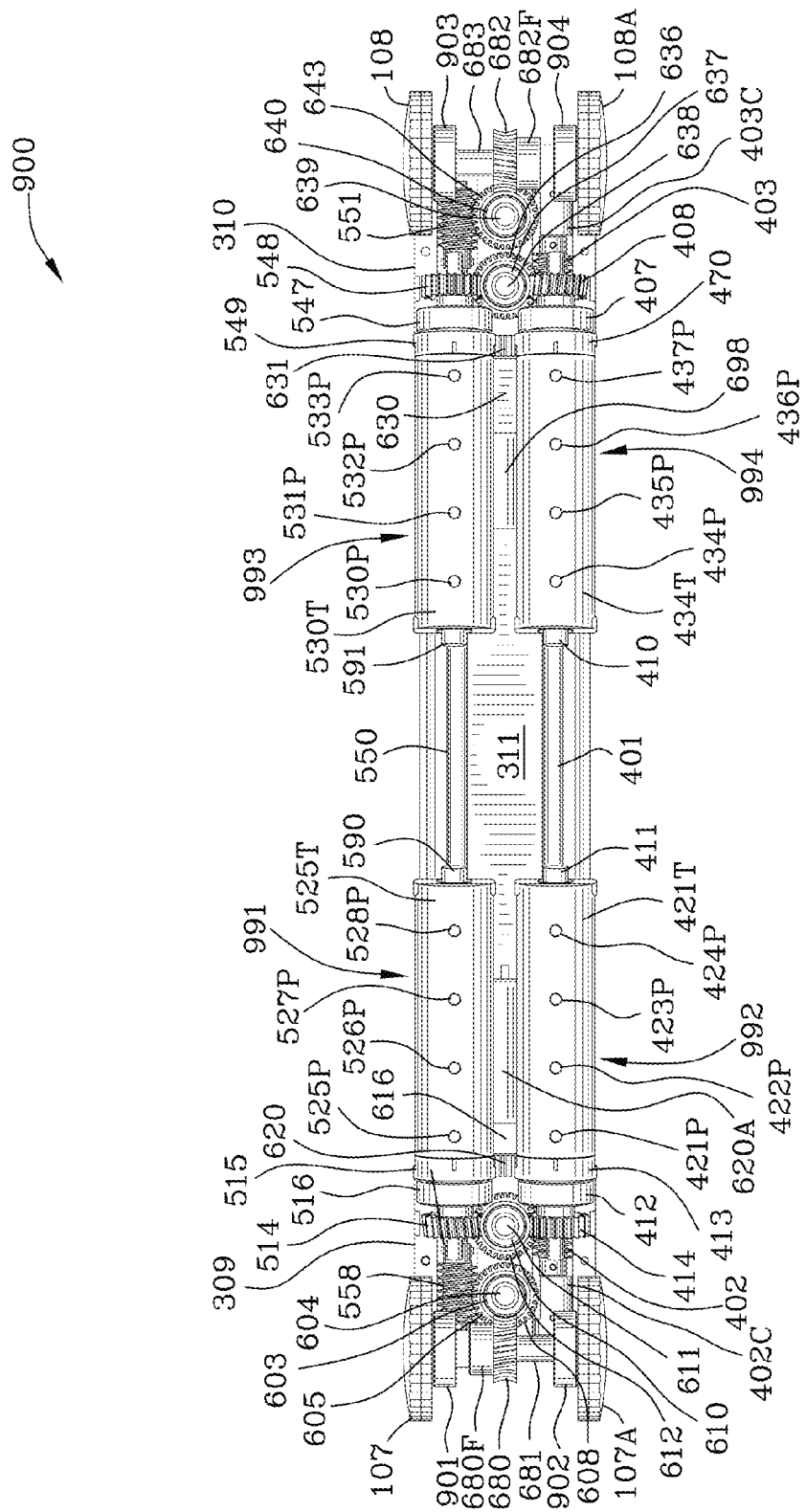
FIG. 9 is a schematic top view of the conduit sensor with magnetic shunt with the backing bar weldments and the gear boxes removed illustrating the first magnet rotor assembly, second magnet rotor assembly, third magnet rotor assembly and fourth magnet rotor assembly.
Figure 9A:
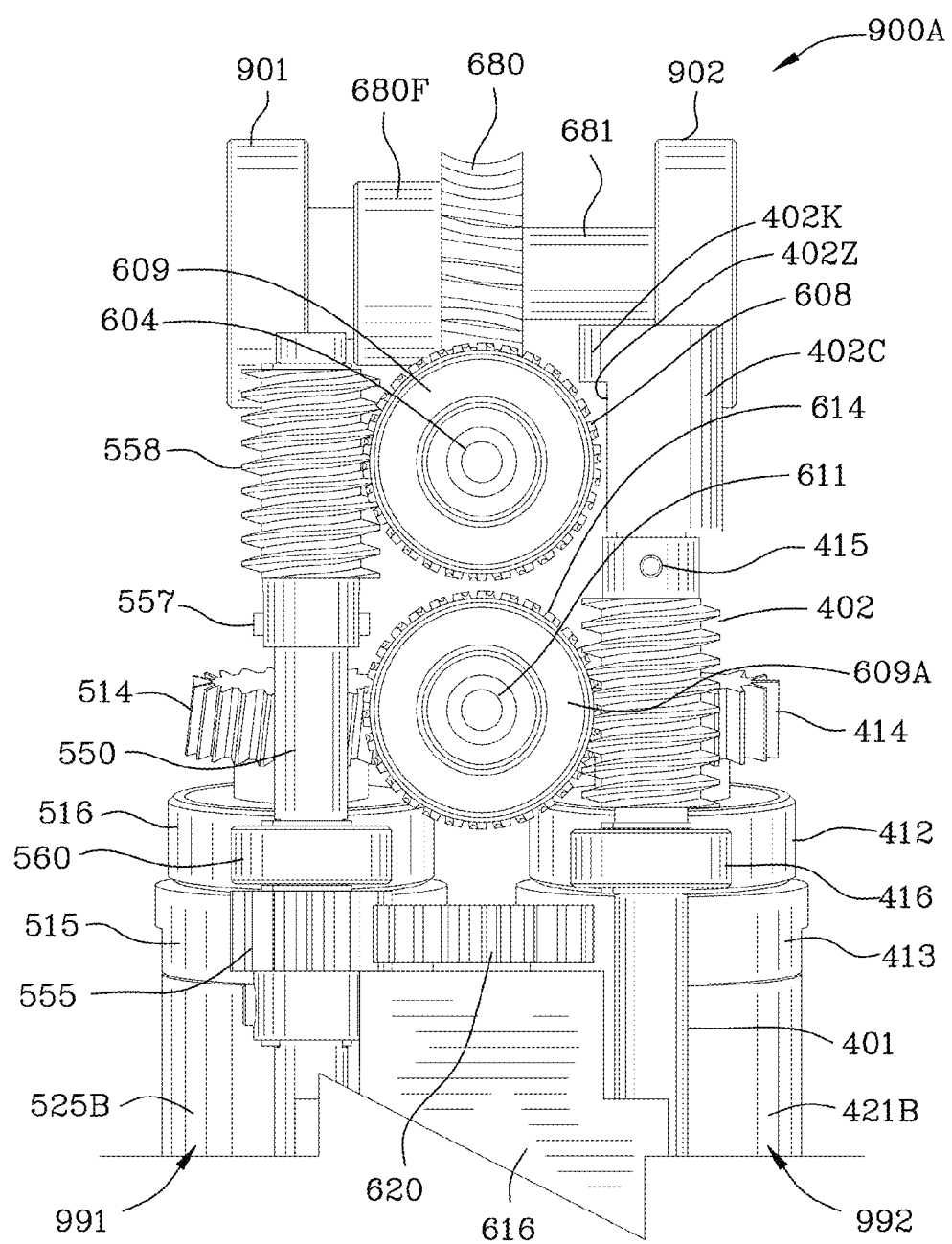
FIG. 9A is a schematic bottom view of the first end of FIG. 9.

FIG. 7F is a top view 700 F of partial cylinder 402C which provides thrust bearing support for the magnet drive shaft 401. FIG. 7G is an end view 700G of the partial cylinder 402C which provides thrust bearing support for the magnet drive shaft. Partial cylinder 403C has identical characteristics and, as such, is not separately described. Surface 402Z is flat and provides room for gear 608 as illustrated in FIGS. 9 and 9A. Also see FIGS. 7B and 7D. FIG. 7D illustrates the partial cylinder 403C and flat surface 403Z.

FIG. 9 is a schematic top view 900 of the conduit sensor with magnetic shunt with the backing bar weldments and the gear boxes removed illustrating the first magnet rotor assembly, second magnet rotor assembly, third magnet rotor assembly and fourth magnet rotor assembly. FIG. 9A is a schematic bottom view 900A of the first end of FIG. 9.

Figure 4:
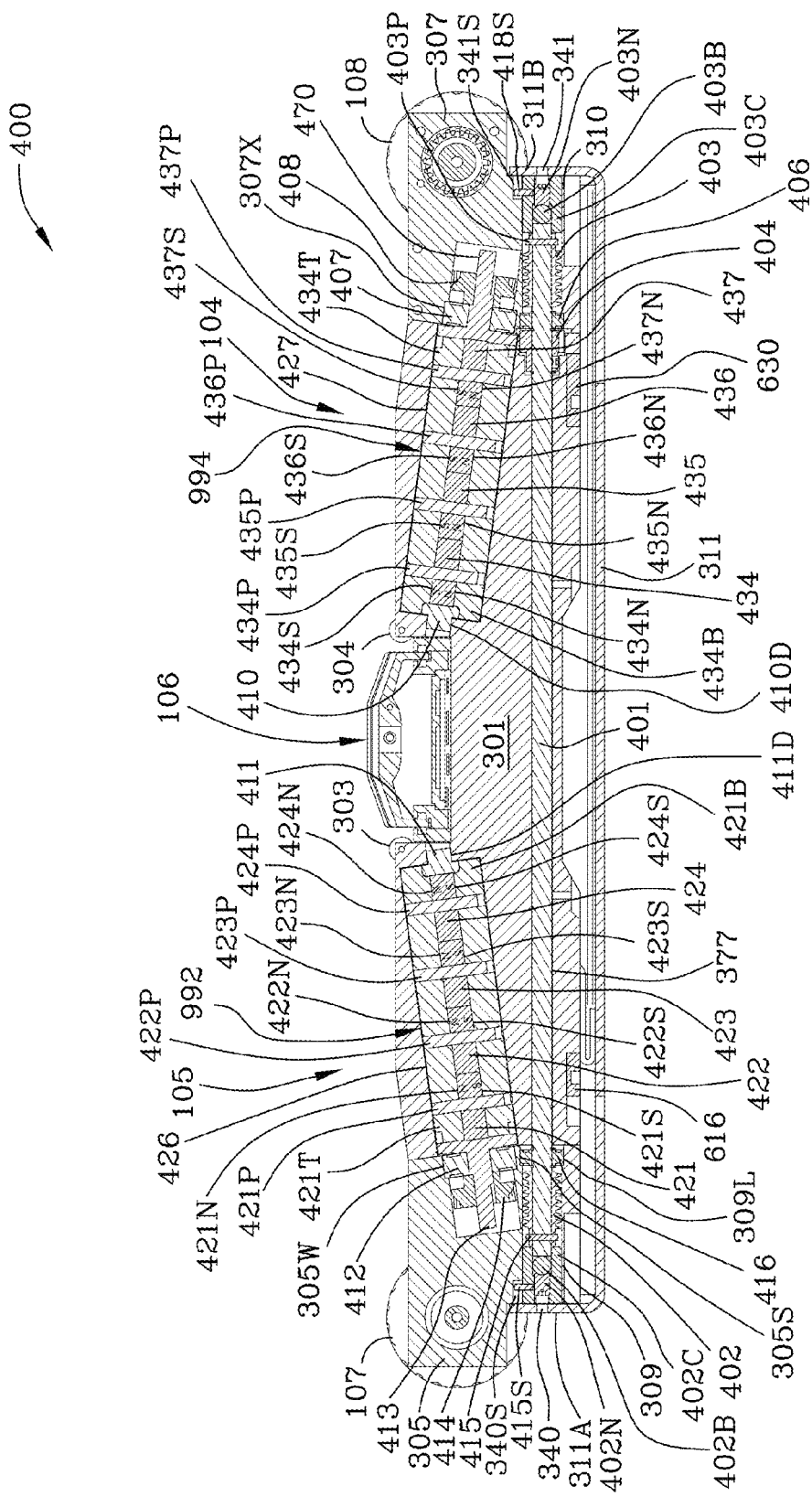
FIG. 4 is cross-sectional schematic view taken along the line 4-4 of FIG. 3A.

Referring to FIGS. 3C, 3D, and 4, access ports 340, 341 enable adjustment of the partial cylinders 402, 403 by rotating threaded studs, 402N, 403N clockwise in bores 402T, 403T forcing the partial cylinders outwardly into engagement with the ends 311A, 311B. The threaded studs 402N, 403N may be adjusted at the same time so that approximately the same amount of adjustment may occur on the first and second ends of magnet drive shaft 401. In other words, given the intermeshing of worms 402, 403 with their respective worm wheels 614, 635 and given the meshing of the shaft mounted gear 404 with the motor drive gear 631, the shaft 401 must be positionally supported equally from both the first and second ends. Loctite may be used to secure the threaded connection against vibration. Alternatively, if left handed threaded are used in the bores and on the adjusting threaded nuts, the adjustment may be made by turning the threaded studs counterclockwise. Pin 415S is guided in vertical slot 340S and prohibits rotation of partial cylinder 402C so that it may be adjusted into engagement with end 311A of the base plate 311. At the second end of the device, pin 418S is guided in vertical slot 341S prohibiting rotation of partial cylinder 403C so that it may be adjusted into engagement with end 311B of base plate 311.

Figure 6A:
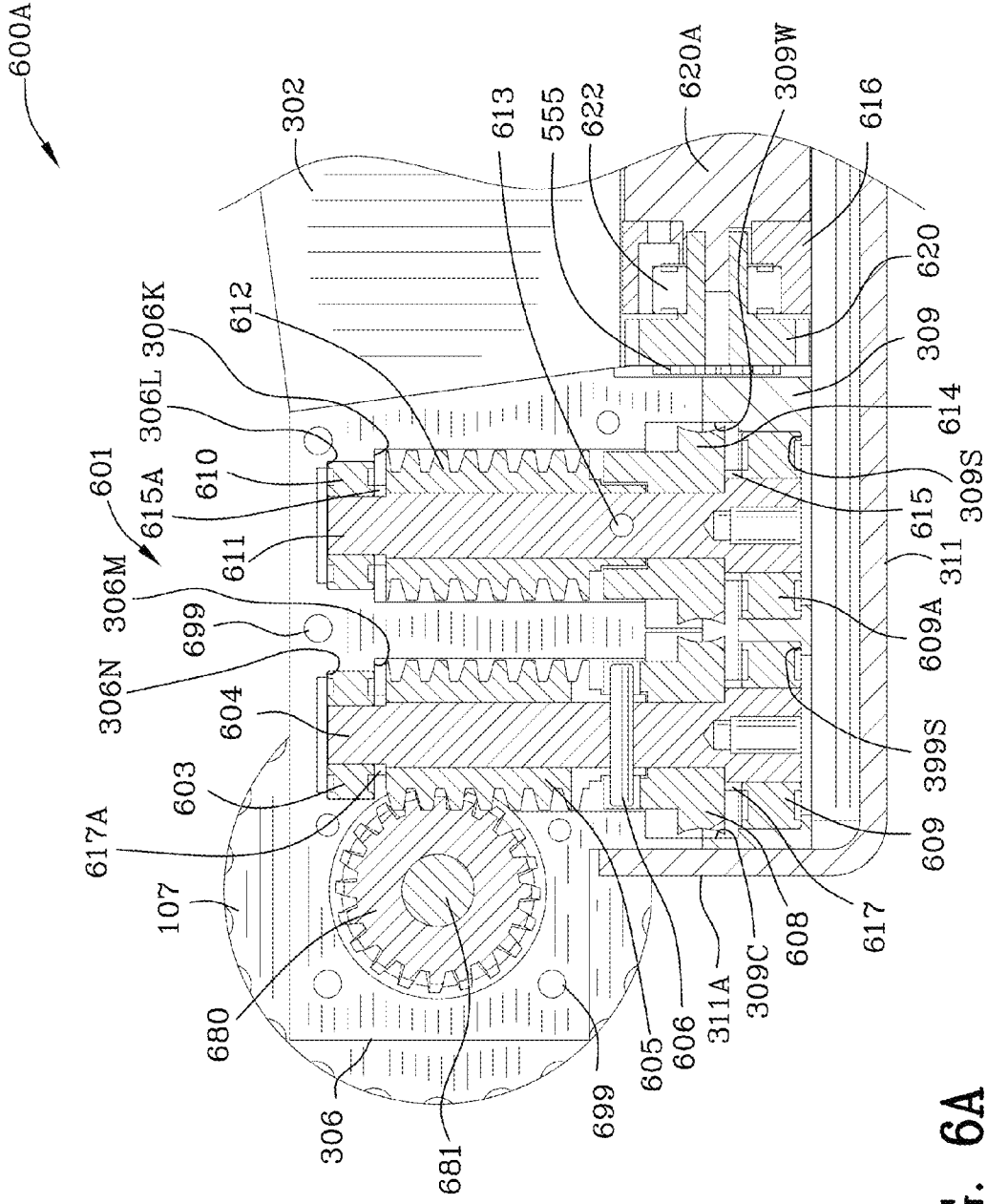
FIG. 6A is an enlargement of a portion of FIG. 6.

Referring to FIGS. 3H, 3I, 6, and 6A, bearing seat 306L supports upper bearing 610 for shunt shaft 611 and shunt worm drive 612. Upper bearing 610 supports drive shaft 611. Vertical shunt worm 612 is affixed to drive shaft 611 by pin 613 as illustrated in FIG. 6A. Vertical shunt worm 612 and vertical drive worm 614 include slots therein as best viewed in FIG. 6A. FIG. 6 is a schematic cross-sectional view 600 taken along the line 6-6 of FIG. 3A. FIG. 6A is an enlargement 600A of the first end portion 601 of the conduit sensor and magnetic shunt device. Vertical shunt worm 612 is restrained by shoulder 306K against upward movement.

Figure 4A:
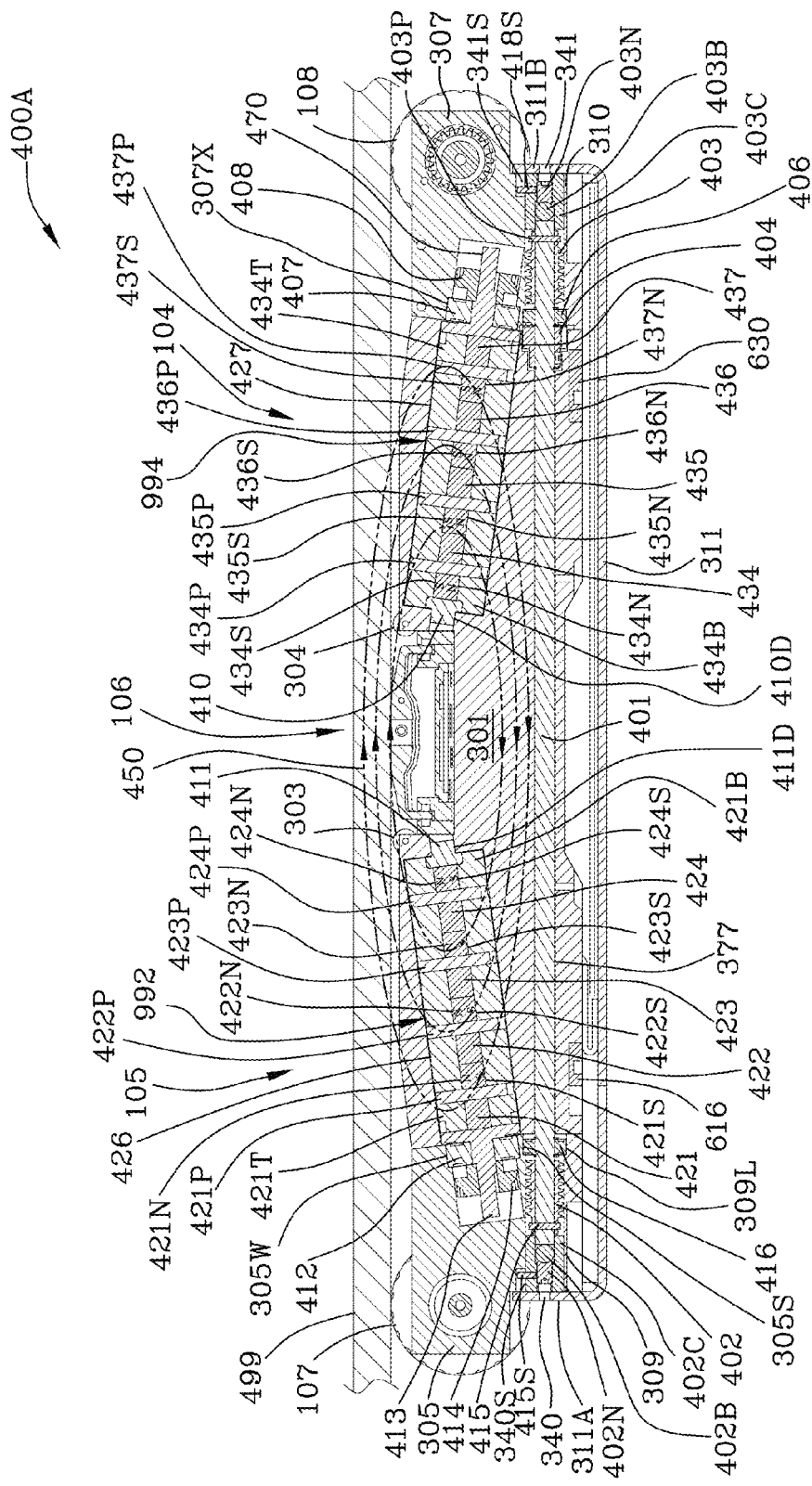
FIG. 4A is a cross-sectional schematic view taken along the line 4-4 of FIG. 3A.

Referring to FIG. 6A, bearing 609A is supported by shoulder 309S of bottom plate 309. Similarly, bearing 609 is supported by shoulder 399S of bottom plate 309. Spacer 615 resides between bearing 609A and shunt worm wheel 614. Spacer 615A resides between vertical shunt worm 612 and upper bearing 610. Shunt worm wheel 614 is driven by shaft driven worm 402 as illustrated in FIGS. 4 and 4A. Worm wheel 614, drive shaft 611, and vertical shunt worm 612 are affixed to each other by pin 613 and, thus, all three components 614, 611, 612 rotate together.

Referring to FIG. 6A, spacer 617 resides between bearing 609 and drive worm wheel 608. Spacer 617A resides between vertical drive worm 605 and upper bearing 603. Drive worm wheel 608 is driven by shaft driven worm 558 as illustrated in FIGS. 5, 5A, 9, 9A, and 9C. Worm wheel 608, vertical drive shaft 604, and vertical shunt drive 605 are affixed to each other by pin 606 and, thus, all three components 608, 604, 605 rotate together.

Referring to FIGS. 5A and 6A, propulsion motor 620A drives output shaft gear 620 which, in turn, drives spur gear 555 mounted on the propulsion drive shaft 555. Worm 558 is affixed to propulsion drive shaft 550 and rotates therewith. Worm wheel 558 is affixed to propulsion drive shaft 550 and as drive shaft 550 rotates, worm wheel 558 rotates, drive worm wheel 608 rotates, and, vertical drive worm 605 rotates driving helical gear 680. Rotation of helical gear 680 by drive worm 605 causes rotation of wheels 107, 107A which propel the conduit sensor device 101. Operation of the propulsion drive system is explained in greater detail hereinbelow.

Figure 6B:
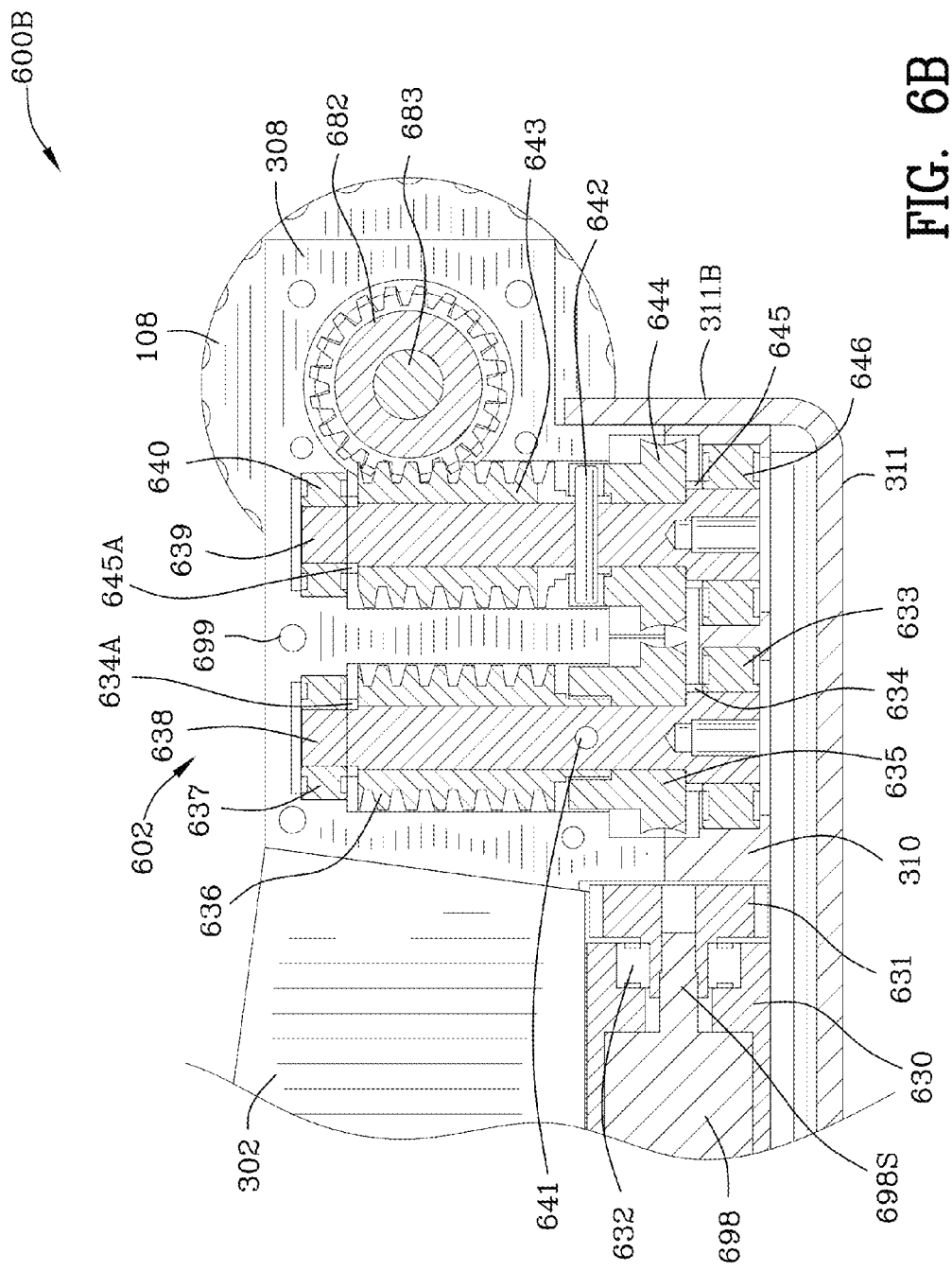
FIG. 6B is an enlargement of a portion of FIG. 6.

Referring to FIGS. 6B and 5A, shaft 550 also drives worm wheel 551 located at the second end of the device. As drive shaft 550 rotates, worm wheel 551 rotates, drive worm wheel 644 rotates, and vertical worm 643 rotates driving helical gear 682. Rotation of helical gear 682 by vertical drive worm 643 causes rotation of wheels 108, 108A which propel the conduit service device 101.

FIG. 9 is a schematic top view 900 of the conduit sensor device with backing bar weldments 301, 302 and the gear boxes removed 305, 306, 307, 308. Helical gears 414, 514 are viewed in FIGS. 9 and 9C. The top view is taken from the direction of the pipe (not shown in FIG. 9) radially inwardly. Magnet rotor assemblies 991, 992, 993, 994 are illustrated without the backing bar weldments 301, 302 which house the magnet rotor assemblies. Backing bar weldments 301, 302 are magnetically conductive enabling the magnetic field to pass freely therethrough depending on the orientation of the magnets of the magnet rotor assemblies. The first end of the conduit sensor device is the left end when viewing FIGS. 9, 9A and 9C, the first end having magnet rotor assemblies 991, 992 and the gearing system 402, 414, 514, 555, 558, 605, 608, 612, 614, 620, 680 proximate those rotor assemblies. See FIG. 9A, a schematic bottom view of the first end of FIG. 9, to view the propulsion motor output gear 620A and the propulsion shaft 550 with spur gear 555 mounted thereto.

Figure 9B:
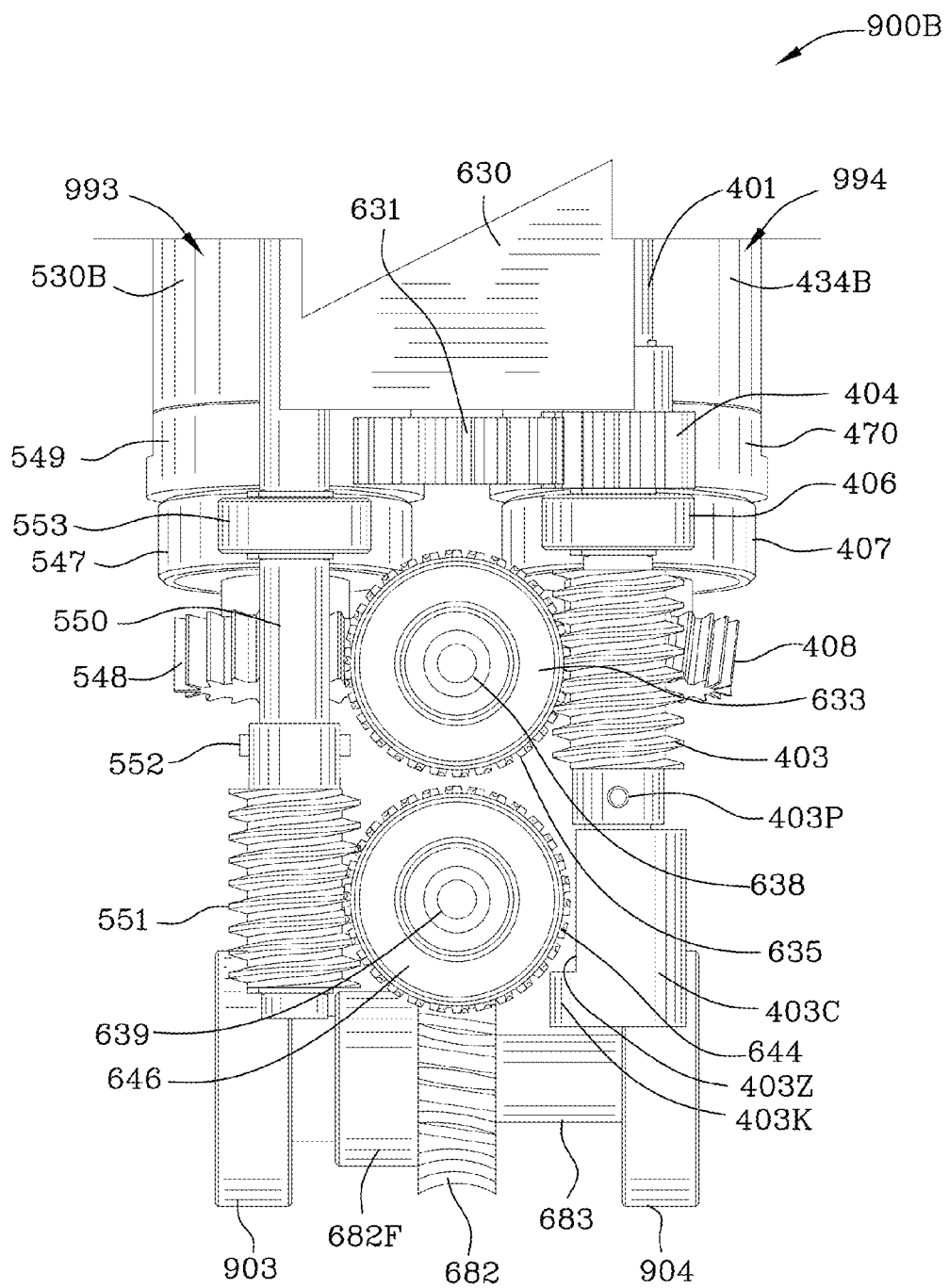
FIG. 9B is a schematic bottom view of the second end of FIG. 9.
Figure 9C:
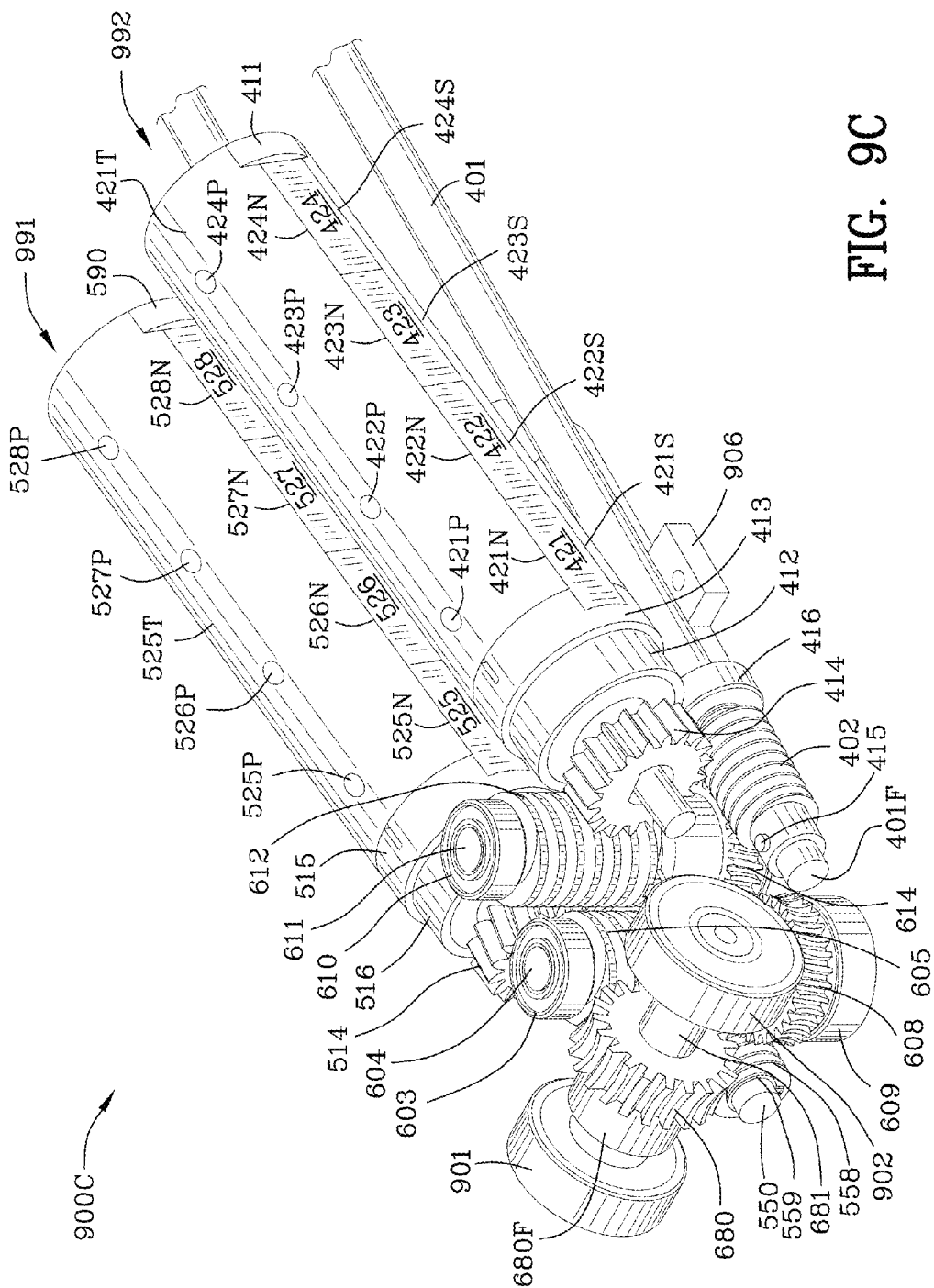
FIG. 9C is a schematic perspective view of the first end of FIG. 9 illustrating the first and third magnet rotor assemblies and associated shunt gearing as well as the propulsion system gearing.
Figure 9D:
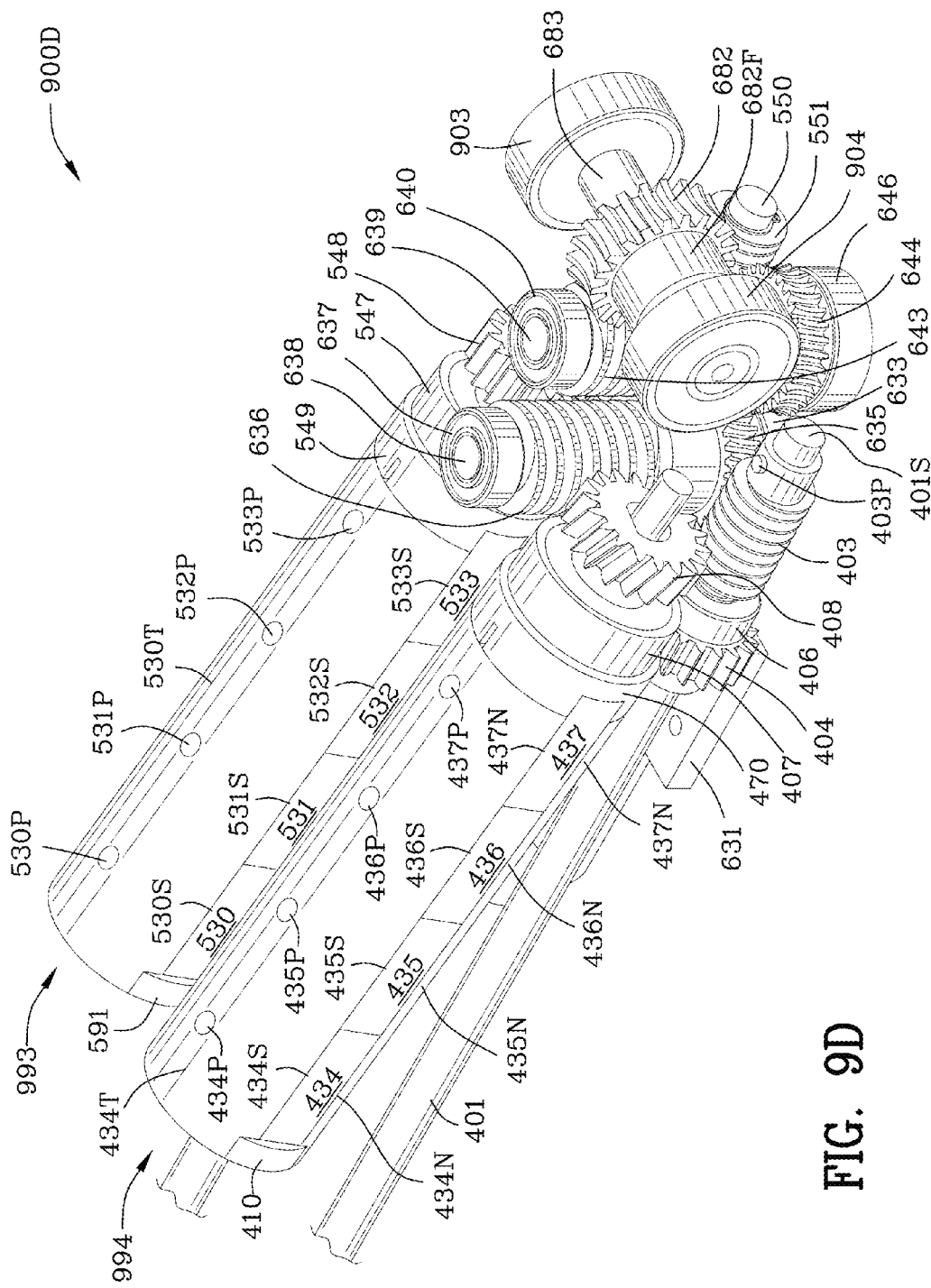
FIG. 9D is a schematic perspective view of the second end of FIG. 9 illustrating the second and fourth magnet rotor assemblies and associated gearing as well as the propulsion system gearing.

The second end of the conduit sensor device is the right end when viewing FIGS. 9, 9B and 9D, the end having magnet rotors assemblies 993, 994 and the gearing system 403, 404, 408, 548, 551, 635, 636, 643, 644, 682 proximate those rotor assemblies. See FIG. 9B, a schematic bottom view of the second illustrating shunt motor shaft output gear 631 driving spur gear 404 mounted on shunt shaft 401.

Referring to FIG. 9, first magnet rotor assembly 991 includes pins 525P, 526P, 527P, 528P which are press-fit through corresponding unnumbered holes in the top portion 525T and bottom portion 525B. Magnet rotor assembly 992 includes pins 421P, 422P, 423P, 424P which are press-fit through corresponding unnumbered holes in the top portion 421T and bottom portion 421B. Pins 525P, 526P, 527P, 528P are illustrated well in FIG. 9C as are pins 421P, 422P, 423P, 424P.

FIG. 9C is a schematic perspective view 900C of the first end of FIG. 9 illustrating the gear drive system 402, 414, 514, 555, 558, 605, 608, 612, 614, 620, 680 of the first end of the conduit sensor device together with the first end magnet rotor assemblies 991, 992. Also see FIG. 9A to view gears 555, 620. First magnet rotor assembly 991 includes permanent magnets 525, 526, 527 and 528 locked together by first rotor shaft end 515 proximate the gear drive system, top portion 525T of the rotor assembly, bottom portion of the rotor assembly and the rotor shaft end 590 distally located with respect to the gear drive system. First magnet rotor assembly 991 is housed in cylindrical housing 326 of second backing bar weldment 302 as illustrated in FIGS. 3E, 3F and 5. Third magnet rotor assembly 992 includes permanent magnets 421, 422, 423, and 424 locked together by third rotor shaft end 413 proximate the gear drive system, top portion 421T of the rotor assembly, bottom portion 421B of the rotor assembly and the rotor shaft end 411 distally located with respect to the gear drive system. Third magnet rotor assembly 992 is housed in cylindrical housing 426 of first backing bar weldment 301 as illustrated in FIGS. 4 and 4A. Still referring to FIG. 9C, the north poles 525N, 526N, 527N, 528N of the magnets of first magnet rotor assembly 991 are oriented facing upwardly (toward the pipe to be inspected) and, similarly, the north poles 421N, 422N, 423N and 424N of the magnets of third magnet rotor assembly 992 are oriented facing upwardly. The south poles 525S, 526S, 527S, 528S of the magnets of first magnet rotor assembly 991 are oriented facing downwardly. The south poles of 421S, 422S, 423S and 424S of the magnets of third magnet rotor assembly 992 are oriented facing downwardly. Reference is made to FIGS. 5 and 5A, to view the south poles 525S, 526S, 527S, 528S of the magnets of first magnet rotor assembly 991.

FIG. 9A is a bottom schematic view 900A of the first end of FIG. 9 illustrating the gearing system, first magnet rotor assembly 991, and third magnet rotor assembly 992. Bottom 421B of third magnet rotor assembly 992 and bottom 525B of first magnet rotor system 991 are illustrated in FIG. 9A. Propulsion motor support 616 is affixed to the base plate 311 and supports centrally located propulsion motor 620A. Propulsion motor driven spur gear 620 drives shaft spur gear 555. Shaft spur gear 555 includes an integral collar with a set screw therein for affixation to propulsion drive shaft 550. Helical gear 514 which is coupled to and drives first magnet rotor assembly 991 is illustrated mounted on first rotor shaft end 515 proximate the gear drive system. Third helical gear 414 which is coupled to and drives third magnet rotor assembly 992 is illustrated mounted on the third rotor shaft end 413 proximate the gear drive system. Bearings 516, 412, support the magnet rotor assemblies 991, 992, as they are mounted in gear box halves, 306, 305 respectively. Referring to FIGS. 4, and 4A, third magnet rotor assembly 992 is illustrated with bearing 412 mounted in bearing seat 305W of gear box half 305 and fourth magnet rotor assembly 994 is illustrated with bearing 407 mounted in bearing seat 307X of gear box half 307.

Figure 9E:
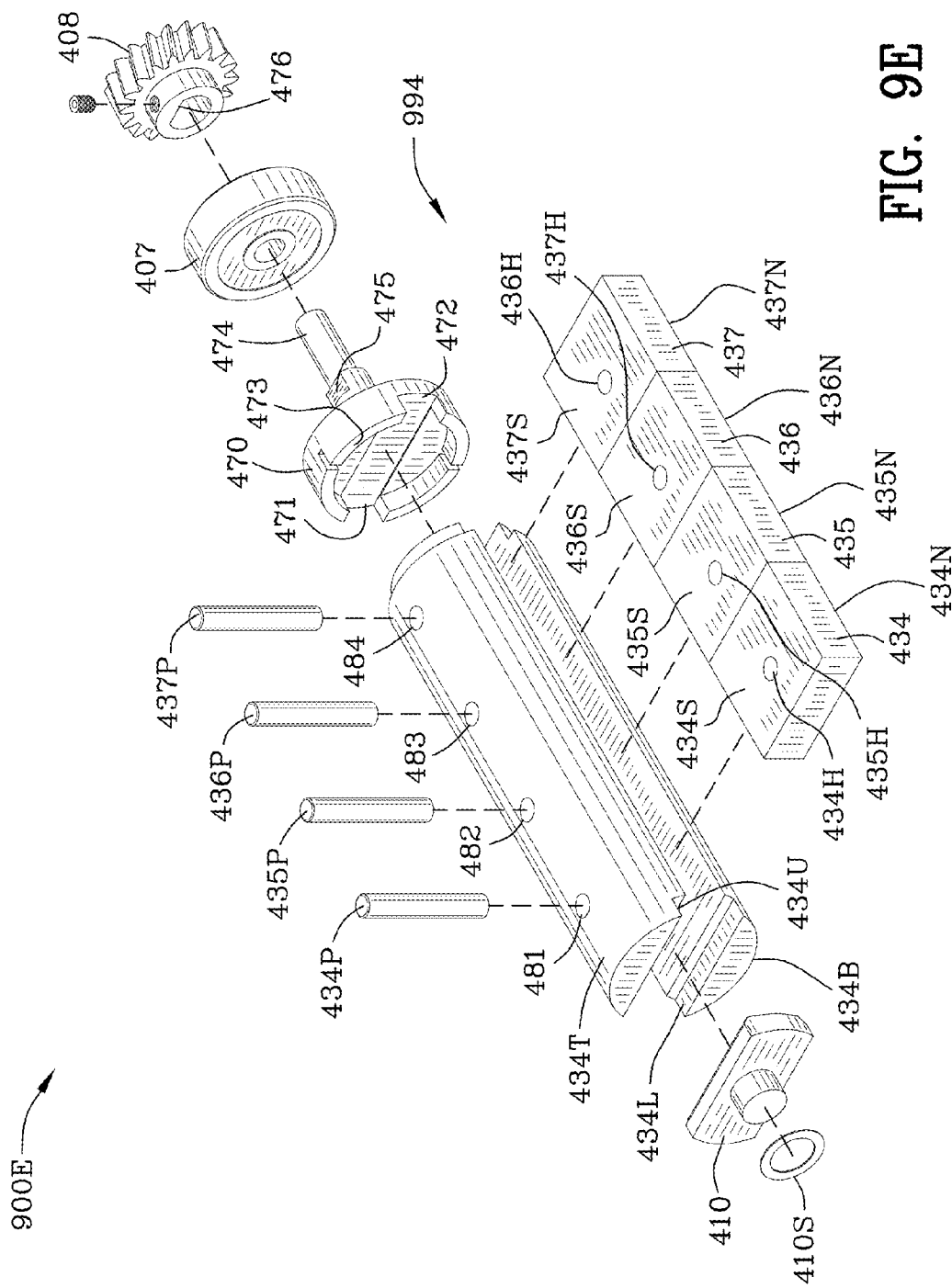
FIG. 9E is an exploded perspective view of one of the fourth magnet rotor assembly of the second end.
Figure 9F:
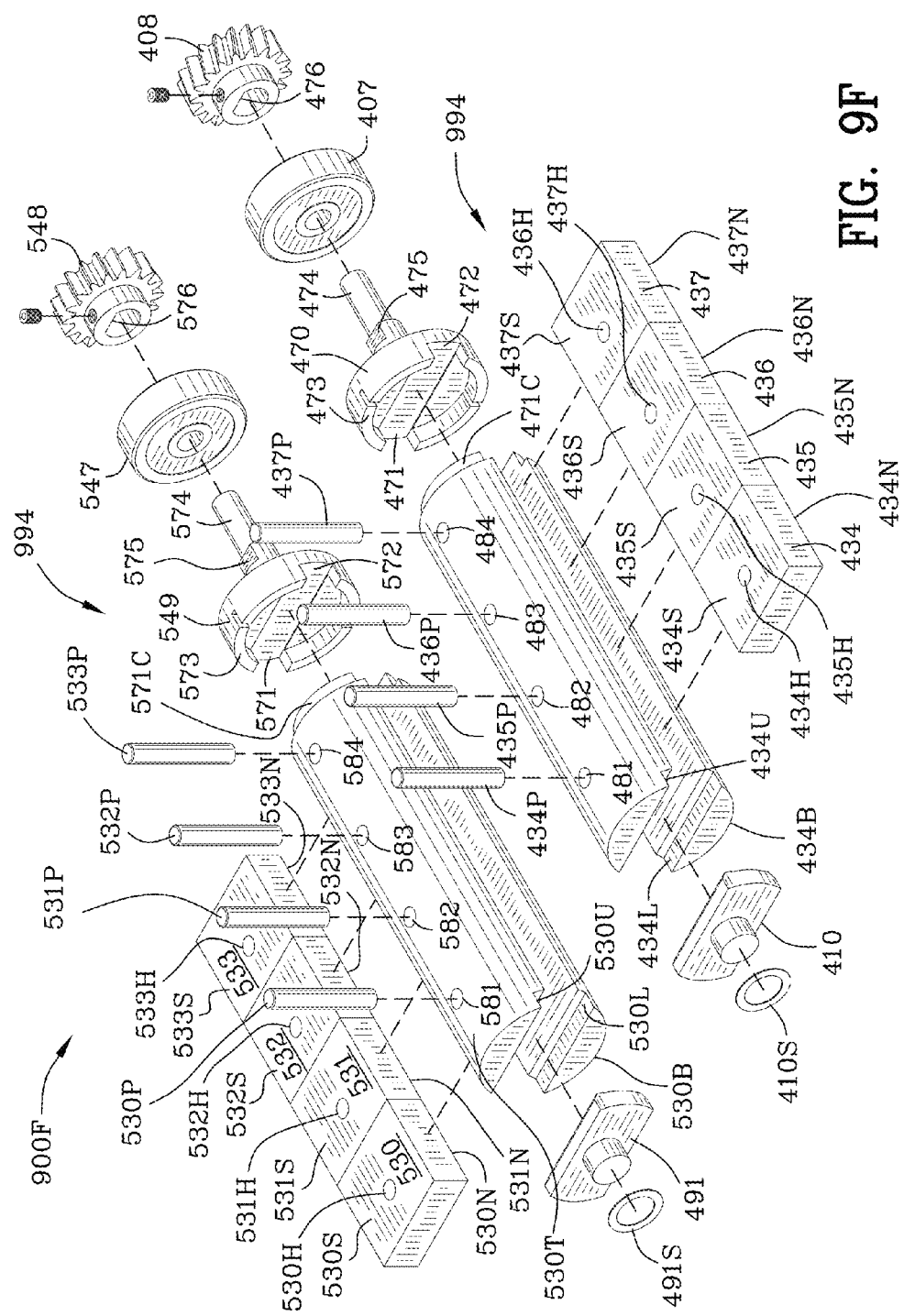
FIG. 9F is an exploded perspective view of the second and fourth magnet rotor assemblies of the second end.

FIG. 9E is an exploded perspective view 900E of fourth magnet rotor assembly 994 of the second end. Fourth magnet rotor assembly 994 is typical of magnet rotor assemblies 991, 992 and 993. FIG. 9F is an exploded perspective view 900F of the rotor assemblies 993, 994 of the second end. The structure illustrated in FIG. 9E of fourth magnet rotor assembly 994 is repeated in FIG. 9F. FIG. 9E is slightly larger and easier to read. Referring to FIG. 9E, fourth magnet rotor assembly 994 is illustrated wherein rotor shaft end 470 proximate the second end gear system is shown in an exploded perspective. Rotor shaft end 470 includes retaining slot 471 for magnet 437, another retaining slot 472 for magnet 437, a circumferentially shaped lip 473, a shaft portion 474 which includes at least two diameters, and, one portion of the shaft 474 includes a locking flat portion 475. Flat portion 475 engages a reciprocally shaped flat portion 476 in the collar of helical gear 408. The top portion 434T and the bottom portion 434B of the fourth magnet rotor assembly 994 includes a semi-circumferential 471C lip which fits into the circumferentially shaped lip 473 of the rotor shaft end 470.

Fourth magnet rotor assembly 994 includes magnets 434, 435, 436, 437 secured between a top 434T and a bottom 434B portion. Pins 434P, 435P, 436P and 437P are press-fit into corresponding through holes 481, 482, 483, 484 in the top portion 434T and the bottom portion 434B of the assembly. Magnets 434, 435, 436, 437 include holes 434H, 435H, 436H and 437H which permit passage of the pins therethrough. The north poles of the magnets 434N, 435N, 436N, 437N as well as the south poles of the magnets 434S, 435S, 436S, and 437S are illustrated in FIG. 9E. The south poles of the magnets 434, 435S, 436S and 437S are illustrated as facing upwardly in the direction of the pipe to be inspected. See FIGS. 4 and 4A for a schematic view of the orientation of the magnets 434, 435, 436, 437. Rotor shaft end 410 distally located with respect to the gear drive system secures the fourth magnet rotor assembly 994 together. Snap-ring 410S locks rotor shaft end 410 in place between upper shoulder 434U in the top portion 434T and the lower shoulder 434L in the bottom portion 434B. Rotor shaft 410 includes a cylindrical end portion which resides in backing bar weldment 301 as illustrated in FIGS. 4 and 4A. Circular opening 410D is larger than the diameter of end 410 and supports fourth magnet rotor assembly 994. Each magnet rotor assembly includes a bearing. One such bearing 407 is illustrated in FIG. 9E which resides in bearing seat 307X of gear box half 307 and supports the magnet rotor assembly 994. See FIGS. 4 and 4A.

FIG. 9F is an exploded perspective view 900F of the rotor assemblies 993, 994 of the second end. Referring to FIG. 9F the second magnet rotor assembly 993 is illustrated wherein rotor shaft end 549 proximate the second end gear system is shown in exploded perspective. Rotor shaft end 549 includes retaining slot 571 for magnet 533, another retaining slot 572 for magnet 533, a circumferentially shaped lip 573, a shaft portion 574 which includes at least two diameters, and, one portion of the shaft 574 includes a locking flat portion 575. Flat portion 575 engages a reciprocally shaped flat portion 576 in the collar of helical gear 548. The top portion 530T and the bottom portion 530B of the second magnet rotor assembly 993 includes a semi-circumferential 571C lip which fits into the circumferentially shaped lip 573 of the rotor shaft end 549.

Second magnet rotor assembly 993 includes magnets 530, 531, 532, 533 secured between a top portion 530T and a bottom portion 530B. Pins 530P, 531P, 532P and 533P are press-fit into corresponding through holes 581, 582, 583, 584 in the top portion 530T and the bottom portion 530B of the assembly. Magnets 530, 531, 532, 533 include holes 530H, 531H, 532H and 533H which permit passage of the pins therethrough. The north poles of the magnets 530N, 531N, 532N, 533N as well as the south poles of the magnets 530S, 531S, 532S, and 533S are illustrated in FIG. 9F. The south poles of the magnets 530S, 531S, 532S and 533S are illustrated as facing upwardly in the direction of the pipe to be inspected. See FIGS. 5 and 5A for a schematic view of the orientation of the magnets 530, 531, 532, 533. Rotor shaft end 491 distally located with respect to the gear drive system secures the second magnet rotor assembly 993 together. Snap-ring 491S locks rotor shaft end 491 axially in place between upper shoulder 530U in the top portion 530T and the lower shoulder 530L in the bottom portion 530B. Rotor shaft 591 includes a cylindrical end portion which resides in backing bar weldment 302 as illustrated in FIGS. 5 and 5A. Circular opening 591D is larger than the diameter of end 591 and supports third magnet rotor assembly 993. Each magnet rotor assembly includes a bearing. One such bearing 547 is illustrated in FIG. 9F which resides in bearing seat 308X of gear box half 308 and supports the magnet rotor assembly 993.

Gear box halves 305, 306 are connected together and house the gear systems illustrated in FIGS. 6, 6A, 9, 9A, and 9C. As stated previously, the gear boxes are secured to each other, to first and second backing bar weldments 301, 302, to bottom plate 309 and to the first end of base plate 311A by screws and/or other attachment means.

Gear box halves 308, 307 are connected together and house the gear systems illustrated in FIGS. 6, 6B, 9, 9B, and 9D. As stated previously in regard to the gear box halves 306, 305, the gear box halves 308, 307 are similarly secured to each other, to first and second backing bar weldments 301, 302, to bottom plate 310 and to the second end of base plate 311B by screws and/or other attachment means.

Figure 3L:
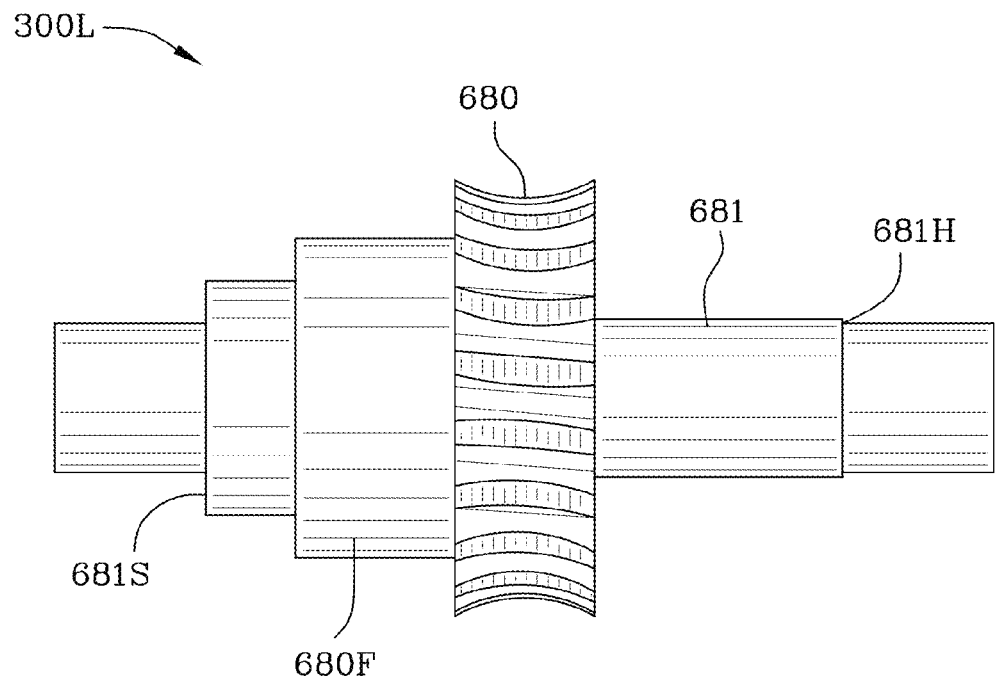
FIG. 3L is a schematic plan view of the wheel propulsion drive shaft of the first end together with the drive gear.
Figure 3M:
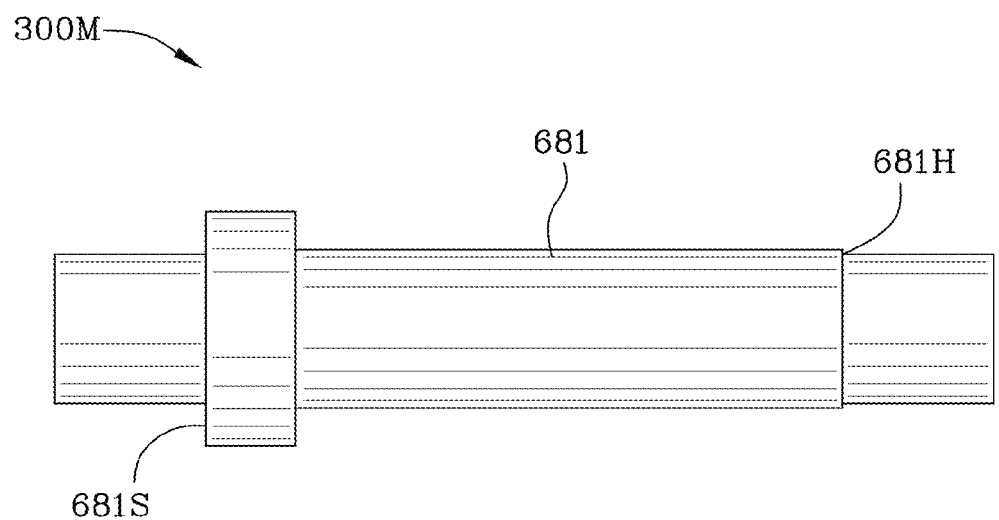
FIG. 3M is a schematic plan view of the wheel propulsion drive shaft of the first end.

FIG. 3L is a schematic plan view 300L of the wheel propulsion drive shaft 681 of the first end together with the worm wheel/worm drive gear 680. Drive worm gear 680 includes an integral collar 680F which is affixed to the drive shaft 681. FIG. 3M is a schematic plan view 300M of the wheel propulsion drive shaft 681 of the first end wherein shoulders 681S, 681H restrain movement of bearings 901, 902. Bearings 901, 902 are illustrated in FIGS. 9, 9A and 9C.

Figure 3N:
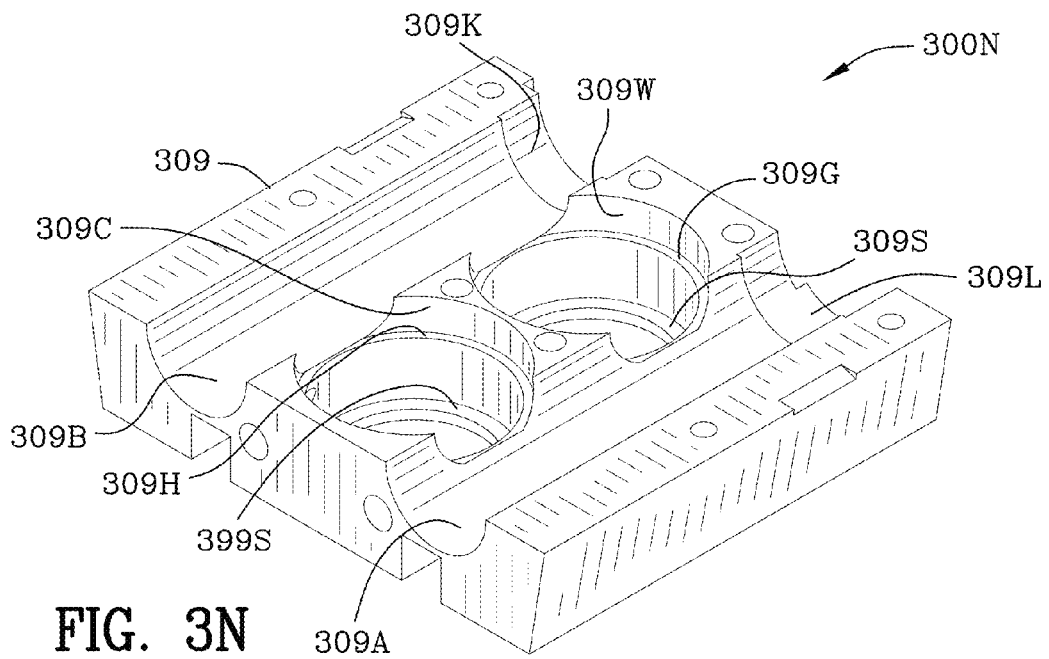
FIG. 3N is a schematic perspective view of the bottom plate of the first end of conduit sensor device with magnetic shunt.

FIG. 3N is a schematic perspective view 300N of the bottom plate 309 of the first end of conduit sensor device with magnetic shunt. Slot 309A in first end gear box bottom plate 309 houses shunt shaft 401 and worm 402 affixed thereto. Slot 309B in first end gear box bottom plate 309 houses propulsion shaft 550 and worm 558 affixed thereto. Slot 309B is adjacent slot 306S in gear box half 306. Together slots 309B and 306S form a housing/passageway for the propulsion shaft 550 and worm 558. Slot 309A is adjacent slot 305S in gear box half 305 and these together form a housing/passageway for shunt shaft 401 and worm 402.

Figure 3O:
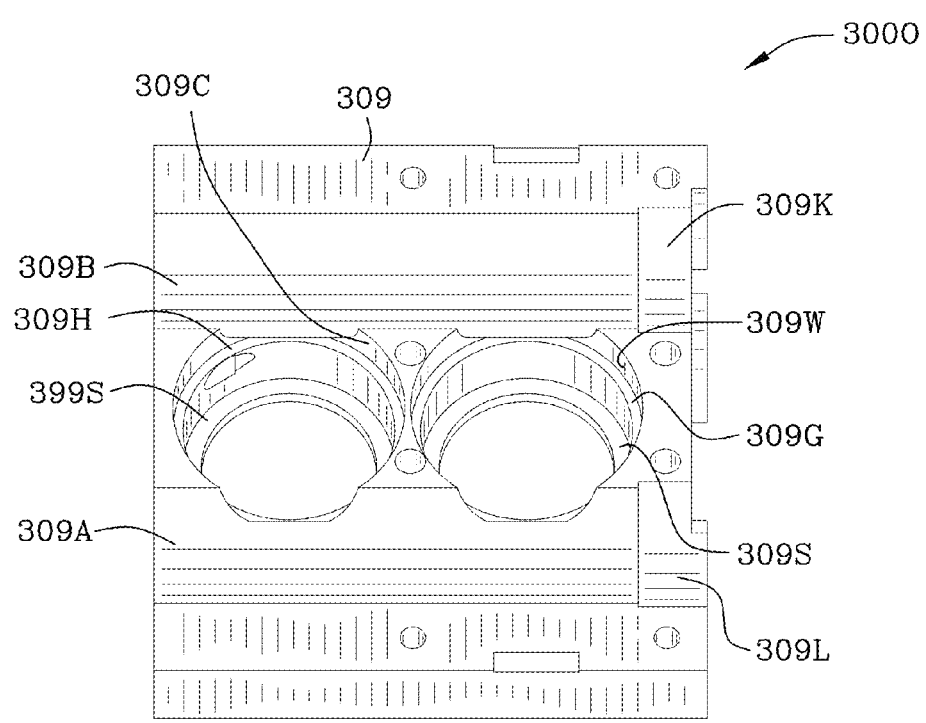
FIG. 3O is another schematic perspective view of the bottom plate of the first end of conduit sensor device with magnetic shunt.

Referring to FIGS. 3N and 6A, shoulder 309S supports lower bearing 609A for shunt worm wheel 614 which drives vertical shunt worm 612. Shoulder 399S supports lower bearing 609 for drive worm wheel 608 which drives vertical drive worm 605. Shoulder 309G extends to cylindrical wall 309W. Cylindrical wall 309W in base plate 309 provides room for the rotation of shunt worm wheel 614 as it is diametrically larger than the shunt worm wheel 614. Shoulder 309H extends to cylindrical wall 309C. Cylindrical wall 309C in base plate 309 provides room for the rotation of drive worm wheel 608 as it is diametrically larger than the drive worm wheel 608. FIG. 3O is another schematic perspective view 300O of the bottom plate 309 of the first end of conduit sensor device with magnetic shunt illustrating the same features just described.

FIG. 9D is a schematic perspective view 900D of the second end of FIG. 9. FIG. 9B is a schematic bottom view 900B of the second end of FIG. 9. FIG. 6B is an enlargement 600B of a portion of FIG. 6.

Referring to FIGS. 6 and 6B, a bearing seat supports upper bearing 637. Shunt shaft 638 and shunt worm drive 636 are supported by bearings 637, 633. Upper bearing 640 supports drive shaft 639. Vertical shunt worm 643 is affixed to drive shaft 639 by pin 642 as illustrated in FIG. 6B. Vertical shunt worm wheel 635 and vertical drive worm 636 include slots therein as best viewed in FIG. 6B. Vertical drive worm 643 is restrained by a shoulder in gear box 602 against upward movement.

Referring to FIG. 6B, bearing 633 is supported by a shoulder of bottom plate 310. Similarly, bearing 646 is supported by a shoulder of bottom plate 310. Spacer 634 resides between bearing 633 and shunt worm wheel 635. Spacer 634A resides between vertical shunt worm 636 and upper bearing 637. Shunt worm wheel 635 is driven by shaft driven worm 403 as illustrated in FIGS. 4 and 4A. Worm wheel 635, drive shaft 638, and vertical shunt worm 636 are affixed to each other by pin 641 and, thus, all three components 635, 638, 636 rotate together.

Referring to FIG. 6B, shunt motor 698 includes shaft 698S which drives output shaft gear 631 which, in turn, drives spur gear 406 affixed to shunt shaft 401. See FIGS. 4 and 4A to view spur gear 406. Worm 403 is affixed to shunt shaft 401 and as shunt shaft 401 rotates, worm 403 rotates, shunt worm wheel 635 rotates, and, vertical shunt worm 636 rotates driving helical gears 408, 548. For counter clockwise rotation of shunt shaft 401 when viewed from the perspective of the first end, 90° rotation of helical gears 408, 548 by shunt worm 636 causes rotation of second end magnet rotor assemblies 993, 994 in opposite directions repositioning the magnets such that north poles of the second magnet rotor assembly 993 face north poles of fourth magnet rotor assembly 994. See FIGS. 10 and 10A. For clockwise rotation of shaft 401 when viewed from the perspective of the first end of the device, 90° rotation of helical gears 408, 548 by shunt vertical worm 636 causes rotation of second end magnet rotor assemblies 993, 994 in opposite directions repositions the magnets such that south poles of the magnet rotor assembly 993 face south poles of the fourth magnet rotor assembly 994.

FIG. 9D is a schematic perspective view 900D of the second end of FIG. 9 illustrating the gear drive system 403, 404, 408, 548, 551, 635, 636, 643, 644, 682 of the second end of the conduit sensor device 101 together with the magnet rotor assemblies 993, 994 residing substantially at the second end of the device. Also see FIG. 9B. Second magnet rotor assembly 993 includes permanent magnets 530, 531, 532, 533 locked together by second end rotor shaft end 549 proximate the gear drive system, top portion 530T of the rotor assembly, bottom portion of the rotor assembly and the rotor shaft end 591 distally located with respect to the gear drive system. Fourth magnet rotor assembly 994 includes permanent magnets 434, 435, 436, 437 locked together by second rotor shaft end 470 proximate the gear drive system, top portion 434T of the rotor assembly, bottom portion 434B of the rotor assembly and the rotor shaft end 410 distally located with respect to the gear drive system. Still referring to FIG. 9D, the south poles 530S, 531S, 532S, 533S of the magnets of second magnet rotor assembly 993 are oriented facing upwardly (toward the pipe to be inspected) and, similarly, the south poles 434S, 435S, 436S and 437S of the magnets of fourth magnet rotor assembly 994 are oriented facing upwardly. The north poles 530N, 531N, 532N, 533N of the magnets of second magnet rotor assembly 993 are oriented facing downwardly. The north poles 434N, 435N, 436N and 437N of the magnets of fourth magnet rotor assembly 994 are oriented facing downwardly. Reference is made to FIGS. 5 and 5A, to view the north poles 530N, 531N, 532N, 533N of the magnets of second magnet rotor assembly 993.

FIG. 9B is a bottom schematic view 900B of the second end of FIG. 9 illustrating the gearing system, second magnet rotor assembly 993, and fourth magnet rotor assembly 994. Bottom 434B of fourth magnet rotor assembly 994 and bottom 530B of second magnet rotor system 993 are illustrated in FIG. 9B. Shunt motor support 630 is affixed to the base plate 311 and supports centrally located shunt motor 698. Shunt motor driven spur gear 631 drives shaft spur gear 404. Shaft spur gear 404 includes an integral collar with a set screw therein for affixation to shunt shaft 401. Helical gear 548 which drives second magnet rotor assembly 993 is illustrated and is mounted on second end rotor shaft 549 proximate the gear drive system. Fourth helical gear 408 which drives fourth magnet rotor assembly 994 is illustrated and is mounted on the second end rotor shaft proximate the gear drive system. See FIG. 9F. Bearings 547, 407, support the magnet rotor assemblies 993, 994, as they are mounted in gear box halves, 307, 308 respectively. Referring to FIGS. 4 and 4A, fourth magnet rotor assembly 994 is illustrated with bearing 407 mounted in bearing seat 307X of gear box half 307. Referring to FIGS. 5 and 5A, second magnet rotor assembly 993 is illustrated with bearing 547 mounted in bearing seat 308X of gear box half 308.

FIG. 7 is a plan view 700 of magnet drive shaft 401, first end worm 402, spur gear 404 affixed to shaft and second end worm 403. Bearings 416, 406 support shaft 401 as best viewed in FIGS. 4 and 4A. Snap rings 416S, 417S restrain bearing 416 against axial movement on shaft 401. Bearing 416 resides in gear box half 305 and bottom plate 309. Bearing 406 resides in gear box half 307 and bottom plate 310. FIG. 4 is cross-sectional view 400 taken along the line 4-4 of FIG. 3A. Line 4-4 is taken along the centerline of magnetic shunt shaft 401. FIG. 4A is a cross-sectional view 400A taken along the line 4-4 of FIG. 3A. First end worm 402 is restrained in place by shoulder 402S and pin 415. Pin 415 extends through worm 402 and shaft 401. Pin 415 prevents rotation of worm 402 with respect to shaft 401. Pin 415 is press-fit into a hole in shaft 401. Pin 415 passes through worm 402 and restrains worm 402 against axial movement with respect to shaft 401. Shoulder 402S also restrains worm 402 against axial movement.

Still referring to FIG. 7, spur gear 404 includes an integral collar with a set screw 438S for affixing the collar against rotation with respect to magnet drive shaft 401. Snap rings 438, 439 secure spur gear 404 axially with respect to shaft 401. Snap rings 439 and 453S secure bearing 406 against axial movement with respect to shaft 401. Second end worm 403 is affixed to magnet drive shaft 401 in the same way that first end worm 402 is affixed to shaft 401. Pin 403P is press fit into a hole in shaft 401 and restrains the worm 403 against axial movement along shaft 401. Pin 403P extends through worm 403 and shaft 401 and prevents rotation of worm 403 with respect to shaft 401. Referring to FIG. 7E, shoulder 403S also restrains movement of second end worm 403 against movement on shaft 401.

Pins 415 and 403P lock worms 402, 403 to shunt shaft 401 and against rotation with respect to the shunt shaft. Shunt shaft 401 is shorter than the propulsion drive shaft 550. Shunt shaft 401 drives the magnet rotor assemblies 991, 992, 993 and 994. Shunt shaft 401 can rotate clockwise or counter clockwise. FIG. 7A is a cross-sectional view 700A taken along the lines 7A-7A of FIG. 7. FIG. 7B is an enlargement 700B of the first end portion of FIG. 7. FIG. 7C is a cross-sectional enlargement 700C of the first end portion of FIG. 7. FIG. 7D is an enlargement 700D of the second end portion of FIG. 7. FIG. 7E is a cross-sectional enlargement 700E of the second end portion of FIG. 7.

FIG. 8 is a plan view 800 of propulsion drive shaft 550, first end worm 558, spur gear 555 affixed to shaft 550 and second end worm 551. First end worm 558 is secured to shaft 550 against rotation with respect to the shaft by pin 557. Snap ring 559 secures the worm 558 against leftward movement along shaft 550. Pin 557 resides in slot 557S illustrated in FIG. 8A. Snap rings 556S, 561S secure bearing 560 axially in place on shaft 550. Snap rings 561S, 562S secure spur gear 555 axially on propulsion drive shaft 550. Set screw 597 secures the spur gear 555 on shaft 550. Snap rings 554S, 553S secure bearing 553 axially on shaft 550. Bearings 560, 553 support shaft 550. Bearing 560 is mounted in gear box half 306 and bottom plate 309. Bearing 560 is supported by surface 309K in the bottom plate and by surface 306S in gear box half 306. Bearing 553 is mounted in gear box half 308 and bottom plate 310. See FIG. 5.

Still referring to FIG. 8, second end worm 551 is restrained against rightward movement by snap ring 570S. Further, pin 552 is press fit into shaft 550 within slot 552S in the second end worm 551. Some axial movement of worm 551 is permitted. FIG. 8A is a cross-sectional view 800A taken along the lines 8A-8A of FIG. 8. FIG. 8B is an enlargement 800B of the first end portion of FIG. 8. FIG. 8C is a cross-sectional enlargement 800C of the first end portion of FIG. 8. FIG. 8D is an enlargement 800D of the second end portion of FIG. 8. FIG. 8E is a cross-sectional enlargement 800E of the second end portion of FIG. 8.

FIG. 4 is cross-sectional view 400 taken along the line 4-4 of FIG. 3A. FIG. 4A is a cross-sectional view 400A taken along the line 4-4 of FIG. 3A. Line 4-4 of FIG. 3A is not coincident with the centerline of magnet rotor assemblies 993, 994. Line 4-4 is taken along the centerline of the shunt shaft 401. Shunt shaft 401 resides slightly inwardly of the centerline of magnet rotor assemblies 993, 994. Shunt shaft 401 is sometimes referred to herein as the magnet drive shaft. FIG. 4 illustrates the magnet rotor assemblies 992, 994 in their home or normal position. In the normal position the magnets of third magnet rotor assembly 992 are oriented such that the north poles 421N, 422N, 423N, 424N of the magnets 421, 422, 423, 424 are oriented facing upwardly. In the normal position the magnets of fourth magnet rotor assembly 994 are oriented such that the south poles 434S, 435S, 436S, 437S are oriented facing upwardly. Reference is made to FIG. 4A, wherein magnetic field 450 is illustrated for the normal position of magnet rotor assemblies 992, 994. Pipe 499 is illustrated with field lines 450 passing therethrough. As illustrated in FIG. 4A, wheels 107, 108 are illustrated in engagement with pipe 499. Sensors 106 detect abnormalities or defects anywhere in the pipe. FIGS. 4 and 4A illustrate the magnetic field 450 generated for the second and fourth magnet rotor assemblies. The magnetic field generated 450A for the first and third magnet rotor assemblies is illustrated in FIG. 5A.

Still referring to FIGS. 4 and 4A, shunt shaft 401 is illustrated in cross-section. Sometimes herein shunt shaft 401 is referred to as magnet shaft 401. FIG. 4A also illustrated worms 402, 403 and shaft bearings 416, 406. Magnet rotor assemblies 992, 994 are illustrated within cylindrical housings 426, 427 in first backing bar weldment 301. Cylindrical opening 411D in backing bar weldment 301 is illustrated with rotor end 411 slip-fitted therein so as to permit rotation of rotor end 411 with respect to the cylindrical opening 411D. Similarly, cylindrical opening 410D in backing bar weldment 301 is illustrated with rotor end 410 slip-fitted therein so as to permit rotation of rotor end 410 with respect to cylindrical opening 410D. Rotor assemblies 992, 994 are substantially cylindrically-shaped and have a diameter slightly smaller than cylindrical housings 426, 427.

Operation of the magnetic shunt drive system is now described in greater detail.

Referring to FIGS. 4, 4A, 7, and 7A, the entire length of shunt shaft 401 is viewed as is spur gear 404 affixed to shunt shaft 401 by snap rings 438, 439 and a set screw 438. FIGS. 7, 7A, 7B, 7C, 7D and 7E illustrate the shunt shaft 401, worms 402, 403 and their mounting on the shunt shaft 401, bearings 406, 416 which support the shunt shaft 401, and spur gear 404. Spur gear 404 is affixed to shunt shaft 401 and, as such, spur gear 404 rotates with shunt shaft 401. Spur gear 404 is driven by shunt motor spur gear 631 as best viewed in FIG. 9B. FIG. 9B is a bottom view of the second end of the conduit sensor device. Shunt motor spur gear 631 is driven by shunt motor 698 as illustrated in FIG. 6B. Referring to FIG. 4A, bearing 416 resides between support 305S in the gear box half 305 and support 309L in bottom plate 309. Bearing 406 similarly supports shaft 401 on the second end of the shaft between an unnumbered support in gear box 307 and an unnumbered support in bottom plate 310. Shunt shaft 401 rotates worm 402 at the first end of the device and shunt shaft 401 rotates worm 403 at the second end of the device. Worms 402, 403 are right handed.

Rotation of the shunt shaft 401 in the clockwise direction from the perspective of the first end is now described. Reaction of the gearing system which drives the magnet rotor assemblies 991, 992, 993, 994 is now described as well in connection with the clockwise rotation of shunt shaft 401.

Figure 9G:
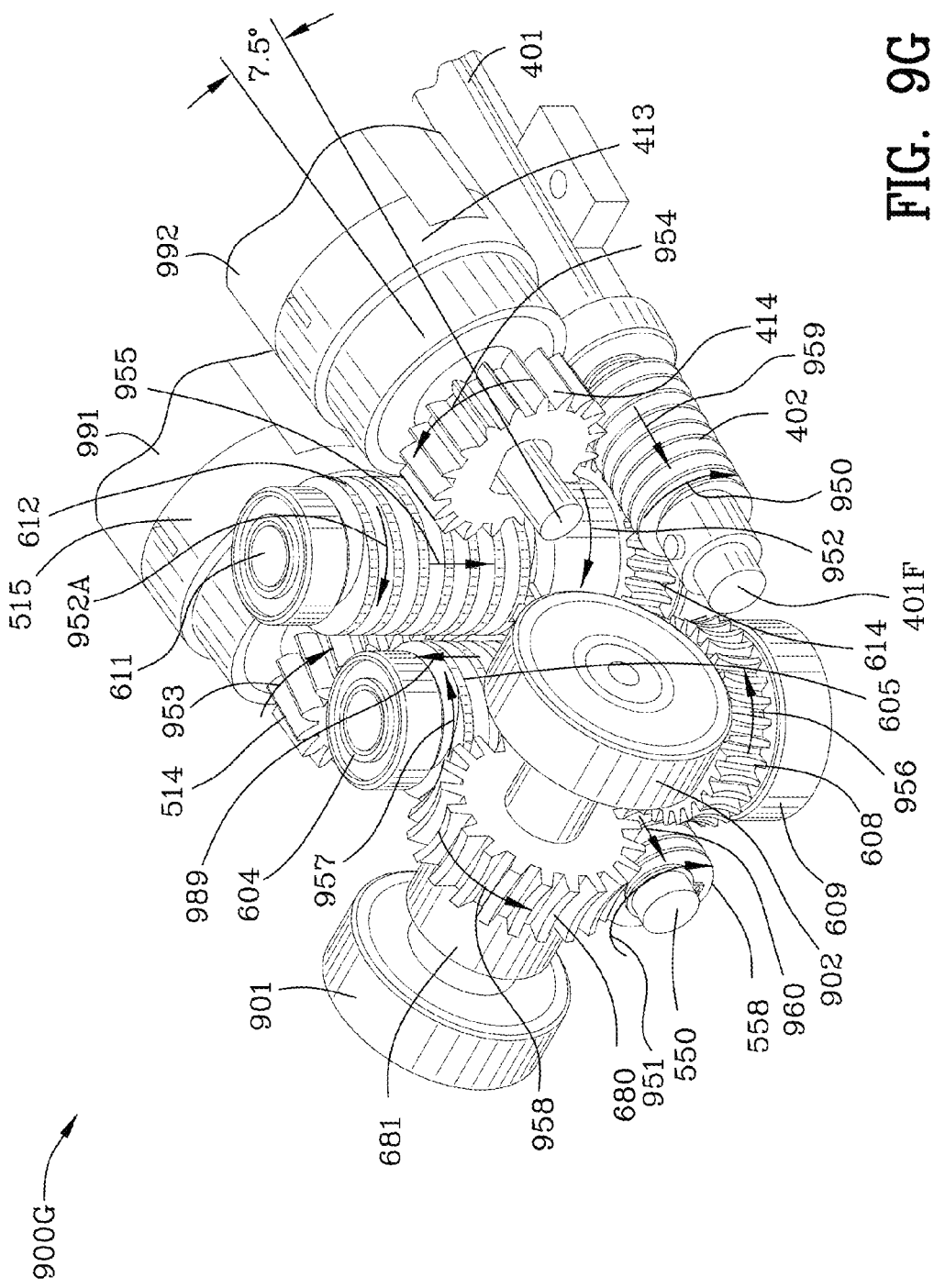
FIG. 9G is a schematic perspective view similar to FIG. 9C indicating rotation of the shunt drive shaft in the clockwise direction as defined from the perspective of the first end of the conduit sensor device and also indicating rotation of the propulsion drive shaft in the clockwise direction as defined from the perspective of the first end of the conduit sensor device.

FIG. 9G is a schematic perspective view 900G similar to FIG. 9C indicating rotation of the shunt drive shaft 401 in the clockwise direction 950 as defined from the perspective of the first end of the conduit sensor device and also indicating rotation of the propulsion drive shaft 550 in the clockwise direction 951 as defined from the perspective of the first end of the conduit sensor device.

Referring to FIGS. 9C and 9G, worm 402 engages right handed worm wheel 614 at the first end of the device. Shaft 611 of worm wheel 614 is oriented 90° with respect to shaft 401 of worm 402. As worm 402 is rotated in clockwise direction 950 as shunt shaft 401 is rotated in a clockwise direction 950 when viewed from the first end of the conduit sensor device as illustrated in FIGS. 9C and 9G, then worm wheel 614 is rotated clockwise 952 when viewed from the perspective above shaft 611. Arrow 959 indicates the direction of travel of the helical gear teeth of worm wheel 614 with respect to worm 402. Arrow 959 is substantially tangent to worm wheel 614.

Still referring to FIGS. 9C and 9G, worm wheel 614 is locked to shaft 611 and right handed vertical worm 612. Right handed helical gear 514 is in engagement with right handed vertical worm 612. Arrow 955 indicates the direction of travel of the helical gear teeth of helical gears 514, 414 with respect to vertical worm 612. Arrow 955 is substantially tangent to helical gears 514, 410. As shaft 611 of vertical worm 612 is rotated clockwise 952A, then helical gear 514 is rotated in the clockwise direction 953 along the shaft of helical gear 514. Vertical worm 612 has a helix angle of 10°. The first magnet rotor assembly is mounted at 7.5° with respect to horizontal. Therefore, helical gear 514 has a helix angle of 17.5° which equals 10° plus 7.5°. Different mounting angles may be used, different helix angles of the vertical worm may be used and different helix angles of the helical gear may be used.

Referring to FIGS. 9C, 9G, and 5A, right handed helical gear 514 is mounted on a shaft portion of the first rotor shaft end 515. Simultaneously, as shaft 611 of vertical worm 612 is rotated in the clockwise direction viewed from above, then right handed third helical gear 414 is rotated in the counter clockwise direction 954 along the shaft of third helical gear 414. Vertical worm 612 has a helix angle of 10°. The second magnet rotor assembly is mounted at 7.5° with respect to horizontal. Therefore, third helical gear 414 has a helix angle of 2.5° which equals 10° minus 7.5°. See FIG. 9G wherein the 7.5° angle is illustrated. See FIGS. 9C, 9G and 4A.

Referring to FIGS. 9C, 9G, 4A, and 5A, right handed third helical gear 414 is mounted on a shaft portion of the third rotor shaft end 413. First magnet rotor assembly 991 is affixed to first rotor shaft end 515 and rotates therewith and first rotor shaft end 515 is affixed to first helical gear 514 and rotates therewith. Third magnet rotor assembly 992 is affixed to third rotor shaft end 413 and rotates therewith and third rotor shaft 413 is affixed to third helical gear 414 and rotates therewith.

Figure 9H:
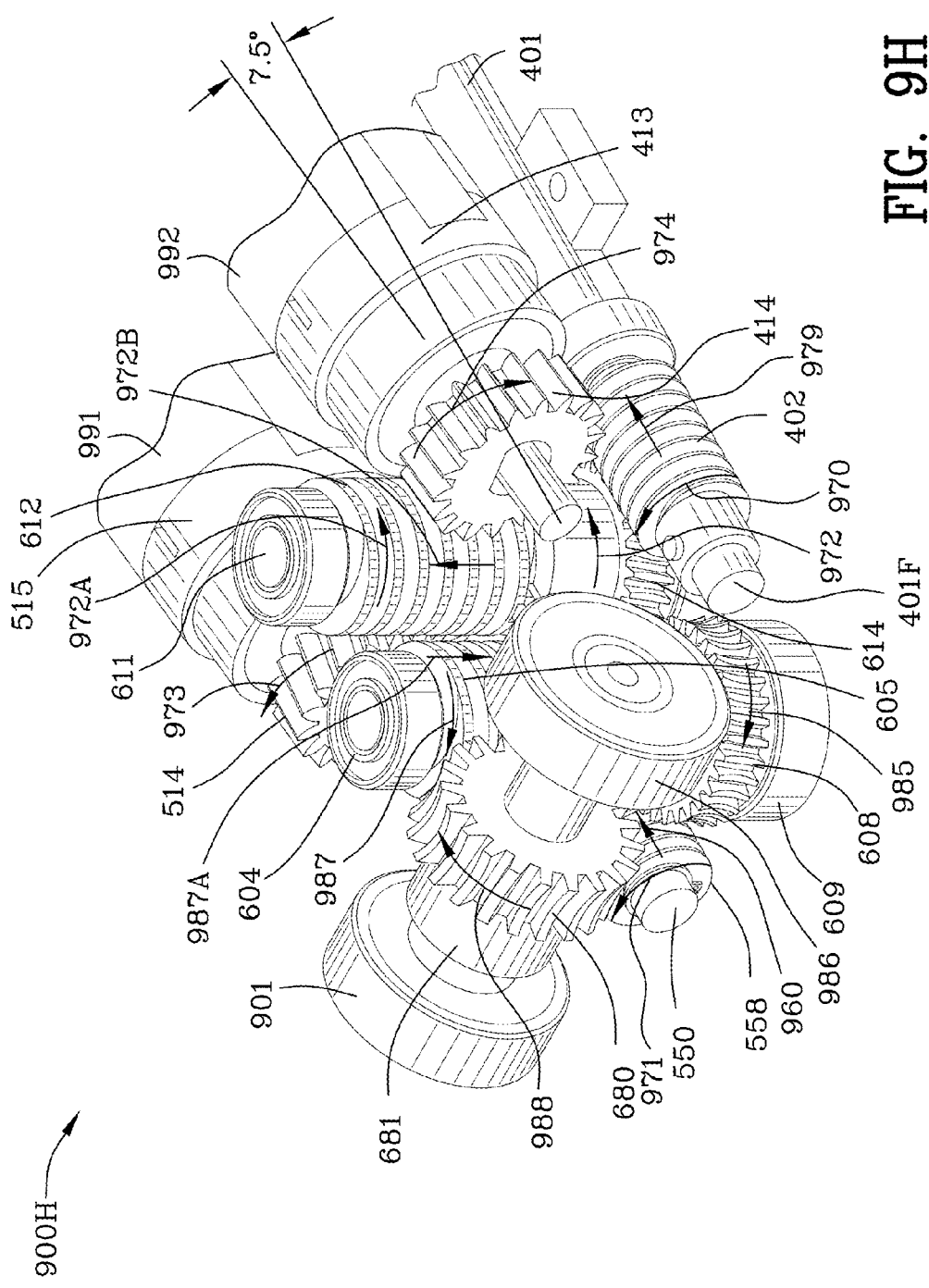
FIG. 9H is a schematic perspective view similar to FIG. 9C indicating rotation of the shunt drive shaft in the counter clockwise direction as defined from the perspective of the first end of the conduit sensor device and also indicating rotation of the propulsion drive shaft in the counter clockwise directions as defined from the perspective of the first end of the conduit sensor device.
Figure 9I:
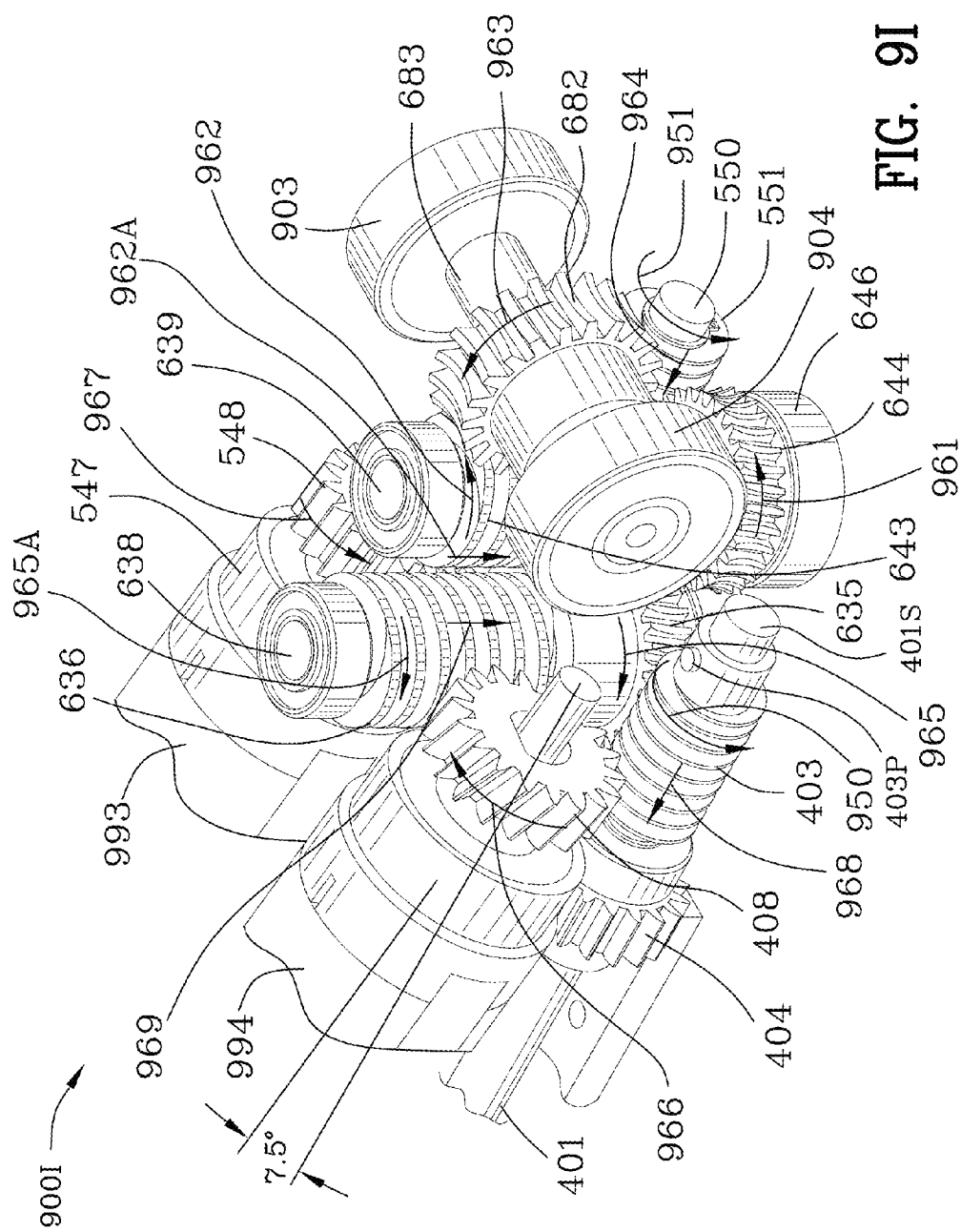
FIG. 9I is a schematic perspective view similar to FIG. 9D indicating rotation of the shunt drive shaft in the clockwise direction as defined from the perspective of the first end of the conduit sensor device and also indicating rotation of the propulsion drive shaft in the clockwise directions as defined from the perspective of the first end of the conduit sensor device.

FIG. 9I is a schematic perspective view 900I of FIG. 9D indicating rotation of the shunt drive shaft 401 in the clockwise direction 950 as defined from the perspective of the first end of the conduit sensor device and also indicating rotation of the propulsion drive shaft 550 in the clockwise direction 951 as defined from the perspective of the first end of the conduit sensor device.

Worm 403 engages right handed worm 635 at the second end of the conduit sensor device. See FIGS. 9D and 9I. Shaft 638 of worm 636 is oriented 90° with respect to shaft 401 of worm 403. Arrow 968 indicates the direction of travel of the teeth of helical worm wheel 635 with respect to helical worm 403. Arrow 968 is substantially tangent to worm wheel 635. As worm 403 is rotated in clockwise direction 950, as shunt shaft 401 is rotated in a clockwise direction 950, when viewed from the first end of the conduit sensor device as illustrated in FIG. 9C, then worm wheel 635 is rotated clockwise 965 when viewed from the perspective above shaft 638. Arrow 969 indicates the direction of travel of the teeth of helical gears 408, 548 with respect to vertical helical worm 636. Arrow 969 is substantially tangent with respect to second helical gear 548 and third helical gear 408. Worm wheel 635 is locked to shaft 638 and right handed vertical worm 636. Right handed fourth helical gear 408 is in engagement with right handed vertical worm 636. As shaft 638 of vertical worm 636 is rotated clockwise 965A, then fourth helical gear 408 is rotated in the clockwise direction 966 along the shaft of fourth helical gear 408. Vertical worm 636 has a helix angle of 10°. The fourth magnet rotor assembly is mounted at 7.5° with respect to horizontal. Therefore, fourth helical gear 408 has a helix angle of 17.5° which equals 10° plus 7.5°. Right handed fourth helical gear is mounted on a shaft portion of the second rotor shaft end 470. Worm 636 engages second helical gear 548. Simultaneously, as shaft 638, and vertical worm 636 are rotated in the clockwise direction 965A viewed from above, then right handed second helical gear 548 is rotated in the counter clockwise direction 967 along the shaft of second helical gear 548. Vertical worm 636 has a helix angle of 10°. The third magnet rotor assembly is mounted at 7.5° with respect to horizontal as illustrated in FIG. 9I. Therefore, second helical gear 548 has a helix angle of 2.5° which equals 10° minus 7.5°.

Right handed second helical gear 548 is mounted on a shaft portion of the second rotor shaft end 549. Fourth magnet rotor assembly 994 is affixed to second rotor shaft end 470 and rotates therewith and second rotor shaft 470 is affixed to fourth helical gear 408 and rotates therewith. Second magnet rotor assembly 993 is affixed to second rotor shaft end 549 and rotates therewith and second rotor shaft end 549 is affixed to second helical gear 548 and rotates therewith.

Rotation of the shunt shaft 401 in the counter clockwise direction from the perspective of the first end is now described. Reaction of the gearing system which drives the magnet rotor assemblies 991, 992, 993, 994 is now described as well in connection with the counter clockwise rotation of shunt shaft 401.

FIG. 9H is a schematic perspective view 900H similar to FIG. 9C indicating rotation of the shunt drive shaft 401 in the counter clockwise direction 970 as defined from the perspective of the first end of the conduit sensor device and also indicating rotation of the propulsion drive shaft 550 in the counter clockwise direction 971 as defined from the perspective of the first end of the conduit sensor device.

Referring to FIGS. 9C and 9H, if shunt shaft 401 is rotated in the opposite direction, namely, counter clockwise 970 as indicated by arrow 970 when viewed from the first end of the conduit sensor device as illustrated in FIGS. 9C and 9H, then worm wheel 614 rotates in a counter clockwise direction as indicated by arrow 972 when viewed from above shaft 611. When shaft 401 is rotated counter clockwise 970 as defined, vertical worm 612 rotates counter clockwise as indicated by arrow 972A, first helical gear 514 rotates counter clockwise as indicated by arrow 973, and third helical gear 414 rotates clockwise as indicated by arrow 974.

Figure 9J:
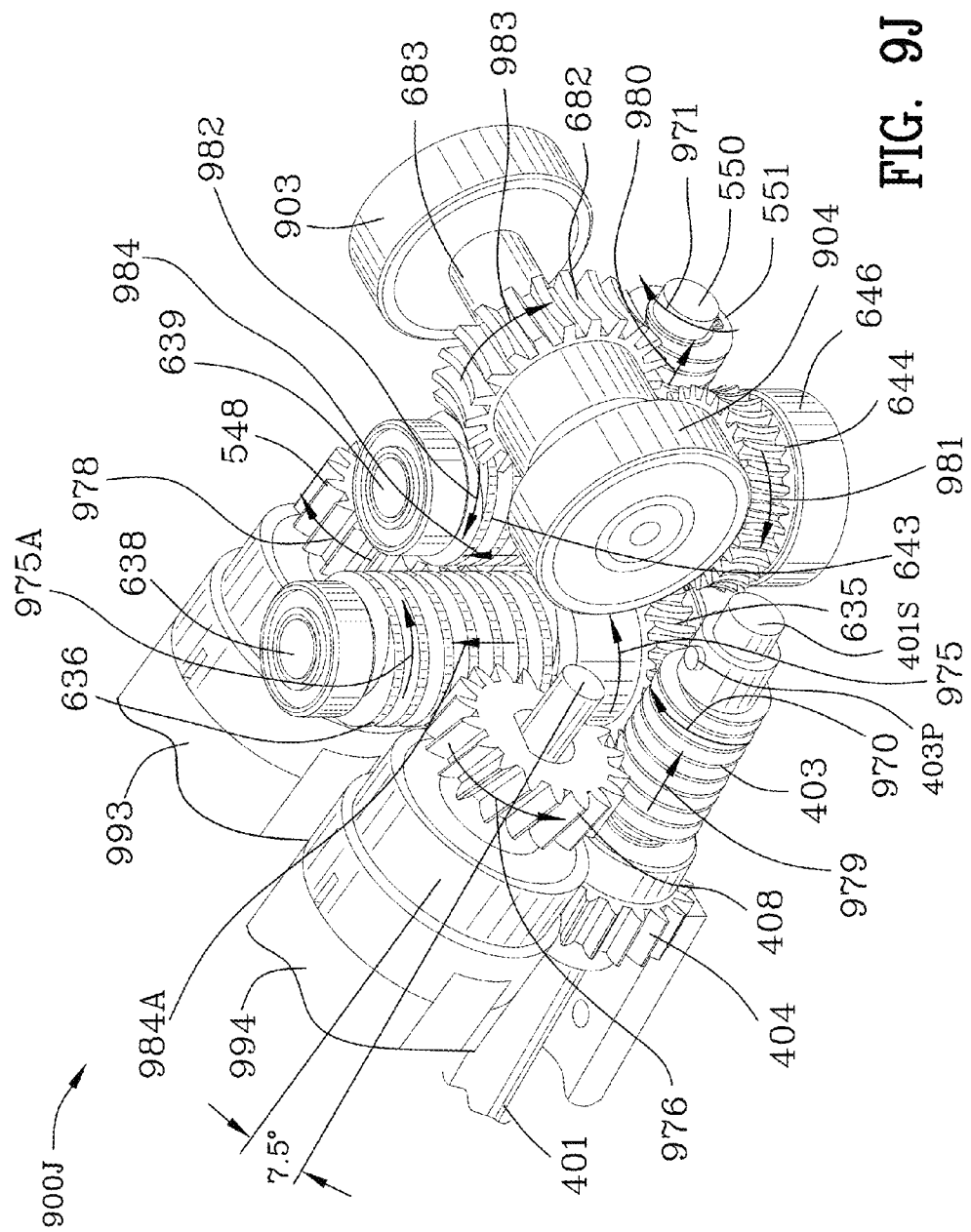
FIG. 9J is a schematic perspective view similar to FIG. 9D indicating rotation of the shunt drive shaft in the counter clockwise direction as defined from the perspective of the first end of the conduit sensor device and also indicating rotation of the propulsion drive shaft in the counter clockwise directions as defined from the perspective of the first end of the conduit sensor device.

FIG. 9J is a schematic perspective view 900J similar to FIG. 9D indicating rotation of the shunt drive shaft 401 in the counter clockwise 970 direction as defined from the perspective of the first end of the conduit sensor device and also indicating rotation of the propulsion drive shaft 550 in the counter clockwise 971 direction as defined from the perspective of the first end of the conduit sensor device. FIG. 9J illustrates the gearing system and magnet rotor assemblies 993, 994 of the second end of the device.

Referring to FIGS. 9D and 9J, if shunt shaft 401 is rotated in the counter clockwise 970 direction when viewed from the first end of the conduit sensor device as illustrated in FIG. 9C, then worm wheel 635 rotates in the counter clockwise 975 direction when viewed above shaft 638, and vertical worm 636 rotates in the counter clockwise 975A direction since worm 636 is locked to shaft 638 and worm wheel 635. When shaft 401 is rotated counter clockwise 970 as defined, worm wheel 635 rotates counter clockwise 975, fourth helical gear 408 rotates counter clockwise 976, and second helical gear 548 rotates clockwise 978. Arrow 979 indicates the direction of travel of worm wheel 635 with respect to worm 403. Arrow 979 is substantially tangent to helical gear 408, 548. Arrow 980 indicates the direction of travel of worm wheel 644 with respect to worm 551. Arrow 980 is substantially tangent to worm wheel 644.

FIG. 10 is a cross-sectional view 1000 taken along the lines 10-10 of FIG. 3. FIG. 10 illustrates the rotor assemblies 993, 994 in the normal or home position. In the normal or home position, the magnetic field 450 is strongest. FIGS. 4A and 5A illustrate the magnetic fields 450, 450A at their maximum extent. FIG. 4A illustrates rotor assemblies 992, 994 and FIG. 5A illustrates magnet rotor assemblies 991, 993. FIG. 9 clearly illustrates the rotor assemblies 991, 992, 993, 994 in their home position. FIG. 4A illustrates rotor assemblies 992, 994 in their home positions. Magnets 421, 422, 423, 424 of third magnet rotor assembly 992 are illustrated with their north poles 421N, 422N, 423N, 424N oriented facing upwardly toward pipe 499. Magnets 434, 435, 436, and 437 of fourth magnet rotor assembly 994 are illustrated with their south poles 434S, 435S, 436S and 437S oriented facing upwardly toward pipe 499. FIG. 5A illustrates magnet rotor assemblies 991, 993 in their home position. Magnets 525, 526, 527, 528 of rotor assembly 991 are illustrated with their north poles 525N, 526N, 527N, 528N oriented facing upwardly toward pipe 499. Magnets 530, 531, 532, 533 of second magnet rotor assembly 993 are illustrated with their south poles 530S, 531S, 532S, 533S oriented facing upwardly. FIGS. 4A and 5A illustrate magnet rotor assemblies 993, 994 oriented in the same position as FIG. 10. FIG. 10 illustrates the top portion 530T and the bottom portion 530B of second magnet rotor assembly 993, as well as magnet 530. Second magnet rotor assembly 993 is illustrated residing in cylindrically shaped housing 327 in backing bar weldment 302.

Although not visible in FIG. 10, the diameter of second magnet rotor assembly 993 is smaller than the diameter of the cylindrically shaped housing 327 such that second magnet assembly 993 rotates without engaging housing 327. Any incidental engagement that might occur is insignificant and does not impede the rotation of the second magnet rotor assembly 993. Similarly, propulsion drive shaft 550 resides within bore or passageway 331 in second backing bar weldment 302. The diameter of propulsion drive shaft 550 is less than the diameter of passageway 331 and, therefore, propulsion drive shaft 550 rotates freely within the passageway 331. Similarly, the shunt shaft 401 resides within passageway 377. Passageway 377 extends from the first end of the backing bar weldment 301 to the second end of the backing bar weldment 301 as illustrated in FIG. 4A. The diameter of the shunt shaft 401 is smaller than the diameter of the passageway 377.

FIG. 10A is a cross-sectional view 1000A taken along the lines 10-10 of FIG. 3, with shunt shaft 401 rotated counter clockwise and with the rotor assemblies 993, 994 of the second end rotated 90° to the position where the magnetic fields are cancelled. When shaft 401 is rotated counter clockwise as defined, worm wheel 635 rotates counter clockwise, fourth helical gear 408 rotates counter clockwise, and second helical gear 548 rotates clockwise. See FIG. 9J. Then magnet rotor assemblies 993, 994 and magnets 530, 434 are positioned in their second position as illustrated in FIG. 10A with sufficient rotation of shaft 401. Shaft 401 is driven by the shunt motor 698 which drives shaft 698S which drives shunt shaft output gear 631. See FIG. 6B. Shunt shaft output gear 631 engages shunt shaft mounted gear 404. Shunt motor 698 may be a single direction motor or the motor may be bidirectional. Shunt motor 698 may be a stepper motor. Motor control is necessary to control the positioning of the magnet rotor assemblies, and, hence the strength of the magnetic field between the first end and the second end of the device. A specific number of revolutions of the shunt drive shaft 401 equates to a specific number of revolutions of the vertical worms 612, 636. A specific number of revolutions of the vertical worm 612 equates to a specific number of revolutions, or fractional part thereof, of first helical gear 514 and third helical gear 414. Further, a specific number of revolutions of the vertical worm 636 equates to a specific number of revolutions, or fractional part thereof, of second helical gear 548 and fourth helical gear 408. Therefore, control of the shunt shaft 401 dictates control and position of the magnet rotor assemblies 991, 992, 993, 994. The control system is responsible for rotating the magnets between the first position, 0° rotation as shown in FIGS. 9, 9C, 9D, 10, and 11 to the second position illustrated in FIGS. 5B, 10A, and 11A, 90° rotation based on counter clockwise rotation of shunt shaft 401.

Reference is made to FIGS. 4A and 5A wherein the field strengths 450, 450A are illustrated at their maximum. FIG. 10A illustrates the position of the magnet rotor assemblies 993, 994 as a result of counter clockwise rotation of shunt shaft 401 to the shunt position or cancellation position. The position of the magnet rotor assemblies 991, 992, 993, 994 is dependent on the positioning of shunt shaft 401 which drives shaft-mounted worms 402, 403. The magnetic field 1001, 1002 of the second magnet rotor assembly 993 is shown in FIG. 10A. The magnetic field 1003, 1004 of the fourth magnet rotor assembly 994 is shown in FIG. 10A. In the position illustrated in FIG. 10A, the magnet rotor assemblies do not create a magnetic field in pipe 499; rather, the magnetic fields of the magnet rotor assemblies 993, 994 are shunted meaning there is no magnetic field between the first and second ends of the conduit sensor device as illustrated in FIGS. 4A and 5A.

Referring to FIGS. 10, 10A, 11, and 11A, reference numeral 1010 signifies and indicates the rear or rearward portion of the conduit sensor device. Reference numeral 1011 signifies and indicates the front or forward portion of the conduit sensor device. Reference numeral 1012 signifies and indicates the central portion of the conduit sensor device.

FIG. 11 is a cross-sectional view 1100 taken along the lines 11-11 of FIG. 3. FIG. 11A is a cross-sectional view 1100 taken along the lines 11-11 of FIG. 3 with the rotor assemblies 991, 992 of the first end rotated 90° with shunt shaft 401 rotated counter clockwise. See FIGS. 9H and 9J.

When magnet rotor assemblies 993, 994 are driven to the shunt position of FIG. 10A, the magnet rotor assemblies 991, 992 are simultaneously driven to the shunt position of FIG. 11A. Shunt shaft 401 drives the magnet rotor assemblies 991, 992 of the first end simultaneously with the magnet rotor assemblies 993, 994 of the second end. FIG. 11A is a cross-sectional view 1100A taken along the lines 11-11 of FIG. 3 with the rotor assemblies 993, 994 of the second end rotated 90° to the position where the magnetic fields are cancelled. Reference is made to FIGS. 4A and 5A wherein the field strengths 450, 450A are illustrated at their maximum.

When shaft 401 is rotated counter clockwise as defined and illustrated in FIGS. 9H and 9J, vertical worm 612 rotates counter clockwise, first helical gear 514 rotates counter clockwise, and third helical gear 414 rotates clockwise. FIG. 11A illustrates the position of the magnet rotor assemblies 991, 992 as a result of counter clockwise rotation of shunt shaft 401 to the shunt position or cancellation position, for example a 90° rotation of the magnet rotor assemblies. The terms "shunt position" and "cancellation position" are also known as the "second position." FIGS. 9, 9C, 9D, 10, and 11 illustrate the magnet rotor assemblies 991, 992, 993, and 994 in their first positions (0° rotation).

The magnetic field 1101, 1102 of the second magnet rotor assembly 993 is shown in FIG. 10A. The magnetic field 1103, 1104 of the fourth magnet rotor assembly 994 is shown in FIG. 11A. In the position illustrated in FIG. 11A, the magnet rotor assemblies do not create a magnetic field in pipe 499; rather, the magnetic fields of the magnet rotor assemblies 991, 991 are shunted meaning there is no magnetic field between the first and second ends of the conduit sensor device as illustrated in FIGS. 4A and 5A.

The magnet rotor assemblies 991, 992, 993, 994 include top portions and bottom portions as described herein wherein the top and bottom portions, magnets and pins together with the rotor ends form the assemblies. The top and bottom portions of each of the magnet rotor assemblies 991, 992, 993, 994 are ferromagnetic. Further, the first and second backing bar weldments 301, 302 are ferromagnetic. First and second backing bar weldments 301, 302 are made of 1008 steel capable of carrying a higher magnetic field than typical 1018 steel.

FIGS. 4A and 5A are schematic cross-sectional views of the conduit sensor device with magnetic field lines 450 illustrated. The invention is not limited in any way by the size of the magnets or the magnet rotor assemblies.

Referring to FIGS. 4A and 5A, the home position of the rotatable magnets is illustrated. The home position of the rotatable magnets is also shown in FIGS. 4 and 5. The pipe wall 499 is illustrated with a thickness and the magnetic fields 450, 450A are illustrated passing entirely through the wall of the pipe 499.

FIG. 5 is a cross-sectional view 500 taken along the lines 5-5 of FIG. 3A. Line 5-5 is taken along the centerline of the propulsion drive shaft 550. FIG. 5A is a cross-sectional view 500A taken along the lines 5-5 of FIG. 3A with a pipe in the view. FIG. 5B is a cross-sectional view 500B taken along the lines 5-5 of FIG. 3A with rotor assemblies rotated 90°. No polarities of the magnets are noted in FIG. 5B as the magnets are shown in cross section as are the pins which hold the magnets in place. The pins are press-fitted into the top and bottom portions of the magnet rotor assembly. In the position illustrated in FIG. 5B, there is no magnetic field between first magnet rotor assembly 991 and second magnet rotor assembly 993 as the magnetic fields have been shunted (canceled) as illustrated in FIGS. 10A and 11, and, as such there is no magnetic field shown in FIG. 5B.

Line 5-5 of FIG. 3A is not coincident with the centerline of magnet rotor assemblies 991, 993. Propulsion drive shaft 550 resides slightly inwardly of the centerline of magnet rotor assemblies 991, 993. Propulsion drive shaft 550 is sometimes referred to herein as just the propulsion shaft 550. FIG. 5 illustrates the magnet rotor assemblies 991, 993 in their home or normal position. In the normal position the magnets of rotor assembly 991 are oriented such that the north poles 525N, 526N, 527N, 528N of the magnets 525, 526, 527, 528 are oriented facing upwardly. In the normal position the magnets of second magnet rotor assembly 993 are oriented such that the south poles 530S, 531S, 532S, 533S are oriented facing upwardly. Reference is made to FIG. 5A, wherein magnetic field 450 is illustrated for the normal position of magnet rotor assemblies 991, 993. Pipe 499 is illustrated with field lines 450 passing therethrough. As illustrated in FIG. 5A, wheels 107, 108 are illustrated in engagement with pipe 499. Sensors 106 detect abnormalities or defects anywhere in the pipe 499.

Still referring to FIGS. 5 and 5A, propulsion drive shaft 550 is illustrated in cross-section. FIG. 5A also illustrated worms 558, 551 and shaft bearings 560, 553. Magnet rotor assemblies 991, 993 are illustrated within cylindrical housings 326, 327 in second backing bar weldment 302. Cylindrical opening 590D in backing bar weldment 302 is illustrated with rotor end 590 slip-fitted therein so as to permit rotation of rotor end 590 with respect to the cylindrical opening 590D. Similarly, cylindrical opening 591D in backing bar weldment 302 is illustrated with rotor end 591D slip-fitted therein so as to permit rotation of rotor end 591D with respect to cylindrical opening 591D. Rotor assemblies 991, 993 are substantially cylindrically-shaped and have a diameter slightly smaller than cylindrical housings 326, 327 in which they reside. The magnetic field 450A generated by the first magnet rotor assembly 991 and the second magnet rotor assembly 993 is illustrated in FIG. 5A. The magnetic field 450 generated by the second magnet rotor assembly 992 and the fourth magnet rotor assembly 994 is illustrated in FIG. 4A.

Still referring to FIGS. 5 and 5A, the entire length of propulsion drive shaft 550 is viewed as is spur gear 555 affixed to propulsion drive shaft 550 by snap rings 561S, 562S and a set screw 527. FIGS. 8, 8A, 8B, 8C, 8D and 8E illustrate the propulsion drive shaft 550, worms 558, 551 and their mounting on the propulsion drive shaft 550, bearings 560, 553 which support the shunt shaft 550, and spur gear 555. Spur gear 555 is driven by propulsion motor spur gear 620 as best viewed in FIG. 9A. FIG. 9A is a bottom view of the first end of the conduit sensor device. The propulsion drive motor spur gear 620 is driven by the propulsion motor 620A as illustrated in FIG. 6A. Referring to FIG. 5A, bearing 560 resides between support 306S in the gear box half 306 and support 309K in bottom plate 309. Bearing 553 similarly supports shaft 550 on the second end thereof between an unnumbered support in gear box 308 and an unnumbered support in bottom plate 310.

A process for modifying a magnetic field of a conduit sensor device is disclosed. The conduit sensor is in proximity to a ferromagnetic conduit. The steps of the process include: driving a shunt shaft having first and second worms affixed thereto and rotating therewith; rotating, using the first worm, a first worm wheel and a first vertical worm affixed thereto; rotating, using the first vertical worm, a first helical gear and a first magnet rotor assembly affixed to the first helical gear; rotating, using the second worm, a second worm wheel and a second vertical worm affixed thereto; and, rotating, using the second vertical worm, a second helical gear and a second magnet rotor assembly affixed to the second helical gear. Preferably, the process includes rotating, using the first vertical worm, a third helical gear and a third magnet rotor assembly affixed to the third helical gear; and, rotating, using the second vertical worm, a fourth helical gear and a fourth magnet rotor assembly affixed to the fourth helical gear.

According to the process for modifying the magnetic field, the steps of rotating the first, second, third and fourth magnet assemblies may include rotating the magnet assemblies from a first position wherein a magnetic field exists between the first magnet assembly and the second magnet assembly and from a first position wherein a magnetic field exists between the third magnet assembly and the fourth magnet assembly to a second position wherein no magnetic field exists between the first magnet assembly and the second magnet assembly and wherein no magnetic field exists between the third magnet assembly and the fourth magnet assembly.

According to the process for modifying the magnetic field, the shunt shaft may be rotated bidirectionally. The first, second, third and fourth magnet assemblies may be rotated 90° to their second position. Each of the magnet rotor assemblies includes a plurality of magnets and the magnet rotor assemblies are housed and supported in first and second backing bar weldments. According to the process, the rotation of the first and third magnet rotor assemblies residing at a first end of the device and the rotation of the second and fourth magnet rotor assemblies residing at a second end of the device is performed synchronously.

Alternatively according to the process the steps of rotating the first, second, third and fourth magnet assemblies may include rotating the magnet assemblies less than 90°: from a first position wherein a maximum strength magnetic field exists between the first magnet assembly and the second magnet assembly; and, from a first position wherein a maximum strength magnetic field exists between the third magnet assembly and the fourth magnet assembly, to an intermediate position wherein a lower strength magnetic field exists between the first magnet assembly and the second magnet assembly and wherein a lower strength magnetic field exists between the third magnet assembly and the fourth magnet assembly.

Operation of the propulsion drive system is now described in greater detail.

Referring to FIGS. 9, 9A, 9B, 9C and 9D, right handed worms 558, 551 are mounted on shaft 550. On the first end, worm 558 engages worm wheel 608. on the second end, worm 551 engages worm wheel 644.

Clockwise rotation of propulsion shaft 550 from the perspective of the first end is now described.

FIG. 9G is a schematic perspective view 900G of FIG. 9C indicating rotation of the propulsion drive shaft 550 in the clockwise direction 951 as defined and viewed from the perspective of the first end of the conduit sensor device.

Referring to FIGS. 9, 9C and 9G, as worm 558 rotates clockwise 951 when viewed from the first end to the second end, worm wheel 608 rotates counter clockwise 956 from the perspective of FIG. 9. Arrow 960 indicates the direction of travel of the worm wheel 608 with respect to worm 558 when shaft 550 and worm 558 are rotated clockwise 951 as defined herein. Arrow 960 is substantially tangent to worm 558. As shaft 550 rotates clockwise 951, then vertical worm 605 rotates counter clockwise 957 from the perspective of FIG. 9, specifically, from above the first end. As worm 605 rotates counter clockwise 957 then gear 680 rotates counter clockwise 958 along its shaft as viewed in FIGS. 9C and 9G from right to left and in FIG. 6A. As gear 680 is affixed to wheel shaft 681, and as wheels 107, 107A are affixed to wheel shaft 681 and rotate therewith, the conduit sensor device will be propelled rightwardly when viewing FIGS. 6, 6A, 6B and 9.

FIG. 9I is a schematic perspective view 900I similar to FIG. 9D indicating rotation of the propulsion drive shaft 550 in the clockwise direction 951 as defined from the perspective of the first end of the conduit sensor device.

Referring to FIGS. 9, 9D and 9I, if propulsion drive shaft 550 rotates clockwise 951 when viewed from the first end toward the second end, then worm 551 also rotates clockwise 951 as worm 551 is affixed to shaft 550. Worm 551 and worm wheel 644 driven by worm 551 are right handed. Vertical worm 643 and worm wheel 682 are left handed and these are the only two left handed worm and worm wheel disclosed here. All other worms and worm wheels are right handed. Vertical worm 643 and worm wheel 682 are left handed so that worm wheels 680, 682 rotate in the same direction. Other gearing arrangements and combinations may be used. As worm 551 rotates clockwise 951 then worm wheel 644 rotates counter clockwise 961 when viewed from above the conduit sensor device as illustrated in FIGS. 9, 9D and 9I. Referring to FIG. 9B, a bottom view of the second end of the conduit sensor device, reference is made to worm 551 in meshed engagement with worm wheel 644. From the perspective of FIG. 9B, worm wheel 644 rotates clockwise when worm 551 is rotating clockwise with respect to the first end of the device. Arrow 964 in FIG. 9I indicates the direction of travel of worm wheel 644 with respect to worm 551. Arrow 964 is substantially tangent to worm wheel 644.

Referring to FIGS. 9, 9D and 9I, as worm wheel 644 rotates counter clockwise from the perspective of FIG. 9, then vertical worm 643 rotates counter clockwise 962 from the perspective of FIG. 9. As vertical worm 643 rotates counter clockwise 962, then wheel gear 682 rotates counter clockwise 963 along its shaft as viewed from left to right in FIGS. 9D and 9I. As gear 682 is affixed to wheel shaft 683, and as wheels 108, 108A are affixed to wheel shaft 683 and rotate therewith, the conduit sensor device will be propelled rightwardly when viewing FIGS. 6, 6A, 6B and 9.

Counter clockwise rotation of the propulsion shaft 550 from the perspective of the first end is now described.

FIG. 9H is a schematic perspective view 900H similar to FIG. 9C indicating rotation of the shunt drive shaft 401 in the counter clockwise direction 971 as defined from the perspective of the first end of the conduit sensor device and also indicating rotation of the propulsion drive shaft 550 in the counter clockwise 971 direction as defined from the perspective of the first end of the conduit sensor device.

Referring to FIGS. 9, 9C and 9H, as worm 558 rotates counter clockwise 971 when viewed from the first end to the second end, worm wheel 608 rotates clockwise 985 from the perspective of FIG. 9. As shaft 550 rotates counter clockwise 971, then worm 605 rotates clockwise 987 from the perspective of FIG. 9. Arrow 986 indicates the direction of travel of worm wheel 608 with respect to worm 558. Arrow 986 is substantially tangent to worm wheel 608.

As worm 605 rotates clockwise 987, then gear 680 rotates clockwise 988 along its shaft as viewed in FIGS. 9C and 9H. Reference numeral 987A indicates the direction of travel of the teeth of worm wheel 680 with respect to worm 605. Arrow 987 is substantially tangent to worm wheel 680. As worm wheel 680 is affixed to wheel shaft 681, and as wheels 107, 107A are affixed to wheel shaft 681 and rotate therewith, the conduit sensor device will be propelled leftwardly when viewing FIGS. 6, 6A, 6B and 9.

FIG. 9J is a schematic perspective view 900J similar to FIG. 9D indicating rotation of the propulsion drive shaft 550 in the counter clockwise direction as defined from the perspective of the first end of the conduit sensor device.

Referring to FIGS. 9, 9D and 9J, if propulsion drive shaft 550 rotates counter clockwise 971 when viewed from the first end toward the second end, then worm 551 also rotates counter clockwise 971 as worm 551 is affixed to shaft 550. As worm 551 rotates counter clockwise 971 then worm wheel 644 rotates clockwise 981 when viewed from above the conduit sensor device as illustrated in FIGS. 9, 9D and 9J. Referring to FIG. 9B, a bottom view of the second end of the conduit sensor device, reference is made to worm 551 in meshed engagement with worm wheel 644. From the perspective of FIG. 9B, worm wheel 644 rotates counter clockwise.

Referring to FIGS. 9, 9D and 9J, as worm wheel 644 rotates clockwise from the perspective of FIG. 9, then vertical worm 643 rotates clockwise 982 from the perspective of FIG. 9. As vertical left-handed worm 643 rotates clockwise, then left-handed worm wheel 682 rotates clockwise 983 along its shaft, as viewed from left to right in FIGS. 9D and 9J. Arrow 984 indicates the direction of travel of worm wheel 682 with respect to vertical left-handed worm 643. Arrow 984A indicating the direction of travel of helical gears 408, 548 with respect to worm 636. As gear 682 is affixed to wheel shaft 683, and as wheels 108, 108A are affixed to wheel shaft 683 and rotate therewith, the conduit sensor device will be propelled leftwardly when viewing FIGS. 6, 6A, 6B and 9.

A method of operating a conduit sensor device which propels the device within a conduit includes the steps of: rotating a propulsion shaft having first and second worms affixed thereto and rotating therewith; rotating, using the first worm, a first worm wheel and a first vertical worm affixed thereto; rotating, using the first vertical worm, a first drive wheel worm having a first drive wheel affixed thereto; rotating, using the second worm, a second drive worm wheel and a second vertical worm affixed thereto; and, rotating, using the second vertical worm, a second drive worm wheel having a second drive wheel affixed thereto. Also, a step of: synchronizing the first and second drive wheels.

REFERENCE NUMERALS

100—perspective view of a plurality of conduit sensor device with a plurality of sensors and magnetic shunts
101—arrow pointing to one conduit sensor with magnetic shunt
102—couplings
103—tubular radial control mechanism
103A, 103B—wire/rod for extending the conduit sensors
104—arrow indicating second end of one conduit sensor with magnetic shunt
105—arrow indicating first end of one conduit sensor with magnetic shunt
106—electronic sensors used to detect anomalies and defects in pipe
107A, 107B, 108A, 108B—propulsion wheels
109—drive units
200—enlargement of a portion of FIG. 1 illustrating the tubular radial control mechanism and a conduit sensor with magnetic shunt
201—spring
300—perspective view of conduit sensor with magnetic shunt
300A—top view of conduit sensor with magnetic shunt
300B—side view of conduit sensor with magnetic shunt
300C—first end view of conduit sensor with magnetic shunt
300D—second end view of conduit sensor with magnetic shunt
300E—perspective view of the second backing bar weldment of the conduit sensor with magnetic shunt
300F—another perspective view of the second backing bar weldment of the conduit sensor with magnetic shunt
300G—end view of the second backing bar weldment of the conduit sensor with magnetic shunt
300H—perspective view of the second half of the gear housing of the first end of the conduit sensor with magnetic shunt
300I—another perspective view of the second half of the gear housing of the first end of the conduit sensor with magnetic shunt
300J—is a perspective view of the first half of the gear box of the first end of the conduit sensor device with magnetic shunt
300K—is a perspective view of the first half of the gear box of the first end of the conduit sensor device with magnetic shunt
300L—is a plan view of the wheel propulsion drive shaft of the first end together with the drive gear
300M—is a plan view of the wheel propulsion drive shaft of the first end.
300N—perspective view of the bottom plate of the first end of conduit sensor with magnetic shunt
300O—another perspective view of the bottom plate of the first end of conduit sensor with magnetic shunt
301—first backing bar weldment
302—second backing bar weldment
303—first center roller
304—second center roller
305—first end gear box half
305A—wheel well
305B—semi-cylindrical shunt gear housing in the first end gear box half 305
305C—semi-cylindrical drive gear housing in the first end gear box half 305
305D—opening for gear 680
305E—end surface in gear box half 305
305F, 305H, 305J—shoulder
305G—passageway for shaft
305L—seat for propulsion wheel bearing 902
305S—bearing support for shunt shaft bearing 416
305R—opening for the shunt shaft and worm 402 in gear box half 305
305W—seat for bearing 412 which supports third magnet rotor assembly 992
306—first end gear box
306A—wheel well
306B—semi-cylindrical shunt gear housing in the first end gear box half 306
306C—semi-cylindrical drive gear housing in the first end gear box half 306
306D—bearing mount/well in gear box 306
306F—bearing seat
306K—upper shoulder in the gear box limiting the shunt worm's upper movement
306L—bearing seat, upper bearing, shunt worm
306M—upper shoulder in the gear box limiting the drive worm's upper movement
306N—bearing seat, upper bearing, drive worm
305S—bearing support for propulsion shaft bearing 560
306R—opening for the propulsion shaft and worm 558 in gear box half 306
306X—bearing seat in first end gear box half, 306, and opening for the rotor shaft end 515
306Y—shoulder in gear box half 306 which limits movement of the shunt worm wheel 614
306Z—shoulder in gear box half 306 which limits movement of the drive worm wheel 608
307—second end gear box half
307A—wheel well
307X—bearing seat for bearing 407 in second end gear box half, 307
308—second end gear box side plate
308A—wheel well
308X—bearing seat for bearing 547 in second end gear box half 308
309—first end gear box bottom plate
309A—opening in first end gear box bottom plate which houses shunt shaft worm 402
309B—opening in first end gear box bottom plate which houses drive shaft worm 558
309C—cylindrical wall in base plate 309
309G—lip in base plate 309
309H—shoulder
309S—shoulder supporting lower bearing 609A for shunt worm wheel 614 which drives vertical shunt worm wheel 612
309K, 309L—bearing support in end plate
309W—cylindrical wall in base plate 309
310—second end gear box bottom plate
311—base plate
311A—first end of base plate 311

311B—second end of base plate 311
312—rotor
313—rotor
320—flat interior face of second backing bar weldment
321—pin mounting
322—recess in second backing bar weldment
323—flat surface of second backing bar weldment
324—wall of wire slot
326—housing in second backing bar weldment for rotatable magnets
326C—circular opening in end surface 326E
326E—end surface in housing 326 in second backing bar weldment
327—housing in second backing bar weldment for rotatable magnets
328—slot in second backing bar weldment
329—recess in second backing bar weldment for motor housing of propulsion motor
330—recess in second backing bar weldment for motor housing of magnet motor
331—passageway for propulsion drive shaft
340—access port for adjustment of threaded stud 402N for adjustment of thrust bearing 402B of magnet shaft
340S—guide groove in first end gear box half 305 which receives guide pin 415S
341—access port for adjustment of threaded stud 403N for adjustment of thrust bearing 403B of magnet shaft
341S—guide groove in second end gear box half 307 which receives guide pin 418S
389, 305H—bearing shoulder
399G—lip in base plate 309
399S—shoulder supporting lower bearing 609 for drive worm wheel 608 which drives vertical shunt worm 605
400—cross-sectional view taken along the line 4-4 of FIG. 3A
400A—cross-sectional view taken along the line 4-4 of FIG. 3A
401—magnet drive shaft
401F, 401S—end of magnet drive shaft
402—first end magnet drive shaft worm
402B—thurst bearing of magnet drive shaft 401
402C—partial cylinder
402G—grip of threaded stud 402N
402K—cylindrical portion of partial cylinder
402N—threaded stud 402N for adjustment of thrust bearing 402B
402R—bore in partial cylinder 402C
402S—shoulder on magnet drive shaft limiting movement of worm 402
402T—threads in adjustment bore 402R
402Z—flat portion of partial cylinder 402C providing room for worm wheel 608
403—second end magnet drive shaft worm
403B—thrust bearing of magnet shaft 401
403C—partial cylinder
403G—grip of threaded stud 403N
403N—threaded stud 402N for adjustment of thrust bearing 402B
403P—pin locking rotation of first end magnet drive shaft worm 403 with magnet drive shaft 401
403R—bore in partial cylinder 403C
403S—shoulder on magnet drive shaft limiting movement of worm 403
403T—threaded hole
404—spur gear and set screw affixed to magnet drive shaft 401
405—motor shunt support
406—bearing supporting second end shaft worm 403 and magnet drive shaft 401
407—bearing supporting fourth magnet rotor assembly 994
408—fourth helical gear driving fourth magnet rotor assembly 994
410—rotor shaft end of fourth magnet rotor assembly 994 distally located with respect to second end gear drive system
410D—circular opening in cylindrical housing 426 in backing bar weldment 301
410S—snap ring securing rotor shaft end of fourth magnet rotor assembly 994
411—rotor shaft end of third magnet rotor assembly 992 distally located with respect to second end gear drive system
411D—circular opening in cylindrical housing 427 in backing bar weldment 301
412—bearing supporting third magnet rotor assembly 992
413—third rotor shaft end of third magnet rotor assembly 992
414—third helical gear driving third magnet rotor assembly 992
415—pin locking rotation of first end magnet drive shaft worm 402 with magnet drive shaft 401
415S—pin preventing rotation of partial cylinder 402C
416—bearing supporting first end shaft worm 402 and magnet drive shaft 401
416S—snap-ring securing bearing 416
417S—snap-ring securing bearing 416
418S—pin preventing rotation of partial cylinder 403C
419C—cupped surface on end of threaded stud 402N for adjustment of thrust bearing 402B
420C—cupped surface on end of threaded stud 403N for adjustment of thrust bearing 403B
421, 422, 423, 424—magnets of third magnet rotor assembly 992
421B—bottom portion of third magnet rotor assembly 992
421N, 422N, 423N, 424N—north pole of magnets in third magnet rotor assembly 992
421P, 422P, 423P, 424P—pins securing magnets in third magnet rotor assembly 992
421S, 422S, 423S, 424S—south pole of magnets in third magnet rotor assembly 992
421T—top portion of third magnet rotor assembly 992
426, 427—cylindrical housing in first backing bar weldment 301
434T—top portion of fourth magnet rotor assembly 994
434B—bottom portion of fourth magnet rotor assembly 994
434, 435, 436, 437—magnets of fourth magnet rotor assembly 994
434, 435H, 436H, 437H—holes in magnets
434L—lower lip of bottom portion 434B of third magnet rotor assembly 992 in which rotor shaft end fits
434N, 435N, 436N, 436N—north pole of magnets in fourth rotor assembly 994
434P, 435P, 436P, 437P—pins securing magnets in fourth magnet rotor assembly 994
434S, 435S, 436S, 437S—south pole of magnets in fourth magnet rotor assembly 994
434U—upper lip of top portion 434T of fourth magnet rotor assembly 994
438—snap-ring securing spur gear 404 axially on magnet drive shaft
438S—set screw for spur gear 404
434T—top portion of fourth magnet rotor assembly 994
439—snap ring securing bearing 406

450—lines of magnetic field between magnets 421, 422, 423, 424 and 434, 435, 436, 437
453S—snap ring securing bearing 406
470—rotor shaft end for fourth magnet rotor assembly 994
471—retaining slot for magnet 437
471C—semi-circumferential lip engaging rotor shaft end 470
472—retaining slot for magnet 437
473—circumferentially shaped lip of rotor shaft end 470
474—shaft portion of rotor shaft end 470
475—locking flat portion of shaft portion 474
476—locking flat portion of fourth helical gear 408
481, 482, 483, 484—hole for pins through top portion 434T and bottom portion 434B of rotor magnet assembly 994
491—rotor shaft distal end of magnet rotor assembly 993
491S—snap-ring restraining rotor shaft end 491
499—pipe or conduit under inspection
500—cross-sectional view taken along the lines 5-5 of FIG. 3A
500A—cross-sectional view taken along the lines 5-5 of FIG. 3A with a pipe in the view
500B—cross-sectional view taken along the lines 5-5 of FIG. 3A with rotor assemblies 991, 991 rotated 90°
514—first helical rotor shaft gear driving rotor assembly 991
515—first end rotor shaft end proximate gear drive system of rotor assembly 991
516—bearing supporting rotor assembly 991
525, 526, 527, 528—magnets in magnet rotor assembly 991
525B—bottom of magnet rotor assembly 991
525N, 526N, 527N, 528N—north pole of magnets in magnet rotor assembly 991
525S, 526S, 527S, 528S—south pole of magnets in magnet rotor assembly 991
525P, 526P, 527P, 528P—pins securing magnets in magnet rotor assembly 991
525T—top of magnet rotor assembly 991
530, 531, 532, 533—magnets in second magnet rotor assembly 993
530B—bottom of second magnet rotor assembly 993
530H, 531H, 532H, 533H—holes in magnets
530L—lower lip of bottom portion 530B of second magnet rotor assembly 993 in which rotor shaft end fits
530N, 531N, 532N, 533N—north pole of magnets in second magnet rotor assembly 993
530P, 531P, 532P, 533P—pins securing magnets in second magnet rotor assembly 993
530S, 531S, 532S, 533S—south pole of magnets in second magnet rotor assembly 993
530T—top of second magnet rotor assembly 993
530U—upper lip of top portion 530T of fourth magnet rotor assembly 994
547—bearing supporting second magnet rotor assembly 993
548—second helical gear driving fourth magnet rotor assembly 994
549—rotor shaft end of second magnet rotor assembly 993 residing at the second end of the device
550—propulsion drive shaft
551—second end propulsion drive shaft worm
552—pin locking rotation of second end propulsion shaft worm 551 with propulsion drive shaft 550
552S—slot in second end propulsion drive shaft worm 551
553—bearing supporting second end shaft worm 551 and propulsion drive shaft 550
553S, 554S—snap ring securing bearing 553 to propulsion drive shaft 550
555—spur gear driven by gear 620 driven by propulsion motor
556S, 561S—snap-rings securing bearing 560
557—pin locking rotation of first end prolusion shaft worm 558 with propulsion drive shaft 550
557S—slot in first end prolusion drive shaft worm 558
558—first end propulsion drive shaft worm
559—snap ring securing first end propulsion drive shaft worm 558
560—bearing supporting first end shaft worm 558 and propulsion drive shaft 550
562S—snap-ring securing spur gear 555 on propulsion drive shaft 550
570S—snap ring securing second end propulsion drive shaft worm 551
571—retaining slot for magnet 533
571C—semi-circumferential lip engaging rotor shaft end 549
572—retaining slot for magnet 533
573—circumferentially shaped lip of rotor shaft end 549
574—shaft portion of rotor shaft end 570
576—locking flat portion of second helical gear 548
575—locking flat of shaft 574 of magnet rotor assembly
581, 582, 583, 584—hole for pins through top portion 530T and bottom portion 530B of rotor assembly 993
587—shunt motor spur gear
590—rotor shaft end of rotor assembly 991 distally located with respect to first end gear drive system
590D—circular opening in cylindrical housing 326 in backing bar weldment 302
591—rotor shaft end of rotor assembly 993 distally located with respect to second end gear drive system
591D—circular opening in cylindrical housing 327 in backing bar weldment 302
597—set screw for spur gear 555
600—cross-sectional view taken along the line 6-6 of FIG. 3A
600A—enlargement of a portion of FIG. 6
600B—enlargement of a portion of FIG. 6A
601—gearbox which includes halves 305, 306
602—gearbox which includes halves 307, 308
603—upper bearing supporting drive shaft 604
604—drive shaft for drive worm wheel 608 and vertical drive worm 605 which rotates wheel drive gear 680
605—vertical drive worm for rotating wheel drive gear 680
606—pin securing drive worm wheel 608 to drive shaft 604
607—pin slot in drive shaft 604
608—drive worm wheel engaging drive shaft worm 558
609—bearing supporting drive worm wheel 608
609A—bearing supporting shunt worm wheel 614
610—upper bearing supporting drive shaft 611
611—drive shaft for vertical shunt worm wheel 612 which rotates magnet rotor assemblies 991, 992
612—vertical shunt worm which rotates magnet rotor assemblies 991, 992
613—pin securing shunt worm wheel 614 to drive shaft 611
614—shunt worm wheel engaging shunt shaft worm 402
615—spacer between bearing 609A and shunt worm wheel 614
615A—spacer between vertical shunt worm wheel 612 and upper bearing 610
616—propulsion motor support
617—spacer between bearing 609 and drive worm wheel 608
617A—spacer between vertical shunt worm 605 and upper bearing 603
620—motor driven spur gear
620A—propulsion motor
621—motor support 622—motor shaft bearing
630—shunt motor support
631—shunt motor driven gear
632—shunt motor shaft bearing
633—bearing supporting shunt worm wheel 635
634—spacer between bearing 633 and shunt worm wheel 635
634A—spacer between bearing 637 and vertical worm shunt worm 636
635—shunt worm wheel engaging shunt shaft worm 403
636—vertical shunt worm for rotating the magnet rotor assemblies 993, 994
637—upper bearing supporting drive shaft 638
638—drive shaft for vertical shunt worm wheel 635 which rotates magnet rotor assemblies 993, 994
639—drive shaft for drive worm wheel 644 and vertical drive worm 643 which rotates wheel drive gear 682
640—upper bearing supporting drive shaft 639
641—pin securing shunt worm wheel 635 to drive shaft 638
642—pin securing shunt worm wheel 644 to drive shaft 639
643—vertical drive worm for rotating wheel drive gear 682
644—drive worm wheel engaging drive shaft worm 551
645—spacer between bearing 646 and drive worm wheel 644
645A—spacer between bearing 640 and drive worm 643
646—bearing supporting drive worm wheel 644
680, 682—propulsion wheel drive gear
680F, 682F—integral collar for affixation of drive gear to propulsion wheel drive shaft
681, 683—propulsion wheel drive shaft
681S, 681H—bearing restraining shoulders on shaft 681
698—shunt motor
698S—shunt motor shaft
699—bolt hole
700—plan view of magnet drive shaft 401, first end worm 402, spur gear 404 affixed to shaft 401 and second end worm 403
700A—cross-sectional view taken along the lines 7A-7A of FIG. 7
700B—enlargement of the first end portion of FIG. 7
700C—cross-sectional enlargement of the first end portion of FIG. 7
700D—enlargement of the second end portion of FIG. 7
700E—cross-sectional enlargement of the second end portion of FIG. 7
700E—is a top view of partial cylinder which provides thrust bearing support for the magnet drive shaft.
700G—is an end view of the partial cylinder which provides thrust bearing support for the magnet drive shaft.
800—plan view of magnet drive shaft 550, first end worm 558, spur gear 555 affixed to shaft 550 and second end worm 551
800A—cross-sectional view taken along the lines 8A-8A of FIG. 8
800B—enlargement of the first end portion of FIG. 8
800C—cross-sectional enlargement of the first end portion of FIG. 8
800D—enlargement of the second end portion of FIG. 8
800E—cross-sectional enlargement of the second end portion of FIG. 8
805A—propulsion motor
900—top view of the conduit sensor with magnetic shunt with the backing bar weldments and the gear boxes removed
900A—bottom view of the first end of FIG. 9
900B—bottom view of the second end of FIG. 9
900C—perspective view of the first end of FIG. 9
900D—perspective view of the second end of FIG. 9
900E—exploded perspective view of fourth magnet rotor assembly 994
900F—exploded perspective view of magnet rotor assemblies 993 and 994
900G—a schematic perspective view of FIG. 9C indicating rotation of the shunt drive shaft in the clockwise direction as defined from the perspective of the first end of the conduit sensor device and also indicating rotation of the propulsion drive shaft in the clockwise directions as defined from the perspective of the first end of the conduit sensor device
900H—a schematic perspective view of FIG. 9C indicating rotation of the shunt drive shaft in the counter clockwise direction as defined from the perspective of the first end of the conduit sensor device and also indicating rotation of the propulsion drive shaft in the counter clockwise directions as defined from the perspective of the first end of the conduit sensor device
900I—a schematic perspective view of FIG. 9D indicating rotation of the shunt drive shaft in the clockwise direction as defined from the perspective of the first end of the conduit sensor device and also indicating rotation of the propulsion drive shaft in the clockwise directions as defined from the perspective of the first end of the conduit sensor device
900J—a schematic perspective view of FIG. 9D indicating rotation of the shunt drive shaft in the counter clockwise direction as defined from the perspective of the first end of the conduit sensor device and also indicating rotation of the propulsion drive shaft in the counter clockwise directions as defined from the perspective of the first end of the conduit sensor device.
901, 902, 903, 904—wheel bearings
905—propulsion output spur gear
905—spur gear driven by propulsion motor 905A
950—arrow indicating clockwise direction of shaft 401 viewed from first end
951—arrow indicating clockwise direction of shaft 550 viewed from first end
952—arrow indicating clockwise direction of worm wheel 614 viewed from above first end
952A—arrow indicating clockwise direction of vertical worm 612 viewed from above first end
953—arrow indicating clockwise rotation of first helical gear 514 coupled to magnet rotor assembly 991
954—arrow indicating counter clockwise rotation of third helical gear 414 coupled to third magnet rotor assembly 992
955—arrow indicating the direction of travel of helical gear teeth of helical gears 514, 414 with respect to vertical worm 612
956—arrow indicating the counter clockwise rotation of worm wheel 608
957—arrow indicating the counter clockwise rotation of vertical worm 605
958—arrow indicating the counter clockwise rotation of the worm wheel gear 680 as viewed in FIG. 9G
959—arrow indicating the direction of travel of the helical gear teeth of worm wheel 614
960—arrow indicating the direction of travel of the helical gear teeth of worm wheel 608
961—arrow indicating the counter clockwise rotation of helical wheel gear 644
962—arrow indicating the counter clockwise rotation of left handed vertical worm 643

963—arrow indicating the counter clockwise rotation of worm wheel gear 682 viewed in FIG. 9I
964—arrow indicating the direction of travel of the worm wheel 644 with respect to worm 551
965—arrow indicating the clockwise direction of worm wheel 635
965A—arrow indicating the clockwise direction of vertical worm 636
966—arrow indicating clockwise rotation of fourth helical gear 408
967—arrow indicating counter clockwise rotation of second helical gear 548
968—arrow indication the direction of travel of worm 635 with respect to shunt shaft mounted worm 403
969—arrow indicating the direction of travel of helical gears 408, 548 with respect to vertical worm 636
970—arrow indicating the counter clockwise rotation of worm 402 and shunt shaft 401
971—arrow indicating the counter clockwise rotation of worm 558 and propulsion shaft 550
972—arrow indicating the counter clockwise rotation of worm wheel 614
972A—arrow indicating the counter clockwise rotation of worm 612
973—arrow indicating counter clockwise rotation of first helical gear 514
974—arrow indicating the clockwise rotation of third helical gear 414
975—arrow indicating the counter clockwise rotation of helical gear 635
975A—arrow indicating counter clockwise rotation of worm 636
976—arrow indicating the counter clockwise rotation of fourth helical gear 408
978—arrow indicating the clockwise rotation of second helical gear 548
979—arrow indicating the direction of travel of worm wheel 635 with respect to worm 403
980—arrow indicating the direction of travel of worm wheel 644 with respect to worm 551
981—arrow indicating clockwise rotation of worm wheel 644
982—arrow indicating clockwise rotation of worm 643
983—arrow indicating the rotational of worm wheel 682
984—arrow indicating the direction of travel of worm wheel 682 with respect to worm 643
984A—arrow indicating the direction of travel of helical gears 408, 548 with respect to worm 636
985—arrow indicating clockwise rotation of wheel worm 608
986—arrow indicating direction of travel of worm wheel 608 with respect to worm 558
987—arrow indicating clockwise rotation of vertical worm 605
987A—arrow indicating direction of travel of teeth of worm wheel 680 with respect to vertical worm 605
988—arrow indicating clockwise rotation of worm wheel 680
991—first magnet rotor assembly residing at first end
992—third magnet rotor assembly residing at first end of the device
993—second magnet rotor assembly residing at second end of the device
994—fourth magnet rotor assembly residing at second end
1000—cross-sectional view taken along the lines 10-10 of FIG. 3
1000A—cross-sectional view taken along the lines 10-10 of FIG. 3 with the rotor assemblies 993, 994 rotated 90°
1001, 1002, 1003, 1004—magnetic field lines in the shunted/cancelled position of FIG. 10A
1010—rear or rearward portion of the conduit sensor device
1011—front or forward portion of the conduit sensor device
1012—central portion of the conduit sensor device
1100—cross-sectional view taken along the lines 11-11 of FIG. 3
1101, 1102, 1103, 1104—magnetic field lines in the shunted/cancelled position of FIG. 11A
1100A—cross-sectional view taken along the lines 11-11 of FIG. 3 with the rotor assemblies 991, 992 rotated 90°

The invention has been disclosed by way of example. Those skilled in the art will readily recognize that changes and modifications may be made to the invention without departing from the spirit and the scope of the appended claims.

The invention claimed is:

1. A conduit sensor device, comprising:
   said device includes a first end portion and a second end portion;
   a first magnet rotor assembly resides proximate said first end portion of said device and is rotatable between first and second positions;
   a second magnet rotor assembly resides proximate said second end portion of said device and is rotatable between first and second positions;
   said first magnet rotor assembly includes a first plurality of magnets axially arranged about a first longitudinal axis, said first magnet rotor assembly includes a first top portion and a first bottom portion, said first top and bottom portions secure said first plurality of magnets within said first magnet rotor assembly;
   said second magnet rotor assembly includes a second plurality of magnets axially arranged about a second longitudinal axis, second magnet rotor assembly includes a second top portion and a second bottom portion, said second top and bottom portions secure said second plurality of magnets within said second magnet rotor assembly;
   said first position of said first magnet rotor assembly orients the north pole of each of said first plurality of magnets radially outwardly;
   said first position of said second magnet rotor assembly orients the south pole of each of said second plurality of magnets radially outwardly;
   said second position of said first magnet rotor assembly orients the north pole of each of said first plurality of magnets at an angle of 90° with respect to said first position;
   said second position of said second magnet rotor assembly orients the north pole of each of said second plurality of magnets at an angle of 90° with respect to said first position;
   a first drive mechanism for rotating said first magnet rotor assembly from said first position to said second position and a second drive mechanism for rotating said second magnet rotor assembly from said first position to said second position;
   said first drive mechanism includes a first vertical shunt worm for rotating said first magnet rotor assembly; and,
   said second drive mechanism includes a second vertical shunt worm for rotating said second magnet rotor assembly.

2. A conduit sensor device as claimed in claim 1, further comprising:

a shunt shaft, said shunt shaft extends between said first end portion of said device and said second end portion of said device;
a first shunt shaft worm and a second shunt shaft worm, said first shunt shaft worm and said second shunt shaft worm affixed to said shunt shaft;
a first shunt worm wheel engaging said first shunt shaft worm and a second shunt worm wheel engaging said second shunt shaft worm;
said first shunt worm wheel engaged with said first vertical shunt worm wheel and rotatable therewith;
said second shunt worm wheel engaged with said second vertical shunt worm and rotatable therewith;
a first helical gear affixed to said first magnet rotor assembly;
a second helical gear affixed to said second magnet rotor assembly;
said first helical gear engaged with said first vertical shunt worm;
said second helical gear engaged with said second vertical shunt worm;
said first magnet rotor assembly rotatable with said first helical gear; and,
said second magnet rotor assembly rotatable with said second helical gear.

3. A conduit sensor device as claimed in claim 2, further comprising:
a third magnet rotor assembly residing proximate said first end portion of said device and rotatable between first and second positions;
a fourth magnet rotor assembly resides proximate said second end portion of said device and is rotatable between first and second positions;
said third magnet rotor assembly includes a third plurality of magnets axially arranged about a third longitudinal axis, said third magnet rotor assembly includes a third top portion and a third bottom portion, said third top and bottom portions secure said third plurality of magnets within said third magnet rotor assembly;
said fourth magnet rotor assembly includes a fourth plurality of magnets axially arranged about a fourth longitudinal axis, said fourth magnet rotor assembly includes a fourth top portion and a fourth bottom portion, said fourth top and bottom portions secure said fourth plurality of magnets within said fourth magnet rotor assembly;
said first position of said third magnet rotor assembly orients the north pole of each of said third plurality of magnets radially outwardly;
said first position of said fourth magnet rotor assembly orients the south pole of each of said fourth plurality of magnets radially outwardly;
said second position of said third magnet rotor assembly orients the north pole of each of said third plurality of magnets at an angle of 90° with respect to said first position; and,
said second position of said fourth magnet rotor assembly orients the north pole of each of said fourth plurality of magnets at an angle of 90° with respect to said first position.

4. A conduit sensor device as claimed in claim 3, further comprising:
a third drive mechanism for rotating said third magnet rotor assembly from said first position to said second position and a fourth drive mechanism for rotating said fourth magnet rotor assembly from said first position to said second position;
said third drive mechanism includes said first vertical shunt worm for rotating said third magnet rotor assembly; and,
said fourth drive mechanism includes said second vertical shunt worm for rotating said fourth magnet rotor assembly.

5. A conduit sensor device as claimed in claim 4, further comprising:
a third helical gear affixed to said third magnet rotor assembly;
a fourth helical gear affixed to said fourth magnet rotor assembly;
said third helical gear engaged with said first vertical shunt worm;
said fourth helical gear engaged with said second vertical shunt worm;
said third magnet rotor assembly rotatable with said third helical gear; and,
said fourth magnet rotor assembly rotatable with said fourth helical gear.

6. A conduit sensor device, comprising:
a first end of said device;
a second end of said device;
a first magnet rotor assembly, a second magnet rotor assembly, a third magnet rotor assembly, and a fourth magnet rotor assembly;
said first magnet rotor assembly and said third magnet rotor assembly resides at said first end of said device;
said second magnet rotor assembly and said fourth magnet rotor assembly reside at said second end of said device;
said first and third magnet rotor assemblies are rotationally movable in a range of positions between a first position and a second position at said first end of said device;
said second and fourth magnet rotor assemblies are rotationally movable in a range of positions between a first position and a second position at said second end of said device;
a magnetic shunt shaft includes first and second ends, said first end of said magnetic shunt shaft resides at said first end of said device and said second end of said magnetic shunt shaft resides at said second end of said device;
a first gearbox residing at said first end of said device;
a second gearbox residing at said second end of said device;
a first worm affixed to said first end of said magnetic shunt shaft and a second worm affixed to said second end of said magnetic shunt shaft;
said first gearbox includes: a first wheel worm; a first vertical worm affixed to said first wheel worm; a first helical gear, said first helical gear engages said first vertical worm; and, a third helical gear, said third helical gear engages said first vertical worm gear;
said first magnet rotor assembly affixed to said first helical gear and rotatable therewith;
said third magnet rotor assembly affixed to said third helical gear and rotatable therewith;
said first worm affixed to said first end of said magnetic shunt shaft engages said first wheel worm and drives said first vertical worm affixed to said first wheel worm;
said first vertical worm drives said first helical gear and said first magnet rotor assembly in a first rotational direction between first and second positions and said first vertical worm drives said third helical gear and said third magnet rotor assembly in a second rotational direction opposite to said first rotational direction of said first helical gear between first and second positions;

said second gearbox includes: a second wheel worm; a second vertical worm affixed to said second wheel worm; a second helical gear, said second helical gear engages said second vertical worm; and, a fourth helical gear, said fourth helical gear engages said second vertical worm;

said second magnet rotor assembly affixed to said second helical gear and rotatable therewith;

said fourth magnet rotor assembly affixed to said third helical gear and rotatable therewith;

said second worm affixed to said second end of said magnetic shunt shaft engages said second wheel worm and drives said second vertical worm affixed to said second wheel worm;

said second vertical worm drives said second helical gear and said second magnet rotor assembly in a first rotational direction between said first and second positions and said second vertical worm drives said fourth helical gear and said fourth magnet rotor assembly in a second rotational direction opposite to said first rotational direction of said second helical gear between said first and second positions;

when said first and third magnet rotor assemblies are in said first position and when said second and fourth magnet rotor assemblies are in said first position, a magnetic field of maximum strength is generated between said first and said second magnet rotor assemblies and said third and fourth magnetic rotor assemblies, and, said magnetic field of maximum strength extends into a conduit;

when said first and third magnet rotor assemblies are in said second position and when said second and fourth magnet rotor assemblies are in said second position, no magnetic field exists between said first and second magnet rotor assemblies and no magnetic field exists between said third and fourth magnet rotor assemblies; and, when said first and second magnet rotor assemblies are in a rotational position intermediate said first and second positions, and when said third and fourth magnet rotor assemblies are in a rotational position intermediate said first and second positions, then said strength of said magnetic field between said first and second magnet rotor assemblies is modified according to the rotational positions of said first and second magnet rotor assemblies, and then said strength of said magnetic field between said third and fourth magnet rotor assemblies is modified according to the rotational positions of said second and fourth magnet rotor assemblies.

7. A conduit sensor device as claimed in claim 6, further comprising:

said first magnet rotor assembly includes a magnet, said magnet includes a north pole and a south pole;

said second magnet rotor assembly includes a magnet, said magnet includes a north pole and a south pole;

said third magnet rotor assembly includes a magnet, said magnet includes a north pole and a south pole;

and said fourth magnet rotor assembly includes a magnet, said magnet includes a north pole and a south pole;

when said first and third magnet rotor assemblies are in said first position: said south pole of said magnet of said first magnet rotor assembly faces downwardly away from said conduit and said north pole of said magnet of said first magnet rotor assembly faces upwardly toward said conduit; said south pole of said magnet of said third magnet rotor assembly faces downwardly away from said conduit and said north pole of said magnet of said third magnet rotor assembly faces upwardly toward said conduit; and, when said second and fourth magnet rotor assemblies are in said first position: said south pole of said magnet of said second magnet rotor assembly faces upwardly towards said conduit and said north pole of said magnet of said second magnet rotor assembly faces downwardly away from said conduit; and, said south pole of said magnet of said fourth magnet rotor assembly faces upwardly toward said conduit and said north pole of said magnet of said fourth magnet rotor assembly faces downwardly away from said conduit.

8. A conduit sensor device as claimed in claim 6, further comprising:

said first magnet rotor assembly includes a plurality of magnets, each one of said plurality of magnets includes a north pole and a south pole;

said second magnet rotor assembly includes a plurality of magnets, each one of said plurality of magnets includes a north pole and a south pole;

said third magnet rotor assembly includes a plurality of magnets, each one of said plurality of magnets includes a north pole and a south pole;

and said fourth magnet rotor assembly includes a plurality of magnets, each one of said plurality of magnets includes a north pole and a south pole;

when said first and third magnet rotor assemblies are in said first position: said south poles of each of said plurality of magnets of said first magnet rotor assembly face downwardly away from said conduit and said north poles of each of said plurality of magnets of said first magnet rotor assembly face upwardly toward said conduit; said south poles of each of said plurality of magnets of said third magnet rotor assembly face downwardly away from said conduit and said north poles of each of said plurality of magnets of said third magnet rotor assembly face upwardly toward said conduit; and, when said second and fourth magnet rotor assemblies are in said first position: said south poles of each of said plurality of magnets of said second magnet rotor assembly face upwardly toward said conduit and said north poles of each of said plurality of magnets of said second magnet rotor assembly face downwardly away from said conduit; said south poles of each of said plurality of magnets of said fourth magnet rotor assembly face upwardly toward said conduit and said north poles of each of said plurality of magnets of said fourth magnet rotor assembly face downwardly away from said conduit.

9. A conduit sensor device, as claimed in claim 6, further comprising:

a central portion of said device, a rearward side of said device and a forward side of said device;

said first magnet rotor assembly includes a plurality of magnets, each one of said plurality of magnets includes a north pole and a south pole;

said second magnet rotor assembly includes a plurality of magnets, each one of said plurality of magnets includes a north pole and a south pole;

said third magnet rotor assembly includes a plurality of magnets, each one of said plurality of magnets includes a north pole and a south pole;

and said fourth magnet rotor assembly includes a plurality of magnets, each one of said plurality of magnets includes a north pole and a south pole;

when said first and third magnet rotor assemblies are in said second position: said south poles of each of said plurality of magnets of said first magnet rotor assembly face inwardly toward said central portion of said device and said north poles of each of said plurality of magnets of said first magnet rotor assembly face outwardly toward said rearward side of said device; said south poles of each of said plurality of magnets of said third magnet rotor assembly face inwardly toward said central portion of said device and said north poles of each of said plurality of magnets of said second magnet rotor assembly face forwardly; and, when said second and fourth magnet rotor assemblies are in said second position: said south poles of each of said plurality of magnets of said second magnet rotor assembly face outwardly toward said rearward side of said device and said north poles of each of said plurality of magnets of said second magnet rotor assembly face inwardly toward said center portion of said conduit; said south poles of each of said plurality of magnets of said fourth magnet rotor assembly face forwardly and said north poles of each of said plurality of magnets of said fourth magnet rotor assembly face inwardly toward said central portion of said device.

10. A conduit sensor device, as claimed in claim 6, further comprising:
a central portion of said device, a rearward side of said device and a forward side of said device;
said first magnet rotor assembly includes a plurality of magnets, each one of said plurality of magnets includes a north pole and a south pole;
said second magnet rotor assembly includes a plurality of magnets, each one of said plurality of magnets includes a north pole and a south pole;
said third magnet rotor assembly includes a plurality of magnets, each one of said plurality of magnets includes a north pole and a south pole;
and said fourth magnet rotor assembly includes a plurality of magnets, each one of said plurality of magnets includes a north pole and a south pole;
when said first and third magnet rotor assemblies are in said intermediate position: said south poles of each of said plurality of magnets of said first magnet rotor assembly face partially inwardly at an angle away from said conduit and said north poles of each of said plurality of magnets of said first magnet rotor assembly face partially outwardly at an angle toward said conduit; said south poles of each of said plurality of magnets of said third magnet rotor assembly face partially outwardly at an angle toward said conduit and said north poles of each of said plurality of magnets of said third magnet rotor assembly face partially inwardly at an angle away from said conduit; and,
when said second and fourth magnet rotor assemblies are in said intermediate position: said south poles of each of said plurality of magnets of said second magnet rotor assembly face partially inwardly at an angle away from said conduit and said north poles of each of said plurality of magnets of said second magnet rotor assembly face partially outwardly at an angle toward said conduit; said south poles of each of said plurality of magnets of said fourth magnet rotor assembly face partially outwardly at an angle toward said conduit and said north poles of each of said plurality of magnets of said fourth magnet rotor assembly face partially inwardly at an angle away from said conduit.

11. A conduit sensor device as claimed in claim 6, further comprising:
said first magnet rotor assembly includes a plurality of magnets, each one of said plurality of magnets includes a north pole and a south pole;
said second magnet rotor assembly includes a plurality of magnets, each one of said plurality of magnets includes a north pole and a south pole;
said third magnet rotor assembly includes a plurality of magnets, each one of said plurality of magnets includes a north pole and a south pole;
and said fourth magnet rotor assembly includes a plurality of magnets, each one of said plurality of magnets includes a north pole and a south pole;
when said first and third magnet rotor assemblies are in said first position: said south poles of each of said plurality of magnets of said first magnet rotor assembly face downwardly away from said conduit and said north poles of each of said plurality of magnets of said first magnet rotor assembly face upwardly toward said conduit; said south poles of each of said plurality of magnets of said third magnet rotor assembly face downwardly away from said conduit and said north poles of each of said plurality of magnets of said third magnet rotor assembly face upwardly toward said conduit;
when said second and fourth magnet rotor assemblies are in said first position: said south poles of each of said plurality of magnets of said second magnet rotor assembly face upwardly toward said conduit and said north poles of each of said plurality of magnets of said second magnet rotor assembly face downwardly away from said conduit; said south poles of each of said plurality of magnets of said fourth magnet rotor assembly face upwardly toward said conduit and said north poles of each of said plurality of magnets of said fourth magnet rotor assembly face downwardly away from said conduit;
when said first and second magnet rotor assemblies are in said second position: said south poles of each of said plurality of magnets of said first magnet rotor assembly face inwardly toward said central portion of said device and said north poles of each of said plurality of magnets of said first magnet rotor assembly face outwardly toward said rearward side of said device; said south poles of each of said plurality of magnets of said third magnet rotor assembly face inwardly toward said central portion of said device and said north poles of each of said plurality of magnets of said second magnet rotor assembly face forwardly;
when said second and fourth magnet rotor assemblies are in said second position: said south poles of each of said plurality of magnets of said second magnet rotor assembly face outwardly toward said rearward side of said device and said north poles of each of said plurality of magnets of said second magnet rotor assembly face inwardly toward said center portion of said conduit; said south poles of each of said plurality of magnets of said fourth magnet rotor assembly face forwardly and said north poles of each of said plurality of magnets of said fourth magnet rotor assembly face inwardly toward said central portion of said device;
when said first and third magnet rotor assemblies are in said intermediate position: said south poles of each of said plurality of magnets of said first magnet rotor assembly face partially inwardly at an angle away from said conduit and said north poles of each of said plurality of magnets of said first magnet rotor assembly face partially outwardly at an angle toward said conduit; said south poles of each of said plurality of magnets of said third magnet rotor assembly face partially outwardly at an angle toward said conduit and said north poles of each of said plurality of magnets of said third magnet rotor assembly face partially inwardly at an angle away from said conduit; and, when said second and fourth magnet rotor assemblies are in said intermediate position: said south poles of each of said plurality of magnets of said second magnet rotor assembly face partially inwardly at an angle away from said conduit and said north poles of each of said plurality of magnets of said second magnet rotor assembly face partially outwardly at an angle toward said conduit; said south poles of each of said plurality of magnets of said fourth magnet rotor assembly face partially outwardly at an angle toward said conduit and said north poles of each of said plurality of magnets of said fourth magnet rotor assembly face partially inwardly at an angle away from said conduit.

12. A conduit sensor device as claimed in claim 11, wherein said shunt shaft and said first and second worms rotate counterclockwise when viewed from said first end of said device.

13. A conduit sensor device as claimed in claim 6, wherein said shunt shaft and said first and second worms rotate counterclockwise when viewed from said first end of said device.

14. A conduit sensor device as claimed in claim 6 wherein said shunt shaft and said first and second worms rotate clockwise when viewed from said first end of said device.

15. A conduit sensor device as claimed in claim 11, further comprising:
first and second backing bar weldments;
said first backing bar weldment includes a first magnet rotor assembly housing and a second magnet rotor assembly housing;
said second backing bar weldment includes a third magnet rotor assembly housing and a fourth magnet rotor assembly housing;
said first magnet rotor assembly residing substantially within said first magnet rotor assembly housing;
said second magnet rotor assembly residing substantially within said second magnet rotor assembly housing;
said third magnet rotor assembly residing substantially within said third magnet rotor assembly housing; and,
said fourth magnet rotor assembly residing substantially within said fourth magnet rotor assembly housing.

16. A conduit sensor device as claimed in claim 11, further comprising:
a shunt motor;
said shunt motor includes an output shaft having an output shaft gear;
said shunt shaft includes a spur gear affixed thereto;
said output shaft gear meshes with said spur gear rotating said shunt shaft; and,
said shunt shaft rotatable in a clockwise direction or a counter clockwise direction.

17. A conduit sensor device as claimed in claim 11, wherein:
said shunt shaft is driven clockwise when viewed from said first end;
said second magnet rotor assembly rotates counter clockwise 90° from said first position to said second position viewed from said second end;
said fourth magnet rotor assembly rotates clockwise 90° from said first position to said second position viewed from said second end;
said first magnet rotor assembly rotates clockwise 90° from said first position to said second position viewed from said first end; and,
said second magnet rotor assembly rotates counter clockwise 90° from said first position to said second position viewed from said first end.

18. A process for modifying a magnetic field of a conduit sensor device, said magnetic field in proximity to a ferromagnetic conduit, comprising the steps of:
driving a shunt shaft having first and second worms affixed thereto and rotating therewith;
rotating, using said first worm, a first worm wheel and a first vertical worm affixed thereto;
rotating, using said first vertical worm, a first helical gear and a first magnet rotor assembly affixed to said first helical gear;
rotating, using said second worm, a second worm wheel and a second vertical worm affixed thereto; and,
rotating, using said second vertical worm, a second helical gear and a second magnet rotor assembly affixed to said second helical gear.

19. A process for modifying a magnetic field of a conduit sensor device, said magnetic field in proximity to a ferromagnetic conduit, as claimed in claim 18, further comprising the steps of:
rotating, using said first vertical worm, a third helical gear and a third magnet rotor assembly affixed to said third helical gear; and,
rotating, using said second vertical worm, a fourth helical gear and a fourth magnet rotor assembly affixed to said fourth helical gear.

20. A process for modifying a magnetic field of a conduit sensor device, said magnetic field in proximity to a ferromagnetic conduit, as claimed in claim 19, further comprising the steps of:
wherein said step of rotating said first, second, third and fourth magnet assemblies includes rotating said magnet assemblies from a first position wherein a magnetic field exists between said first magnet assembly and said second magnet assembly and from a first position wherein a magnetic field exists between said third magnet assembly and said fourth magnet assembly to a second position wherein no magnetic field exists between said first magnet assembly and said second magnet assembly and wherein no magnetic field exists between said third magnet assembly and said fourth magnet assembly.

21. A process for modifying a magnetic field of a conduit sensor device, said magnetic field in proximity to a ferromagnetic conduit, as claimed in claim 20, wherein said shunt shaft is rotated bidirectionally.

22. A process for modifying a magnetic field of a conduit sensor device, said magnetic field in proximity to a ferromagnetic conduit, as claimed in claim 20, wherein said first, second, third and fourth magnet assemblies are rotated 90°.

23. A process for modifying a magnetic field of a conduit sensor device, said magnetic field in proximity to a ferromagnetic conduit, as claimed in claim 20, wherein each of said magnet rotor assemblies includes a plurality of magnets and said magnet rotor assemblies are housed and supported in first and second backing bar weldments.

24. A process for modifying a magnetic field of a conduit sensor device, said magnetic field in proximity to a ferromagnetic conduit, as claimed in claim 20, wherein said rotation of said first and third magnet rotor assemblies residing at a first end of said device and said rotation of said second and fourth magnet rotor assemblies residing at a second end of said device is performed synchronously.

25. A process for modifying a magnetic field of a conduit sensor device, said magnetic field in proximity to a ferromagnetic conduit, as claimed in claim 19, wherein said step of:

rotating said first, second, third and fourth magnet assemblies includes rotating said magnet assemblies less than 90°: from a first position wherein a maximum strength magnetic field exists between said first magnet assembly and said second magnet assembly and from a first position wherein a maximum strength magnetic field exists between said third magnet assembly and said fourth magnet assembly, to an intermediate position wherein a lower strength magnetic field exists between said first magnet assembly and said second magnet assembly and wherein a lower strength magnetic field exists between said third magnet assembly and said fourth magnet assembly.

\* \* \* \* \*